US010039663B2

(12) United States Patent
Liden et al.

(10) Patent No.: US 10,039,663 B2
(45) Date of Patent: Aug. 7, 2018

(54) SYSTEM AND METHODS FOR APPLYING A TOTAL CONTACT AND OFFLOADING CAST

(71) Applicant: Hollister Incorporated, Libertyville, IL (US)

(72) Inventors: Brock Liden, Baltimore, OH (US); Spencer Brown, Pierceton, IN (US)

(73) Assignee: Hollister Incorporated, Libertyville, IL (US)

(*) Notice: Subject to any disclaimer, the term of this patent is extended or adjusted under 35 U.S.C. 154(b) by 191 days.

(21) Appl. No.: 14/329,933

(22) Filed: Jul. 12, 2014

(65) Prior Publication Data

US 2015/0025432 A1 Jan. 22, 2015

Related U.S. Application Data

(60) Provisional application No. 61/978,891, filed on Apr. 13, 2014, provisional application No. 61/845,921, filed on Jul. 12, 2013.

(51) Int. Cl.
*A61F 5/00* (2006.01)
*A61F 5/01* (2006.01)
(Continued)

(52) U.S. Cl.
CPC .......... *A61F 5/0127* (2013.01); *A61F 5/0195* (2013.01); *A61F 5/05* (2013.01);
(Continued)

(58) Field of Classification Search
CPC ........ A61F 5/0127; A61F 5/0195; A61F 5/05; A61F 13/069
(Continued)

(56) References Cited

U.S. PATENT DOCUMENTS 4,888,225 A 12/1989 Sandvig et al.
5,637,077 A * 6/1997 Parker .................. A61F 5/0111
602/27
(Continued)

FOREIGN PATENT DOCUMENTS

EP 1148852 A2 10/2001
JP 9234241 A 9/1997
(Continued)

OTHER PUBLICATIONS

Coppard et al.,Introduction to Splinting a Clinical Reasoning & Problem-Solving Approach 3rd Edition, p. 219, 2008.*
(Continued)

*Primary Examiner* — Kim M Lewis
(74) *Attorney, Agent, or Firm* — Grogan, Tuccillo & Vanderleeden, LLP

(57) ABSTRACT

Some implementations of the described invention relate to systems and methods for applying a total contact cast to a patient for treatment of a wound on an appendage, such as a leg or foot. While the cast system can comprise any suitable component, in some cases, it includes a clam-shell cast, a foot support defining (or customizable to define) an offloading hole, and a cast underlayment (such as a compression sock, a padding sock, and/or additional padding). In some implementations, a first length of the clam-shell cast is applied to a patient's calf, a second length of the cast is applied to across a patient's foot, and a third length is folded up over the patient's foot to extend up a portion of the patient's calf. In some cases, a strap or wing is used to attach the first and the third lengths together. Other implementations are also described.

21 Claims, 49 Drawing Sheets

(51) Int. Cl.
*A61F 5/05* (2006.01)
*A61F 5/058* (2006.01)
*A61F 13/04* (2006.01)

(52) U.S. Cl.
CPC ............ *A61F 5/0585* (2013.01); *A61F 13/04* (2013.01); *A61F 2210/0085* (2013.01)

(58) Field of Classification Search
USPC ................................ 602/5–8, 12, 27–29, 10
See application file for complete search history.

(56) References Cited

U.S. PATENT DOCUMENTS

| | | | |
|---|---|---|---|
| 6,228,044 B1 | 5/2001 | Jensen et al. | |
| 6,656,142 B1 * | 12/2003 | Lee .......................... | A61F 5/058 128/881 |
| 6,974,431 B2 | 12/2005 | Jensen et al. | |
| 7,666,155 B1 | 2/2010 | Jensen et al. | |
| 7,758,529 B2 | 7/2010 | Jensen et al. | |
| 8,083,704 B2 | 12/2011 | Jensen et al. | |
| 2002/0095105 A1 | 7/2002 | Jensen | |
| 2003/0212358 A1 | 11/2003 | Cavanagh et al. | |
| 2004/0111048 A1 | 6/2004 | Jensen et al. | |
| 2004/0215121 A1 | 10/2004 | Parker | |
| 2005/0027219 A1 * | 2/2005 | Schultze ............... | A61F 13/107 602/3 |
| 2005/0228324 A1 * | 10/2005 | Stanton ................... | A61L 15/12 602/8 |
| 2006/0135899 A1 | 6/2006 | Jerome et al. | |
| 2008/0039758 A1 | 2/2008 | Jensen et al. | |
| 2008/0319362 A1 | 12/2008 | Joseph | |
| 2010/0130902 A1 | 5/2010 | Jensen et al. | |
| 2011/0152735 A1 * | 6/2011 | Barberio ................... | A61F 5/05 602/14 |
| 2011/0288458 A1 | 11/2011 | Jones et al. | |
| 2013/0018294 A1 | 1/2013 | Jones et al. | |

FOREIGN PATENT DOCUMENTS

| | | |
|---|---|---|
| JP | 11104157 A | 4/1999 |
| JP | 2002102263 A | 4/2002 |
| WO | WO 2000/040202 A2 | 7/2000 |
| WO | WO 2008/021986 A2 | 2/2008 |
| WO | WO 2011/130676 A2 | 10/2011 |
| WO | WO 2012/099989 A2 | 7/2012 |

OTHER PUBLICATIONS

Office Action dated Feb. 24, 2017 issued by the Canadian Patent Office in connection with the corresponding Canadian Patent Application No. 2917164.
Office Action dated Mar. 17, 2017 issued by the European Patent Office in connection with the corresponding European Patent Application No. 14822068.4.

* cited by examiner

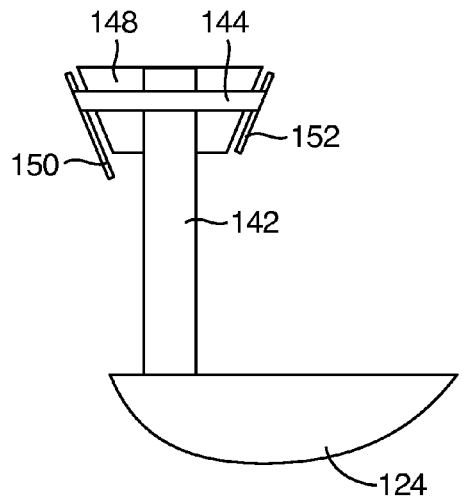
FIG. 12L
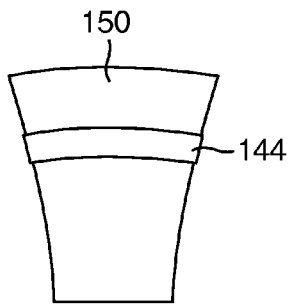   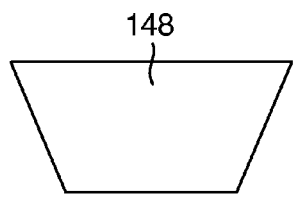   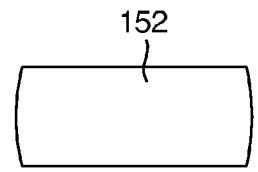
FIG. 12M        FIG. 12N        FIG. 12O
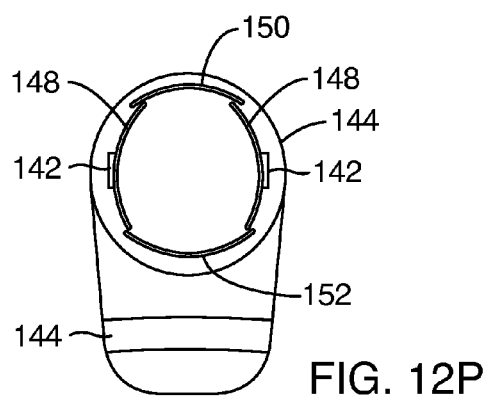
FIG. 12P

SYSTEM AND METHODS FOR APPLYING A TOTAL CONTACT AND OFFLOADING CAST

CROSS-REFERENCE TO RELATED APPLICATIONS

This application claims priority to U.S. Provisional Patent Application Ser. No. 61/845,921, filed Jul. 12, 2013, and entitled "SYSTEMS AND METHODS FOR PROVIDING AN ORTHOPEDIC DEVICE," and claims priority to U.S. Provisional Patent Application Ser. No. 61/978,891, filed Apr. 13, 2014, and entitled "SYSTEMS AND METHODS FOR PROVIDING A TOTAL CONTACT AND OFFLOADING CAST;" the entire disclosures of which are both hereby incorporated by reference.

BACKGROUND OF THE INVENTION

Field of the Invention

The present invention relates to orthopedic casts. In particular, some implementations of the present invention relate to one or more components of a total contact cast system that can be used in the treatment of an appendage, such as a leg or foot. Indeed, in some implementations, the described cast system is configured to support a patient's foot and leg, while offloading weight from a sore, ulcer, or wound on the patient's foot.

Background and Related Art

People across the world suffer from ulcerations and injuries to one or both of their feet. For instance, as many people suffering from diabetes also suffer from poor blood flow in their appendages, such people can be at a relatively high risk of developing sores, wounds, or ulcers on their feet—especially on the soles of their feet. Such sores, ulcers, and other wounds can dramatically affect an individual's life, limiting the individual's ability to walk, work, and play, and costing the individual (or others) relatively large amounts of money and time spent in, and for, recovery. Additionally, in some extreme cases, such sores, ulcers, and wounds can lead to amputation, which can dramatically increase healthcare costs, and otherwise complicate life.

One important factor in healing foot wounds is offloading the patient's weight from the wound. However, as many individuals (including diabetics) suffer from neuropathy (or nerve damage in one or more appendages), many such individuals often cannot feel the pain that is normally associated with foot sores, ulcerations and/or wounds. As a result, some such individuals may not be highly motivated by pain to reduce pressure applied to a damaged portion of the foot, which may ultimately lead to tissue breakdown, ulceration, and other damage. Accordingly, some such individuals may continue to place detrimental amounts of weight on their foot and/or a wound thereon—thus causing the wound to further deteriorate, and thus, increasing the chances of infection and other comorbidities.

Several casts, boots, and other devices have been developed to treat individuals suffering from foot ulcerations, sores, and other wounds. While some such devices have been useful in the treatment of such wounds, such devices are not necessarily without their shortcomings. Indeed, some conventional devices for treating foot wounds are relatively: hard to put on, hard to take off, uncomfortable, non-breathable, ineffective at offloading weight from wounds in abnormal locations, hard to use with other apparatus (e.g., negative pressure wound therapy), and/or are otherwise difficult to use or ineffective at treating these wounds.

Thus, while techniques currently exist that are used to treat foot wounds, ulcerations, and sores, challenges still exist, including those mentioned above. Accordingly, it would be an improvement in the art to augment or even replace current techniques with other techniques.

SUMMARY OF THE INVENTION

The present invention relates to orthopedic casts. In particular, some implementations of the present invention relate to one or more components of a total contact cast system that can be used in the treatment of an appendage, such as a leg or foot. Indeed, in some implementations, the described cast system is configured to support a patient's foot and leg, while offloading weight from a wound on the patient's foot and distributing such weight to one or more other portions of the patient's leg (e.g., a forefoot, arch, heel, Achilles tendon, cone of the lower leg, etc.).

While the described orthopedic cast system can comprise any suitable component or characteristic, in some implementations, it includes a "clam-shell" cast, a foot support, one or more cast underlayments, and/or a footplate/boot. With respect to the clam-shell cast (or cast), the cast can comprise any suitable component or characteristic that allows it to be applied over a first surface of a patient's body (e.g., a posterior portion of a patient's lower leg or calf), to be applied over a portion of the patient's foot, and then to be applied over a second surface of the patient's body (e.g., an anterior portion of a patient's lower leg or shin), wherein the second surface is substantially opposite to the first surface. Indeed, in some cases, the cast comprises an elongated piece of hardenable casting material that is configured to extend substantially vertically along a longitudinal axis of a posterior portion (or calf) of a patient's lower leg, bend around the patient's heel, extend along a sole of the patient's foot, bend up over one or more of the patient's toes, extend across a dorsal portion of the patient's foot, and extend vertically along an anterior portion (or shin) of the patient's lower leg.

While an anterior portion and a posterior portion of the cast can be attached to each other and a patient's appendage (e.g., lower leg) in any suitable manner (e.g., via one or more elastic bands, pieces of casting material, belts, cords, straps, ties, fasteners, pieces of tape, and/or any other suitable connector), in some embodiments, the cast comprises one or more straps and/or wings that are configured to extend from the anterior and/or the posterior portion of the cast and to overlap the opposite portion of the cast. While these wings and/or straps can perform any suitable function, in some instances, they connect various portions of the cast together, strengthen the cast, and/or help spread weight across a portion of an appendage (thereby offloading weight from a wound on the appendage).

With regard to the foot support, the foot support can comprise any suitable padding that allows a portion of the patient's weight to be offloaded from a wound on the sole (or another portion) of the patient's foot. In some implementations, the padding comprises at least two layers of padding, with each layer having a different durometer value. As a result, some such implementations are able to cushion a foot, while offloading pressure from a wound on the foot.

In some implementations, the foot support defines (or is configured to readily be modified to define) an offloading hole that is configured to correspond in position to (and otherwise reduce pressure that is applied to) a wound on a patient's foot. While such an offloading hole can be defined in the foot support in any suitable manner, in some implementations (depending on the type of foot support selected), the hole is cut in the support (e.g., free hand, with a scissors, a punch, knife, etc.), is made by removing portions of the support along one or more perforated lines in the support, and/or by adding to the foot support an additional padding layer defining an offloading hole.

In some implementations, the foot support further comprises a toe guard that is configured to be disposed within the cast and to extend over a portion of one or more of a patient's toes. While the toe guard can comprise any suitable characteristic that allows it to function as described, in some cases, the toe guard comprises a portion having a box shape, a rounded shape, and/or another suitable shape that is resiliently (or rigidly) formed in the foot support to help protect a patient's toes.

With respect to the cast underlayment, the underlayment can comprise any suitable material that is configured to be disposed between an internal surface of the cast and the skin of an appendage (or other body part) within the cast. Indeed, in some implementations, the underlayment comprises one or more layers of an antimicrobial material (e.g., an anti-fungal and anti-bacterial material). Some examples of such material include, but are not limited to, bamboo fabrics, bamboo rayon, silver-coated fabric (e.g., silver-coated poly (ethylene terephthalate), silver-coated rayon, silver-coated polyester, iodine incorporated cloth, etc.), copper-coated fabric, silver/copper-coated fabric, silver/copper/nickel-coated fabric, silver/copper/tin-coated fabric, and/or any other material with one or more antimicrobial and/or anti-odor characteristics. In some implementations, however, the underlayment comprises a fabric containing bamboo.

While the underlayment can comprise any suitable component, in some implementations, the underlayment comprises a padding layer, a compression layer, and/or a bandage (or localized padding) layer. Where the underlayment comprises a padding layer, the padding layer can comprise any suitable material, including, without limitation, a padded sock or stockinette (e.g., a sock or stockinette comprising bamboo fabric). Where the underlayment comprises a compression layer, the compression layer can comprise any suitable material, including a compression sock or stockinette (e.g., a sock or stockinette comprising bamboo fabric) that is configured to provide any suitable amount of pressure when worn on an appendage (e.g., between about 8 and about 25 mmHg).

In some implementations in which the underlayment comprises 2, 3, 4, 5, or more layers of one or more materials, the underlayment functions as a multi-layer shear reduction system, allowing two or more layers of the underlayment to move independent of each other, and thereby allow shearing movement between the skin of a casted appendage and the cast itself to take place between the multiple layers of the underlayment (e.g., the padding sock and the compression sock), instead of at the surface of the patient's skin.

With reference to the footplate/boot, some implementations of the described cast system (and its various components) are configured to be used (e.g., walked on) without a footplate or boot. In other implementations, however, one or more components of the cast are used with a footplate and/or a boot. With respect to the footplate, the footplate can comprise any suitable feature that it to support a patient's foot and/or offload weight from a wound on the sole of the patient's foot. Indeed, in some instances, a posterior portion of the footplate defines a recess that is configured to cradle and/or correctly position the patient's heel on the footplate. In some case, the footplate further comprises a cam-shaped undersurface. In such cases, an eccentric portion of the cam-shaped undersurface of the footplate can be disposed in any suitable location, including, without limitation, being disposed anteriorly, posteriorly, laterally, medially, and/or in the middle of (or with respect to) the length of the footplate.

With respect to the boot, the boot can comprise any suitable characteristic or component that allows it to support a portion of a patient's leg. Indeed, in some implementations, the boot comprises a footplate with one or more upright supports that allow the footplate to be attached to a patient's leg. While the upright supports can comprise any suitable component, in some implementations, the upright supports are configured to be attached to one or more attachment mechanisms, which can include, but are not limited to, one or more straps, cords, and/or other devices that are capable of securing the upright supports to a patient's leg. Additionally, in some implementations, the upright supports include one or more flaps (e.g., lateral flaps, medial flaps, posterior flaps, anterior flaps, etc.) that help distribute pressure from the upright supports across a portion of the patient's leg. In such embodiments, the flaps can have any suitable characteristic. Indeed, in some embodiments, one or more of the internal surfaces of the flaps (e.g., the surfaces that are configured to interface with the cast) comprises a material, texturing, and/or other feature that allows it to maintain its position with respect to the cast (e.g., as the patient walks in the boot).

While the described systems and methods may be particularly useful in the area of treating one or more sores, ulcerations, and/or other wounds on the sole (and other portions) of an individual's foot, those skilled in the art can appreciate that the described apparatus, systems, and methods can be used in a variety of different applications and in a variety of different areas of manufacture to treat a wide range of injuries to an individual's appendages (e.g., arms, hands, fingers, toes, legs, etc.), and in any suitable location. Indeed, in some implementations, the described antimicrobial underlayment (e.g., compression sock and/or padding sock), foot support, and/or cast (or modified versions thereof) are used in an arm cast, a hand cast, and/or in any other suitable cast or splint system.

These and other features and advantages of the present invention will be set forth or will become more fully apparent in the description that follows. Furthermore, the features and advantages of the invention may be learned by the practice of the invention or will be obvious from the description, as set forth hereinafter.

BRIEF DESCRIPTION OF THE DRAWINGS

In order that the manner in the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIG. 12L illustrates a side elevation view of a representative embodiment of the boot;

FIGS. 12M-12O each illustrates a side elevation view of representative embodiments of a boot flap;

FIG. 12P illustrates a top plan view of the representative embodiment of the boot;

DETAILED DESCRIPTION OF THE INVENTION

The present invention relates to orthopedic casts. In particular, some implementations of the present invention relate to one or more components of a total contact cast system that can be used in the treatment of an appendage, such as a leg or foot. Indeed, in some implementations, the described cast system is configured to support a patient's foot and leg, while offloading weight from a wound on the patient's foot. In this regard, the term wound may be used herein to refer to a sore, ulcer, cut, incision, laceration, puncture, pustule, skin graft, stitched portion of skin or flesh, bruise, boil, contusion, broken bone, and/or any other suitable injury that can be covered, offloaded, cushioned, protected, and/or otherwise be treated with one or more components of the described cast system.

In the disclosure and in the claims, the term lower leg (and variations thereof) may be used to refer to any portion of a patient's leg that is located distal to the patient's knee.

The term hardenable casting material (and variations thereof) may be used herein to refer to a suitable known or novel material that is configured to be pliable and moldable when being applied to a patient, and that can readily be hardened to function as an orthopedic cast.

The terms patient and individual (and variations thereof) may be used herein to refer to any person or other subject that can wear or use any and/or all portions of the described cast system.

The term sock (and variations thereof) may be used to herein to refer to a sock, stockinette, sleeve, sheath, casing, covering, tube, wrap, and/or similar object.

The term total contact cast may be used herein to refer to an orthopedic cast having a shape that substantially conforms to a portion of a patient's lower leg so as to spread weight from the patient's leg across a larger surface area than the typical contact areas of the sole of the patient's foot.

Figure 1A:
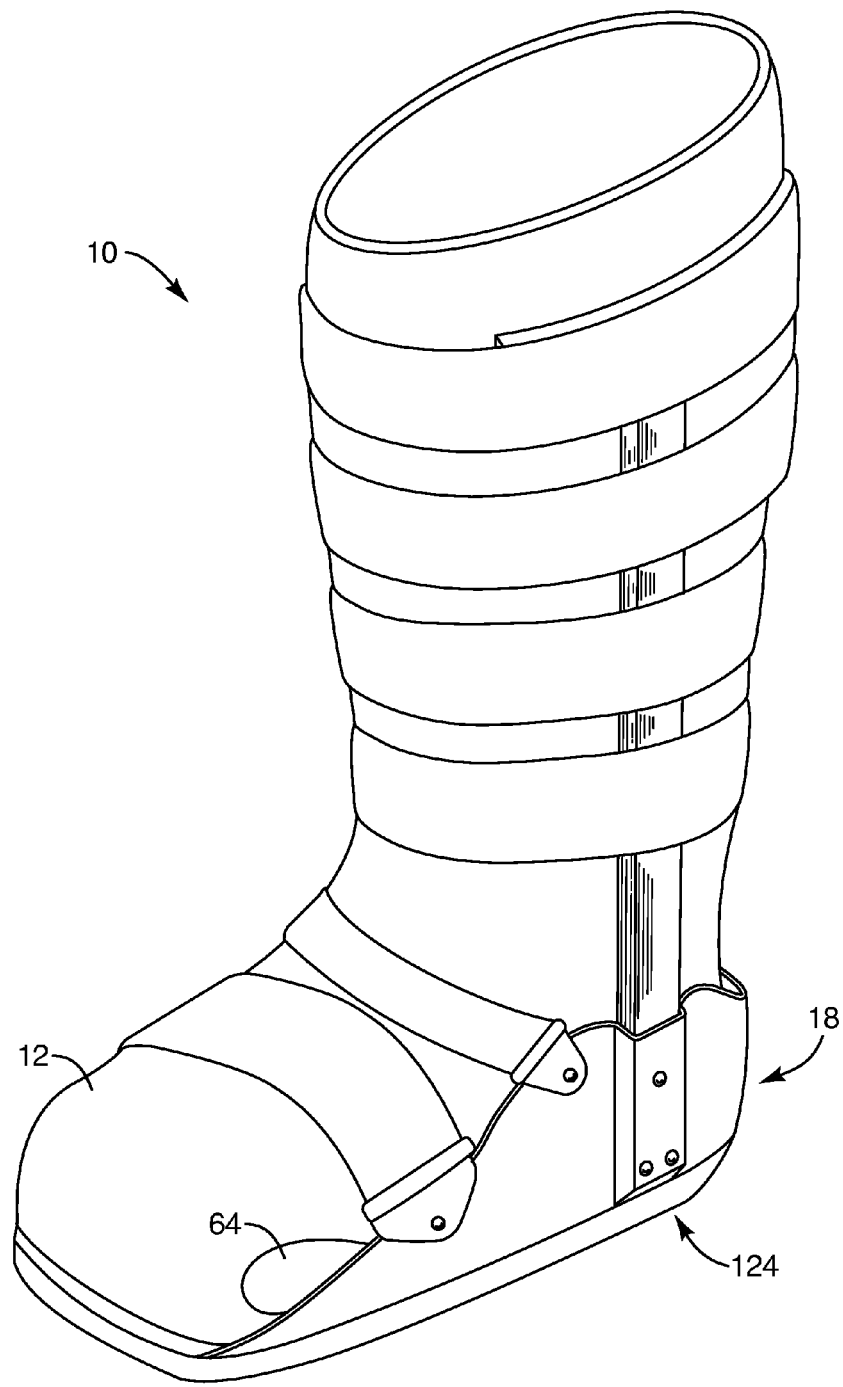
FIG. 1A illustrates a perspective view of a representative embodiment of an orthopedic cast system.
Figure 1B:
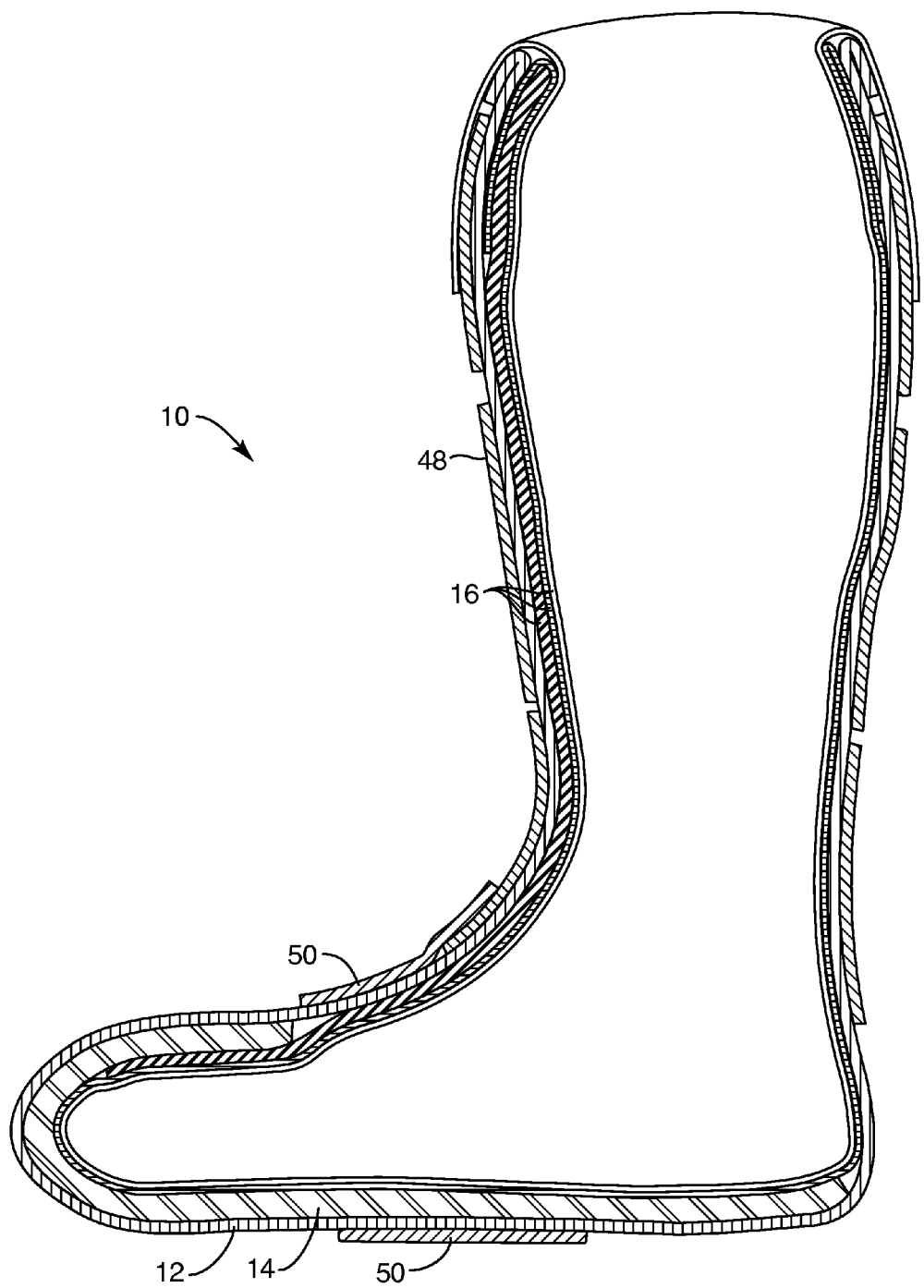
FIG. 1B illustrates a cross-sectional view of a representative embodiment of the orthopedic cast system.
Figure 1C:
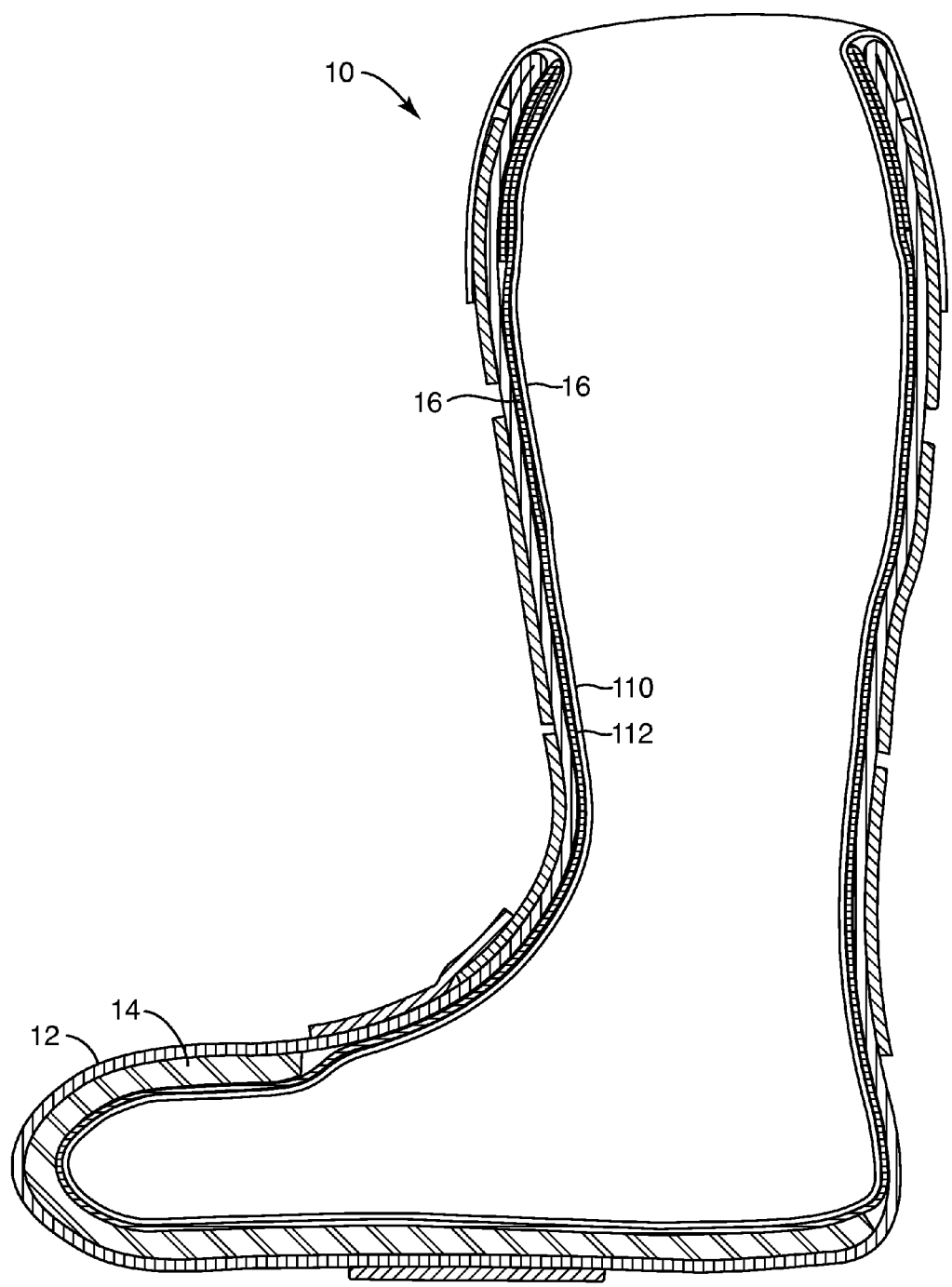
FIG. 1C illustrates a cross-sectional view of a representative embodiment of the orthopedic cast system.

Although the described orthopedic cast system can comprise any suitable component or characteristic that allows it to cover and protect a wounded portion of a person's body, FIG. 1A shows a representative embodiment of the orthopedic cast system 10. More specifically, FIGS. 1B-1C) show some embodiments in which the cast system 10 comprises a clam-shell cast 12, a foot support 14, and a cast underlayment 16 each of which can be used independently or in connection with each other and/or a footplate or a boot (such as the boot 18 shown in FIG. 1A). To provide a better understanding of the described orthopedic cast system and its various components, the following disclosure is grouped into five subheadings, namely "CLAM-SHELL CAST," "FOOT SUPPORT," "CAST UNDERLAYMENT," "FOOTPLATE/BOOT," and "ASSOCIATED METHODS." In this regard, the utilization of the subheadings is for convenience of the reader only, and is not to be construed as being limiting in any sense.

Clam-Shell Cast

With respect to the cast 12, the cast can comprise any suitable characteristic that allows it to extend over a first surface of a patient's appendage (e.g., lower leg), over an end of the appendage, and over a second surface of the appendage, which is substantially opposite to the first surface. Indeed, because, in at least some embodiments, a first portion of the cast is configured to cover a first surface of an appendage and a second portion of the cast is configured to cover a second surface of the appendage that is substantially opposite to the first surface of the appendage (thus sandwiching the appendage (or another suitable body part) between two portions of the cast), the cast is sometimes called a clam-shell cast.

Figure 2A:
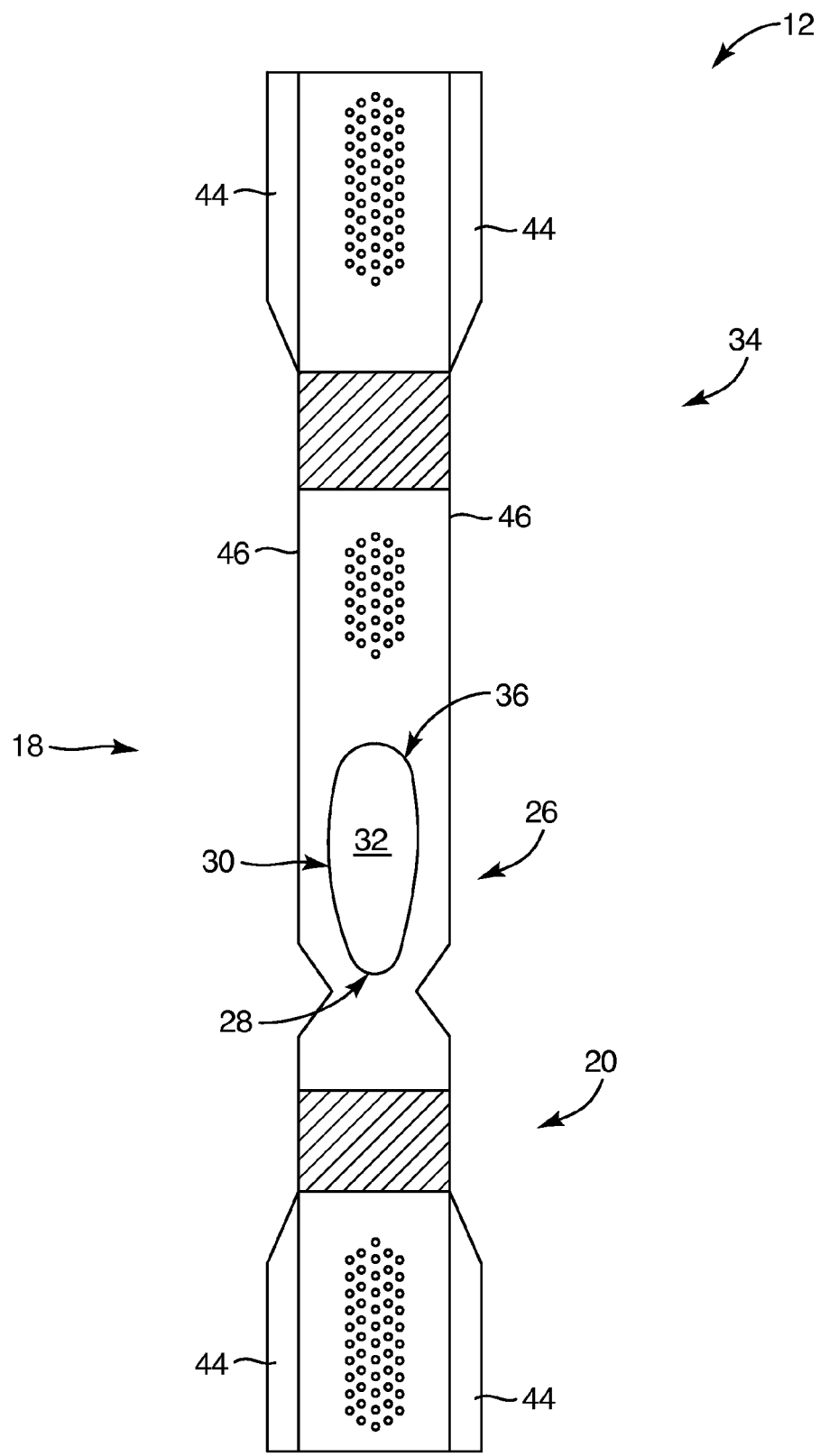
FIG. 2A illustrates a top plan view of a representative embodiment of a clam-shell cast.
Figure 2B:
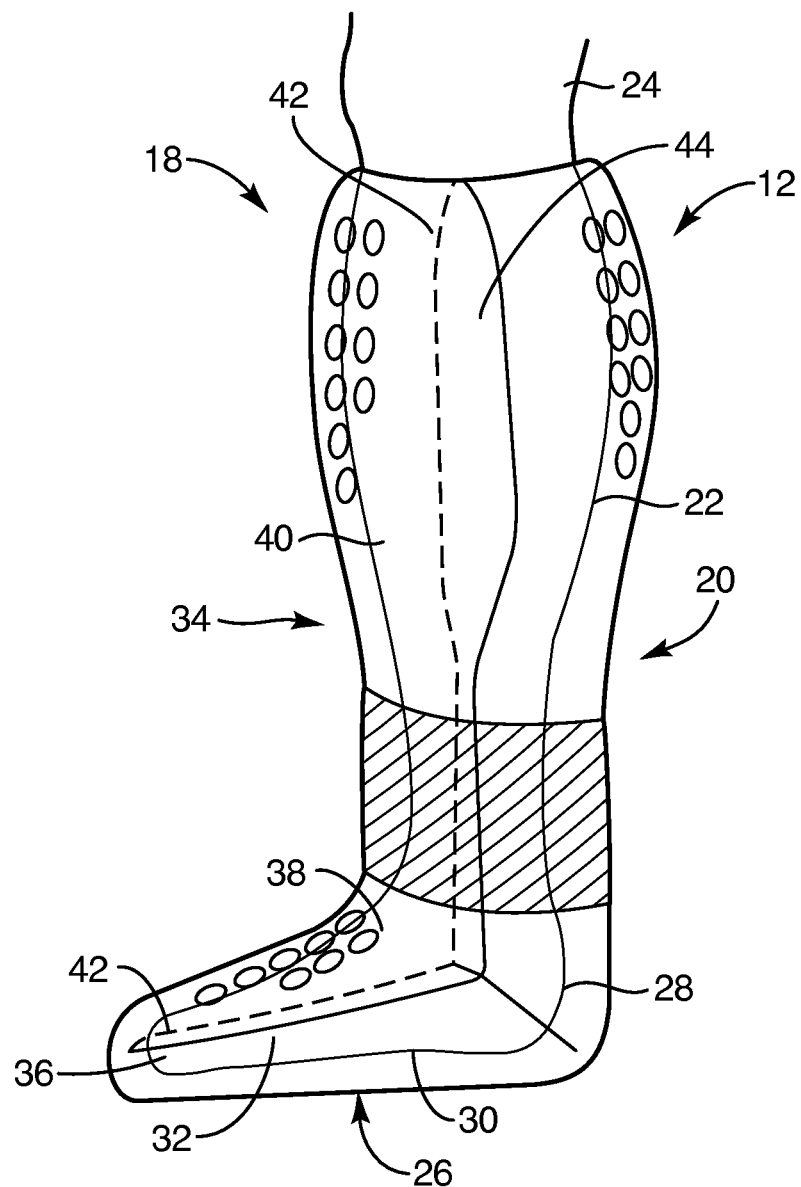
FIG. 2B illustrates a side elevation view of a representative embodiment of the clam-shell cast disposed on a patient, wherein the cast is illustrated as being semi-transparent to provide a non-limiting illustration of a relation between the cast and the patient's leg.

While the cast 12 can comprise any suitable component that allows it to function as described herein, FIGS. 2A-2B show some embodiments in which the cast 12 comprises an elongated piece of hardenable casting material 18 (or the elongated casting material 18). While the elongated casting material can have any suitable component, FIGS. 2A-2B show that, in some embodiments, the casting material 18 has a first portion 20 that is configured to extend over a posterior portion 22 of a patient's lower leg 24 (e.g., calf); a second portion 26 that is configured to extend over the patient's heel 28 and extend across a length of the sole 30 of the patient's foot 32; and a third portion 34 that is configured to extend over an anterior end of the patient's foot (e.g., toes 36), run across a dorsal portion 38 of the patient's foot, and extend up over an anterior portion 40 of the patient's lower leg 24 (e.g., shin).

The clam-shell cast 12 can comprise any suitable hardenable casting material that allows the cast to substantially conform to the shape of an appendage (e.g., lower leg 24) during application of the cast, and to then harden in that shape to form an orthopedic cast. In this regard, by substantially conforming to the shape of an appendage, the cast can help spread weight from a portion of the appendage (e.g., the sole 30 of a foot 32) to a larger portion of the appendage. In other words, in some embodiments, the cast itself allows its patient to offload weight from a foot wound and to spread such weight to other portions of the patient's lower leg.

Figure 4A:
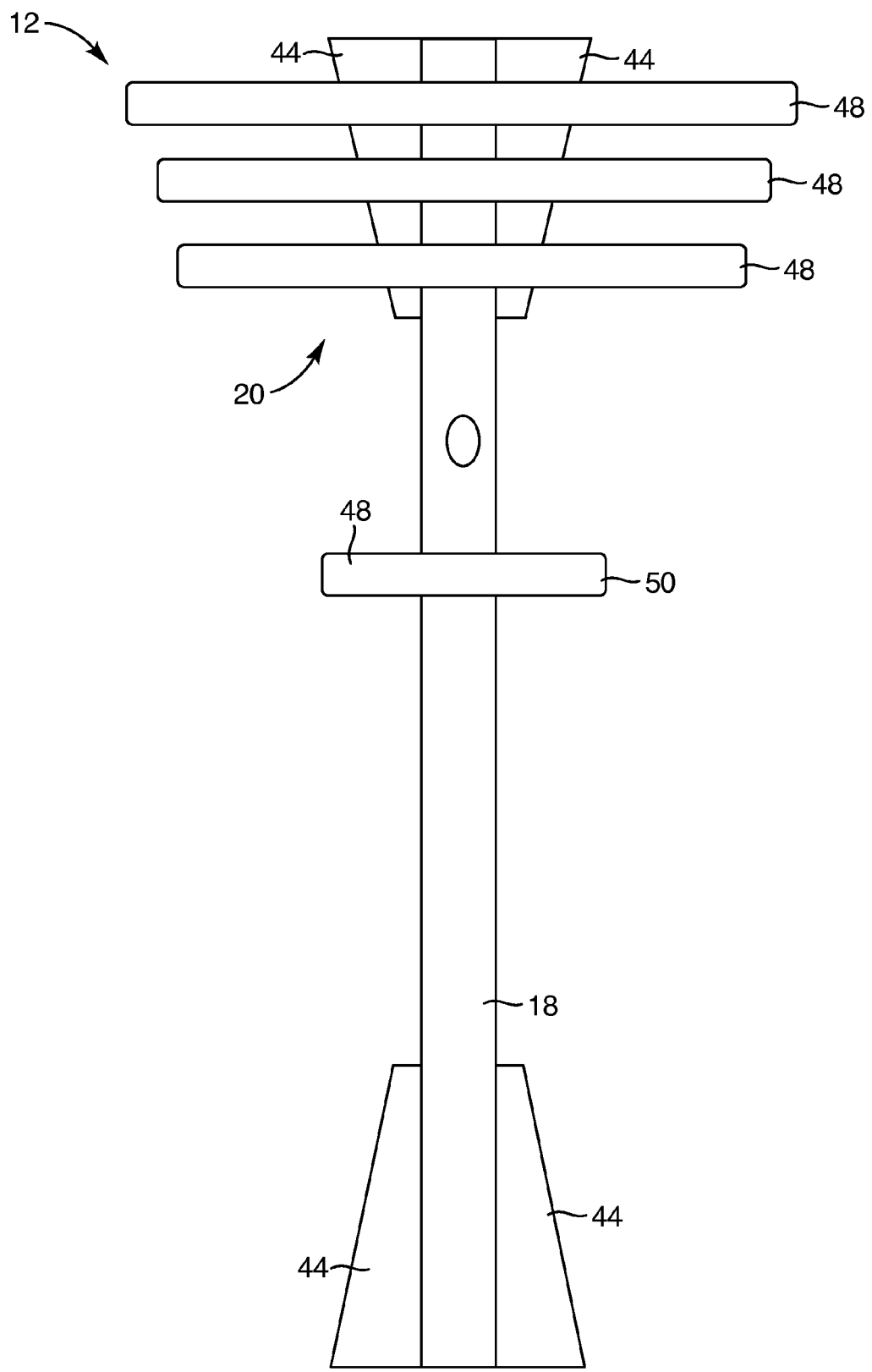
FIGS. 4A-4D each illustrates a top plan view of representative embodiments of the clam-shell cast.
Figure 4B:
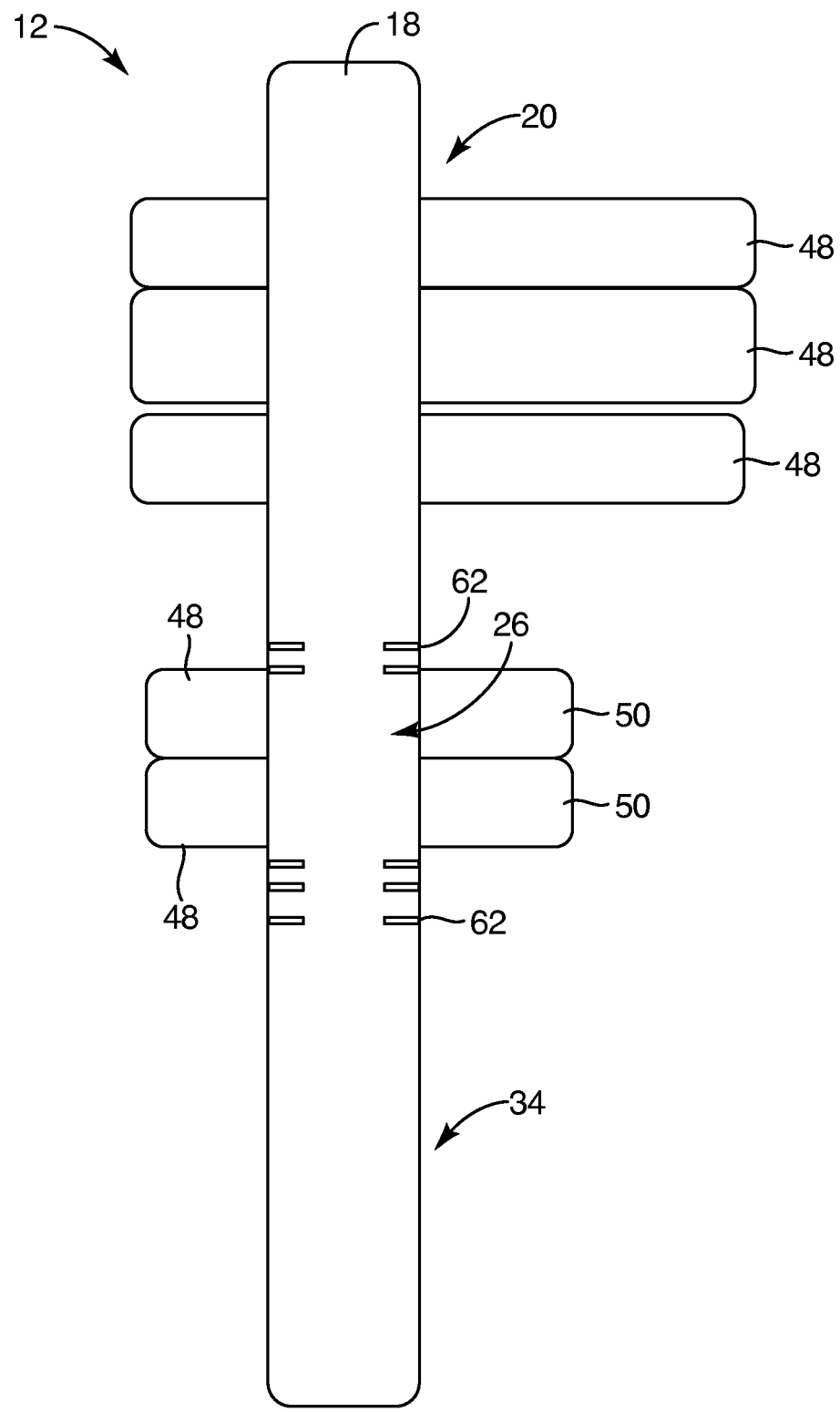
Figure 4C:
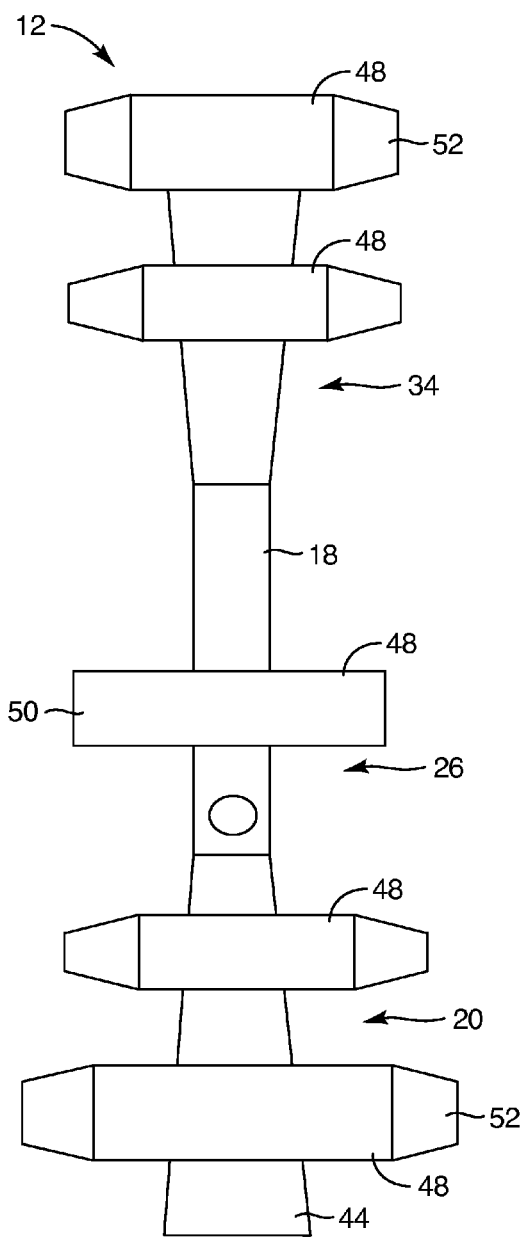
Figure 4D:
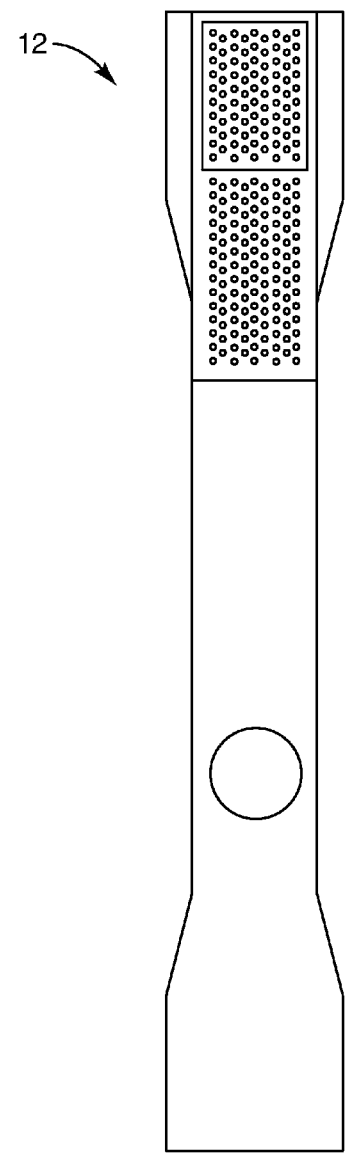
Figure 4E:
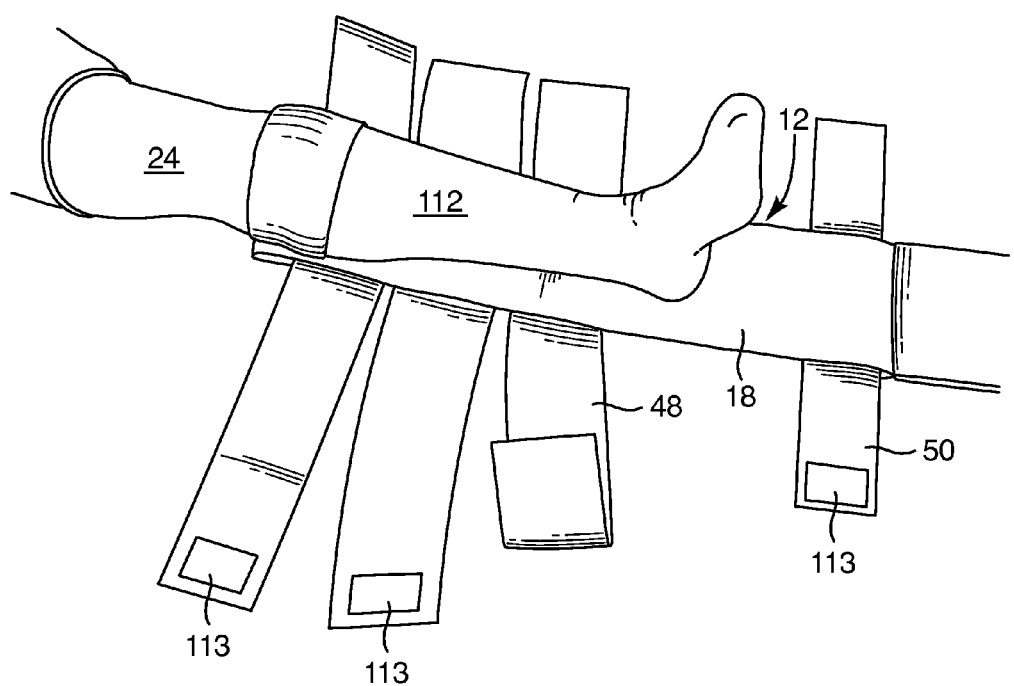
FIG. 4E illustrates a perspective view of a representative embodiment of the clam-shell cast.

Some examples of hardenable casting materials include, but are not limited to, any known or novel and suitable: fiberglass casting material (e.g., fiberglass that has been impregnated with polyurethane and/or another suitable material; fiberglass that is coated with and/or otherwise comprises silver, copper, nickel, iodine, bamboo, and/or another suitable antimicrobial material and/or anti-odor material; any other suitable type of fiberglass casting; and/or combinations thereof), hardenable bandaging (e.g., cotton bandaging that is coated with plaster, polyester bandaging that is covered with plaster, any other suitable casting material that is configured to a harden after application), a thermoplastic casting material, etc.), a polypropylene casting material, a carbon fiber casting material, a hardenable antimicrobial material (e.g., plaster or another suitable hardenable material covering: a bamboo cloth, a bamboo rayon, a polyester made from bamboo, another fabric comprising bamboo, a silver-coated fabric (e.g., silver-coated poly(ethylene terephthalate), silver-coated rayon, silver-coated polyester, etc.), a copper-coated fabric, a silver/copper-coated fabric, a silver/copper/nickel-coated fabric, a silver/copper/tin-coated fabric, an iodine incorporated cloth, and/or any other suitable material having one or more antimicrobial and/or anti-odor features), a casting material (e.g., fiberglass, cotton bandaging, and/or any other suitable casting material) that is impregnated with and/or otherwise comprises any suitable antibiotic, bactericide, and/or other antimicrobial ingredient, which may include, without limitation, penicillin, amikacin, gentamicin, kanamycin, netimicin, tobramycin, streptomycin, spectinomycin, geldanamycin, herbimycin, rifaximin, ertapenem, doripenem, imipenem, meropenem, defadroxil, cefazolin, cefalotin, cephalexin, and/or any other suitable antimicrobial), casting tape, and/or any other suitable material that is configured to be formed around a portion of a patient's body (e.g., the patient's leg and foot) and then to be hardened to form an orthopedic cast. Indeed, in some embodiments, the hardenable casting material comprises a known or novel fiberglass casting material that is configured to begin hardening once it has been exposed to air and/or water.

Where a portion of the cast 12 (e.g., the first portion 20) is configured to extend over a first surface of an appendage (e.g., a calf) and another portion of the cast (e.g., the third portion 34) is configured to extend over a second, substantially opposite, portion of the appendage (e.g., a shin), the various portions of the cast can be attached to each other in any suitable manner that allows the cast to function as a total contact cast. In some embodiments, the various portions of the cast are attached to each other and/or an appendage (e.g., a lower leg) through the use of one or more wings, portions of the cast that are configured to overlap other portions of the cast, straps, belts, cords, bands, pieces of casting material, mechanical engagements, non-mechanical engagements, fasteners, frictional engagements, hook and loop fasteners, snaps, buckles, slides, ties hinges, flexible portions, and/or any other suitable connector. By way of non-limiting illustration, FIG. 2B shows an embodiment in which the dotted lines 42 indicate an overlap of various portions of the cast 12 (i.e., a wing 44). Additionally (and jumping a little ahead in the figures), FIG. 4E shows that, in some embodiments, one or more straps 48 and 50 of the cast 12 are configured to attach to each other and/or a portion of the cast 12 via a fastener 113 (e.g., a hook and loop fastener).

In embodiments in which the cast 12 comprises a wing 44, the wing can perform any suitable function. Indeed, in some instances, the wings are configured to attach at least one portion of the cast to at least one other portion of the cast and/or to cradle, and distribute pressure across, a portion of the patient's appendage (e.g., lower leg 24).

Figure 2C:
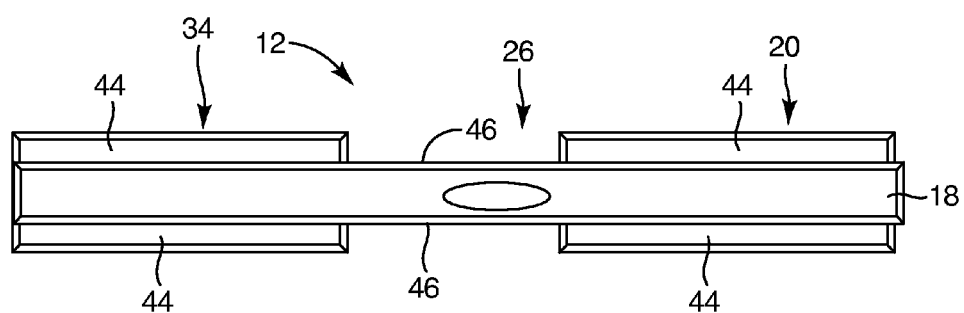
FIGS. 2C-2E each illustrates a top plan view of representative embodiments of the clam-shell cast.
Figure 2D:
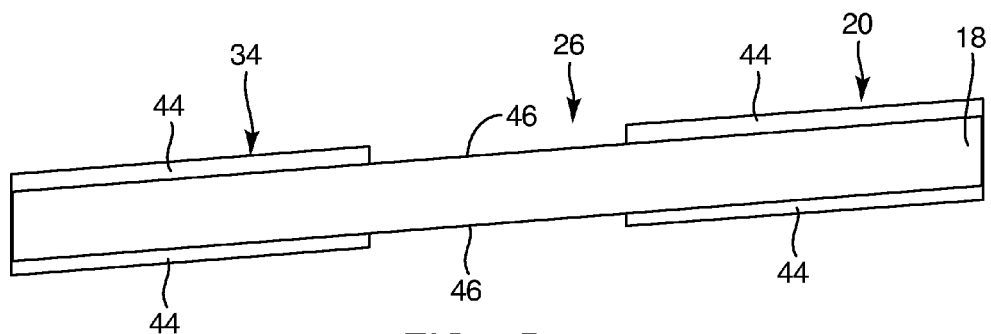
Figure 2E:
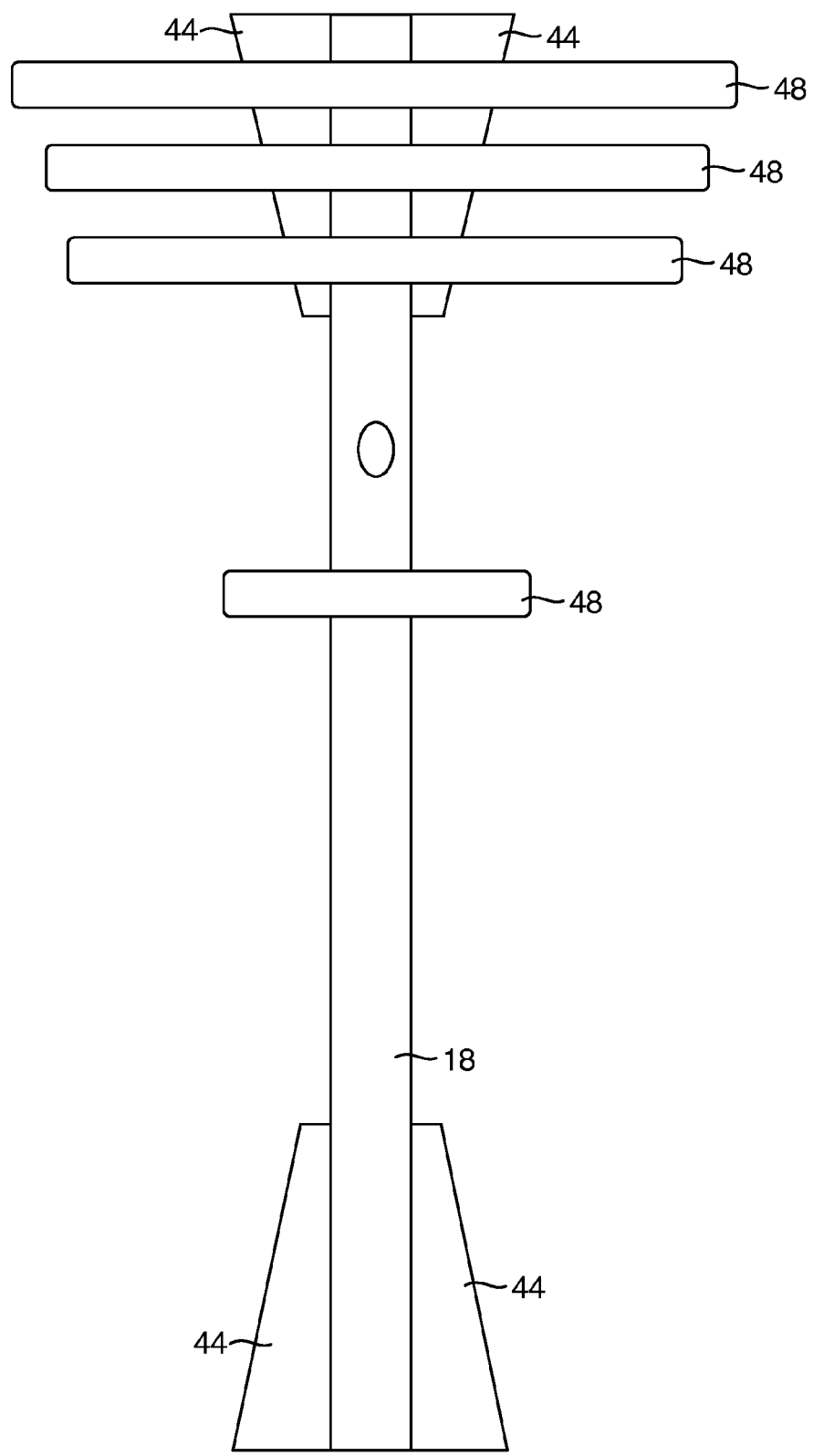

The cast 12 can comprise any suitable number of wings 44 (e.g., 1, 2, 3, 4, 5, 6, or more) that extend laterally from, or past, at least one lateral edge of the elongated casting material 18. For instance, returning to FIG. 2A, that figure shows an embodiment in which the cast 12 comprises 4 wings 44 that each extend laterally (on either side of the cast) past a lateral edge 46 of a portion of the elongated casting material 18.

Where the cast 12 comprises one or more wings 44, the wings can be disposed in any suitable location that allows a portion of the wings to extend (e.g., before the cast is hardened on a patient) laterally past a lateral edge 46 of the elongated casting material 18. Some examples of suitable locations include, but are not limited to, either side (e.g., a right and/or left side) of the first portion 20, second portion 26, and/or third portion 34 of the elongated casting material. By way of non-limiting illustration, FIGS. 2A, 2C, and 2D show some embodiments in which a plurality of wings 44 extend past a lateral edge 46 (on both a right-hand and a left-hand side) of both the first portion 20 and the third portion 34 of the elongated casting material 18.

Where the cast 12 comprises one or more wings 44, the wings can have any suitable shape that allows them to act as described herein. Some examples of suitable wing shapes include, without limitation, a fletch or fin shape (e.g., as shown in FIG. 2A), a rectangular or quadrilateral shape (e.g., as shown in FIGS. 2C and 2D), a trapezoidal shape (e.g., as shown in FIG. 2E), a polygonal shape, a triangular shape, an ovular shape, an irregular shape, and/or any other shape that allows the wing to function as intended.

Figure 3A:
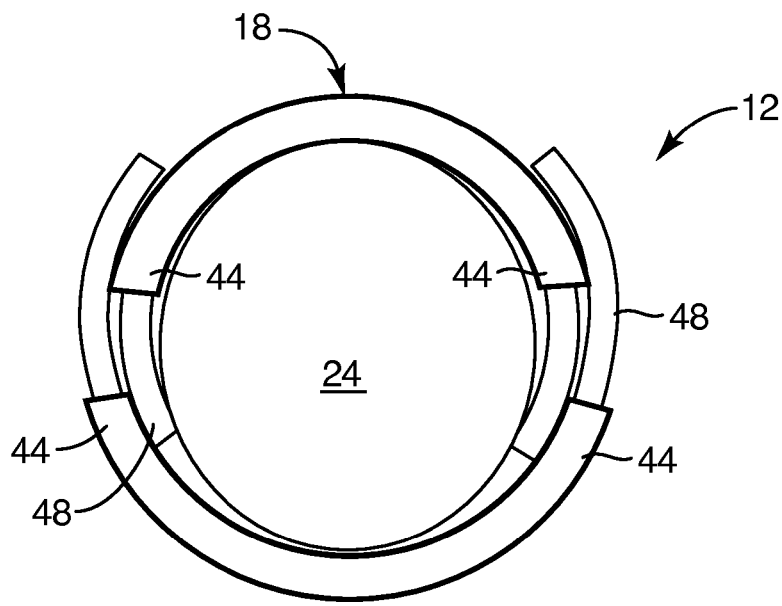
FIGS. 3A-3B each illustrates a top plan view of representative embodiments of the clam-shell cast in an assembled (or a substantially-assembled) position.
Figure 3B:
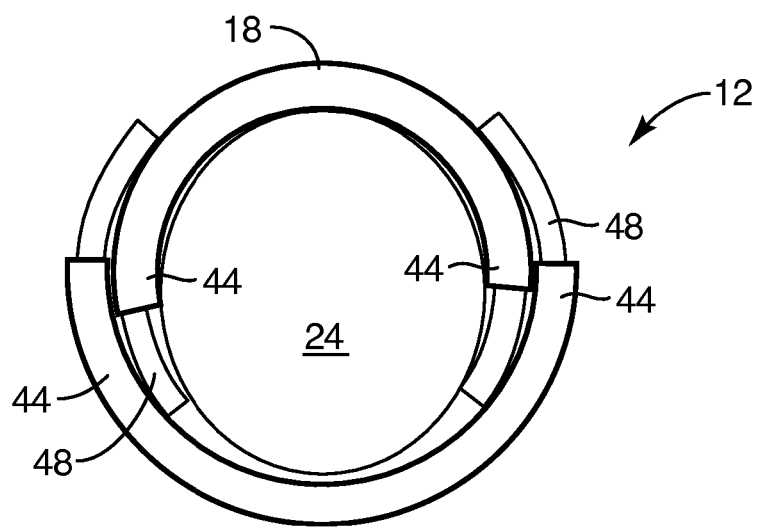

The wings 44 can also be any suitable length (or width) that allows them to function as intended. In some embodiments, one or more wings are configured to overlap at least one of another wing and a portion of the elongated casting material 18. For instance, FIG. 3A illustrates an embodiment in which the elongated casting material 18 and the wings 44 from the first portion 20 of the cast 12 are not necessarily configured to overlap with either the elongated casting material or another wing when the cast is worn on a lower leg 24 of a desired size. In contrast, FIG. 3B illustrates an embodiment in which the elongated casting material 18 and/or the wings 44 are configured to overlap at least one of another wing and the elongated casting material when worn on a lower leg 24 of a desired size. Specifically, FIG. 3B illustrates an embodiment in which at least one wing 44 overlaps another wing 44.

Where the cast 12 comprises a strap, the cast can comprise any suitable number of straps, including, 1, 2, 3, 4, 5, 6, 7, 8, 9, 10, 11, 12, or more. Additionally, the straps can be disposed in any suitable location (e.g., extending from either or both lateral sides of the first portion 20, the second portion 26, and/or the third portion 34). In this regard, FIGS. 4A-4C show various embodiments in which the cast 12 comprises one or more straps 48 that are disposed at the first portion 20 of the elongated casting material 18 with one or more foot straps 50 disposed at the second portion 26 of the elongated casting material 18. Additionally, FIG. 4C shows that, in at least some embodiments, the cast 12 comprises one or more straps 48 that are disposed at the third portion 34 of the elongated casting material 18. Furthermore, while the straps can overlap each other, be separated from each other, and/or have any other suitable relationship to each other, FIGS. 4A-4C illustrate that, in some embodiments, the straps 48 and/or 50 can be placed any suitable distance apart from each other that allows the cast 12 to function as intended.

Figure 5A:
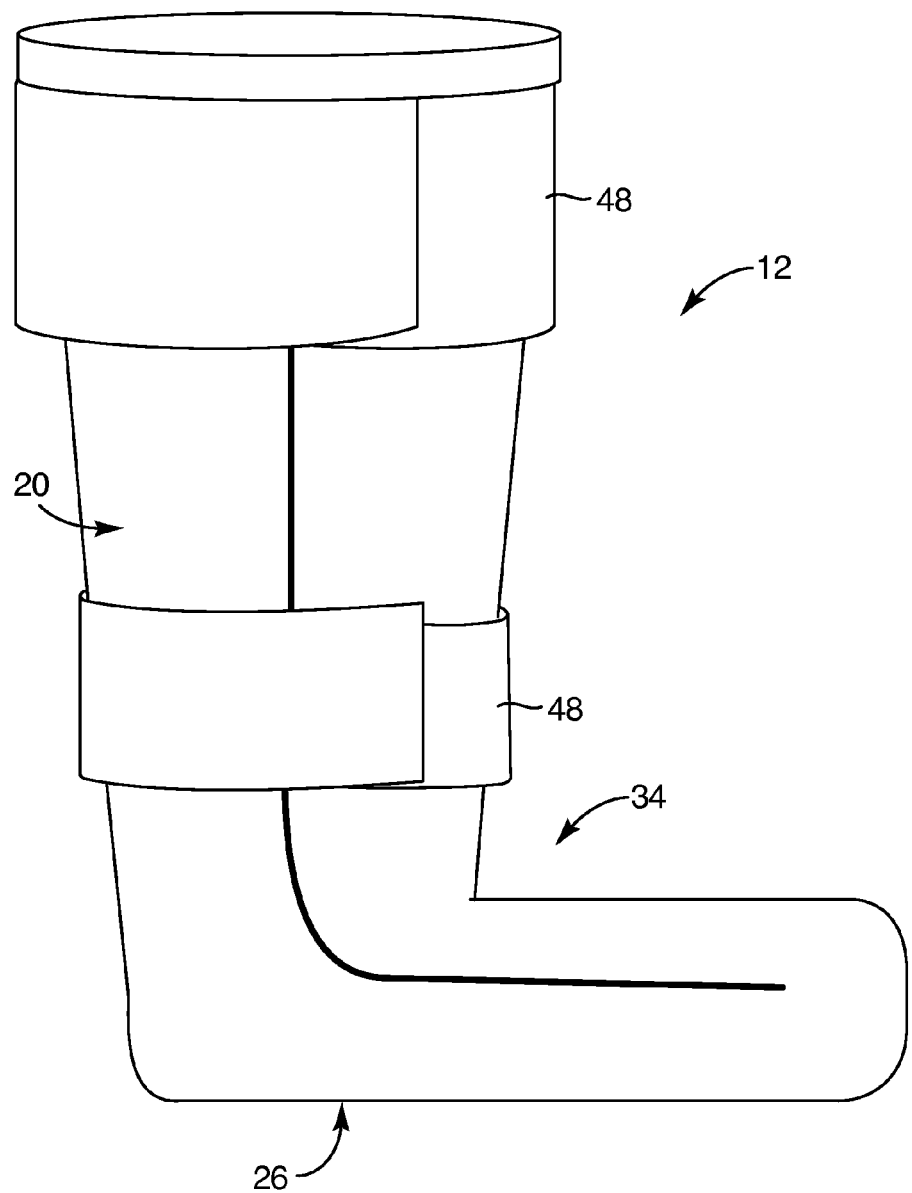
FIGS. 5A-5C each illustrates a side elevation view of representative embodiments of the clam-shell cast in the assembled position.
Figure 5B:
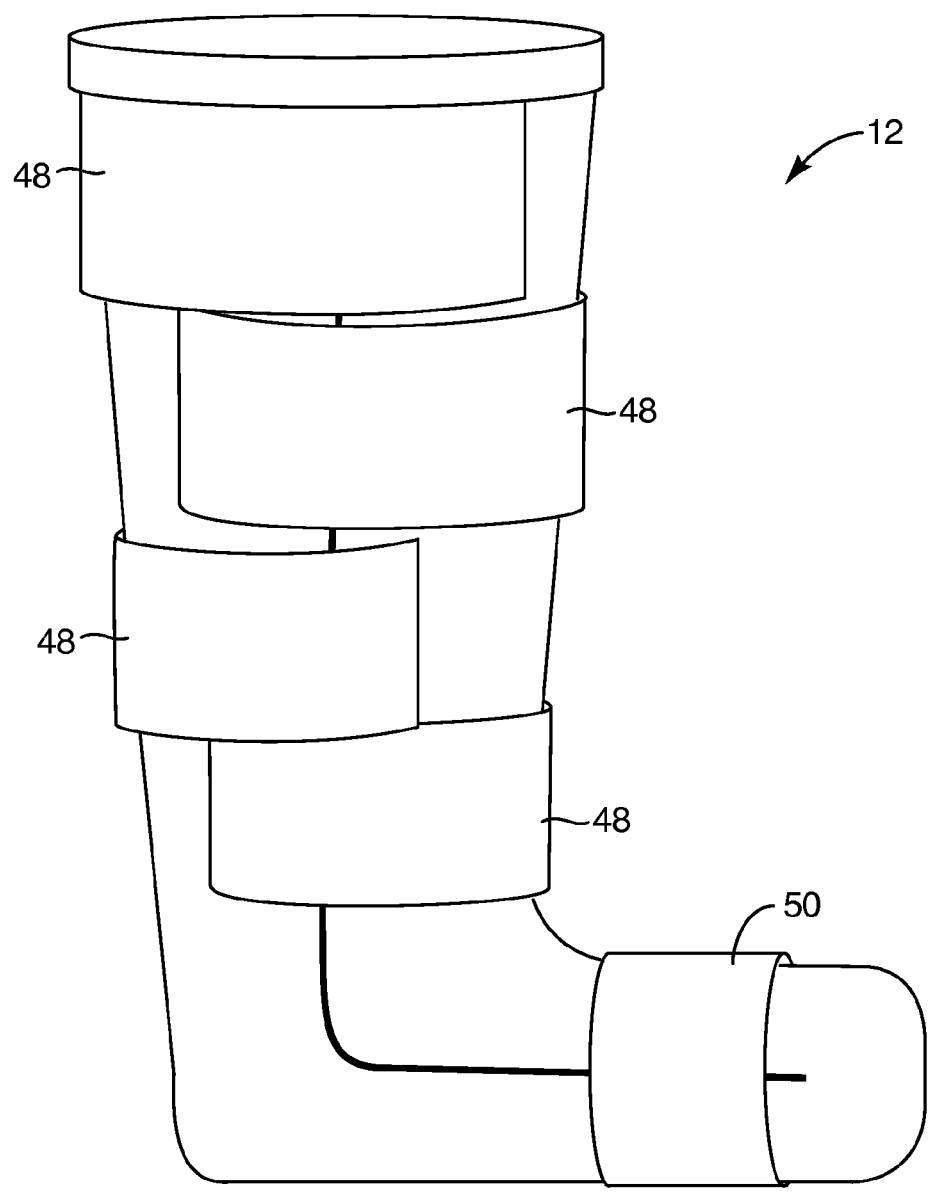
Figure 5C:
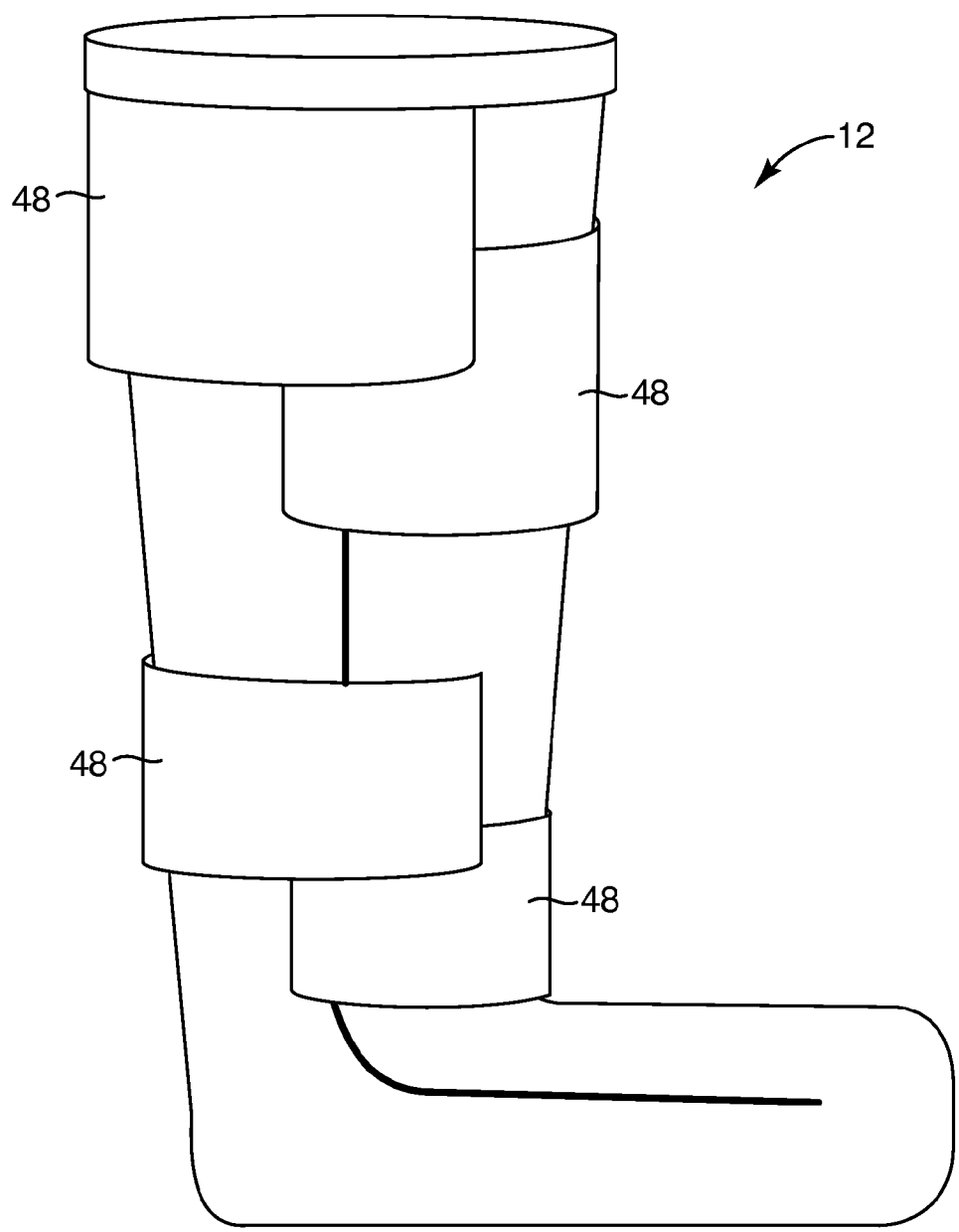

While the straps 48 can have any suitable shape (e.g., be rectangular, belt-shaped, triangular, rounded, polygonal, irregular, symmetrical, asymmetrical, ribbon-like, cord-like, rope-like, and/or any other suitable shape), FIG. 4B shows an embodiment in which at least some of the straps 48 are substantially rectangular. In this regard, while the strap ends can be any suitable shape (e.g., pointed, rounded, polygonal, irregular, triangular, trapezoidal, tapered, etc.), FIG. 4C shows a representative embodiment in which the strap ends 52 are substantially trapezoidal in shape.

Where the cast 12 comprises one or more straps 48, the straps can be configured to secure the cast on an appendage (e.g., lower leg 24) and/or any other suitable body part, in any suitable manner. For instance, FIG. 5A shows an embodiment in which one or more straps 48 are configured to circumscribe a portion of the cast 12. Additionally, FIG. 5B shows an embodiment in which at least some of the straps 48 are configured to extend only partially around a part of the cast 12. Moreover, FIG. 5C illustrates that, in some embodiments, a plurality of the straps 48 are configured to interdigitate with each other (e.g., by angling the straps across a portion of the elongated casting material 18). Furthermore, while the straps can run substantially perpendicular to a length (or a longitudinal axis) of the elongated casting material 18 (e.g., as shown FIG. 4C), in some embodiments, the straps are configured to run at an angle (e.g., an oblique and/or an obtuse angle) with respect to the length of the elongated casting material. In some embodiments, as the straps are configured to be wrapped perpendicularly (and/or at another suitable angle) to the length of the elongated casting material, this "cross-strapping" both secures the cast to an appendage and significantly increases the cast's strength.

Figure 6A:
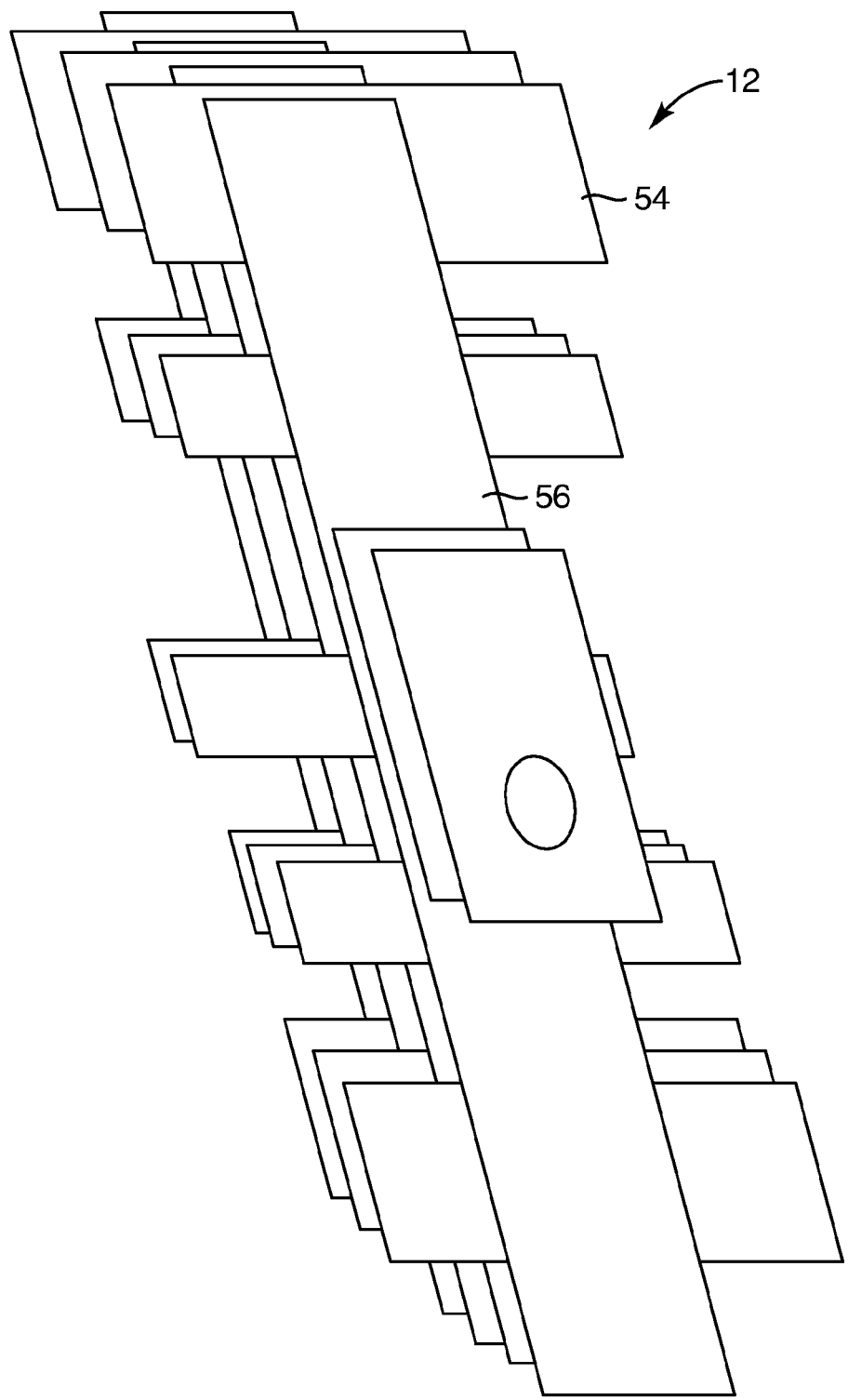
FIG. 6A illustrates a top, exploded view of a representative embodiment of the clam-shell cast.
Figure 6B:
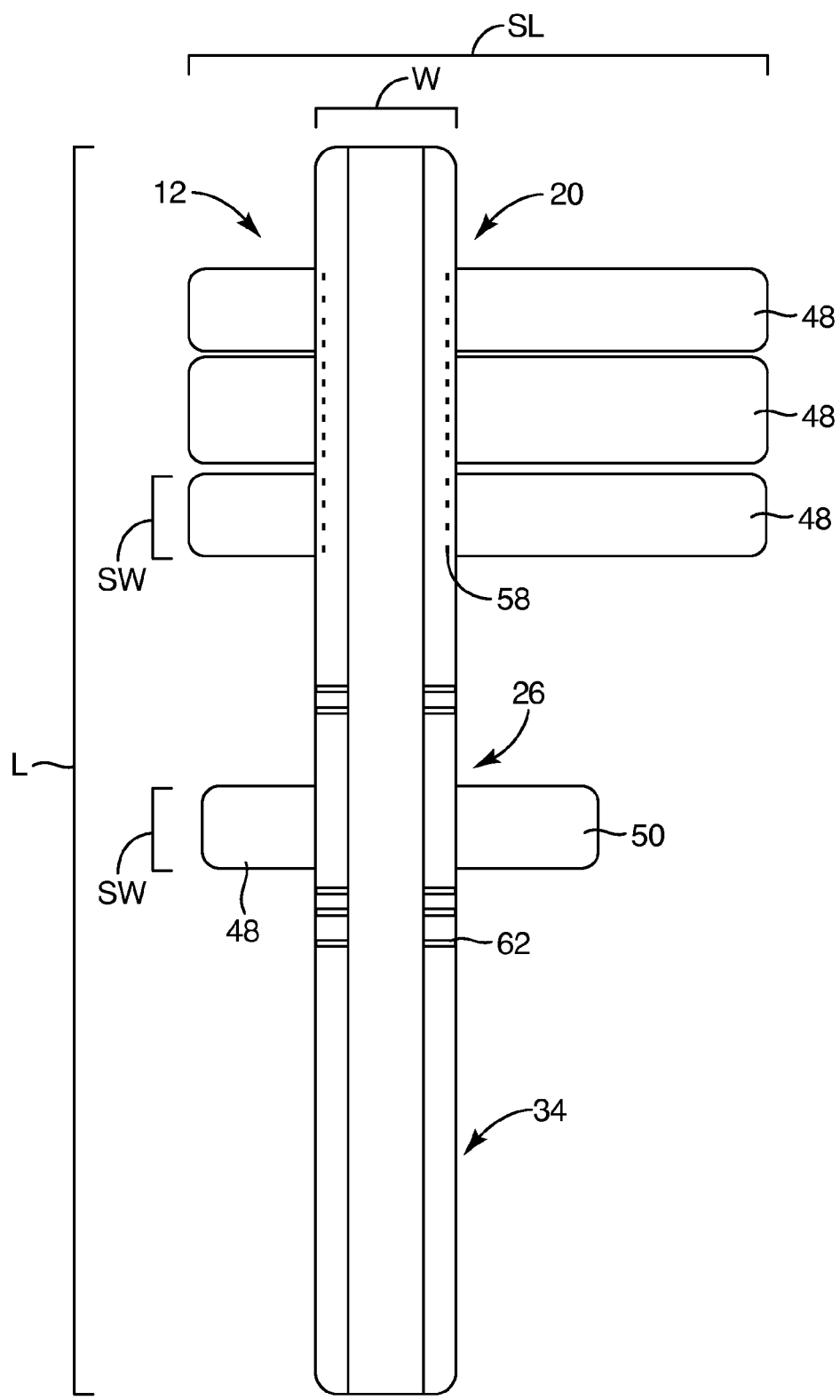
FIG. 6B illustrates a top plan view of a representative embodiment of the clam-shell cast.
Figure 6C:
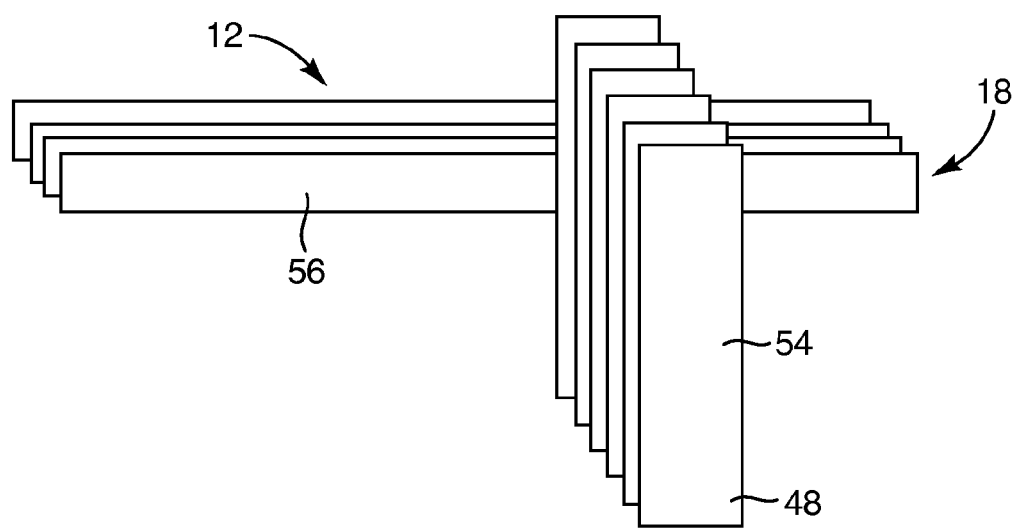
FIG. 6C illustrates a top, exploded view of a representative embodiment of the clam-shell cast.

The straps 48 and wings 44 can be made of any suitable material that allows the cast 12 to function as intended. Some examples of such materials include, but are not limited to, one or more hardenable casting materials, fabrics, materials comprising hook and loop fasteners, and/or any other suitable materials. In some embodiments, however, the straps and/or wings comprise a hardenable casting material (e.g., a fiberglass impregnated with polyurethane and/or any other new or novel hardenable material configured to be used with fiberglass casting materials).

Where the cast 12 comprises one or more straps 48, wings 52, and/or any other suitable connectors, such components can be attached to any suitable portion of the elongated casting material 18 (e.g., the first length 20, the second length 26, the third length 34, and/or any other suitable portion) and in any suitable manner. In this regard, some examples of suitable methods for attaching one or more connectors (e.g., straps and/or wings) to the cast include, but are not limited to, attaching such connectors to the cast by forming the cast and connector(s) together; by forming the cast and connector(s) of the same piece and/or pieces of material; via one or more adhesives, tapes, types of stitching, mechanical fasteners, non-mechanical fasteners, frictional fasteners, etc.; by tightening the connector(s) onto the cast; by wrapping the connector(s) around a portion of the cast; by passing the connector(s) through one or more loops on the cast; and/or any other suitable method). Indeed, FIG. 6A shows that, in some embodiments, one or more pieces of strap material 54 are inserted between two or more layers 56 of the elongated casting material 18. In contrast, FIG. 6B shows straps 48 can be attached to the elongated casting material via stitching 58 and/or one or more other suitable manners. In still another example, FIG. 6C shows that, in some embodiments, one or more pieces of strap material 54 are placed on top of and are adhered or otherwise attached to (e.g., via stitching and/or any other suitable method) to one or more layers 56 of the elongated casting material 18.

The various components of the cast 12 (e.g., the elongated casting material 18, the wings 44, and/or straps 48) can be any suitable size. Indeed, while the elongated casting material can be any suitable width, in some embodiments, it has a width (e.g., width W as shown in FIG. 6B) that is between about 4 cm and about 40 cm, or any sub-range thereof (e.g., between about 15 cm and about 20 cm). Additionally, while the elongated casting material can be any suitable length (e.g., length L as shown in FIG. 6B), in some embodiments, it has a length between about 50 cm and about 255 cm, or any sub-range thereof (e.g., between about 127 cm and about 158 cm). Moreover, while the straps can be any suitable width (e.g., strap width SW, as shown in FIG. 6B), in some embodiments, the straps have a width between about 0.5 cm and about 35 cm, or any sub-range thereof (e.g., between about 5 cm and about 13 cm). Furthermore, while the straps can be any suitable length (e.g., strap length SL, as shown in FIG. 6B), in some embodiments, the straps have a length between about 20 cm and about 90 cm, or between any sub-range thereof (e.g., between about 35 cm and about 76 cm).

The various components of the cast 12 can also have any suitable thickness. Indeed, in some embodiments, the elongated casting material 18, straps 48, and wings 44 are between about 1 mm and about 3 cm thick. In other embodiments, the various components of the cast have a thickness that falls in any suitable sub-range of the aforementioned range (e.g., between about 2 mm and about 4 mm thick). Moreover, although, in some embodiments, the wings and/or straps have a thickness that is substantially equal to or greater than the thickness of the elongated casting material, in other embodiments, the wings and/or straps have a thickness that is thinner than that of the elongated casting material. Indeed, in some embodiments, the wings and/or straps have a thickness that is between: about 1% and about 99%, or between any sub-range of such range (e.g., between about 20% and about 70% or between about 40% and about 60%) of the thickness of the elongated casting material.

The various components of the cast 12 can comprise any suitable number of layers of hardenable casting materials. Indeed, in some embodiments, the various cast components (e.g., the elongated casting material 18, the wings 44, and/or straps 48) comprise between about 1 and about 30 layers of hardenable casting material (e.g., fiberglass knitting). In other embodiments, the various components comprise between about 2 and about 16 layers of casting material. In still other embodiments, the various components comprise any suitable number of layers of casting material that fall within any of the aforementioned ranges. For instance, some embodiments of the elongated casting material 18 comprise between about 12 and about 17 layers of casting material (e.g., from 14 to 16 layers). Additionally, some embodiments of the straps comprise between about 3 and about 7 layers of casting material (e.g., from 4 to 6 layers).

Figure 7A:
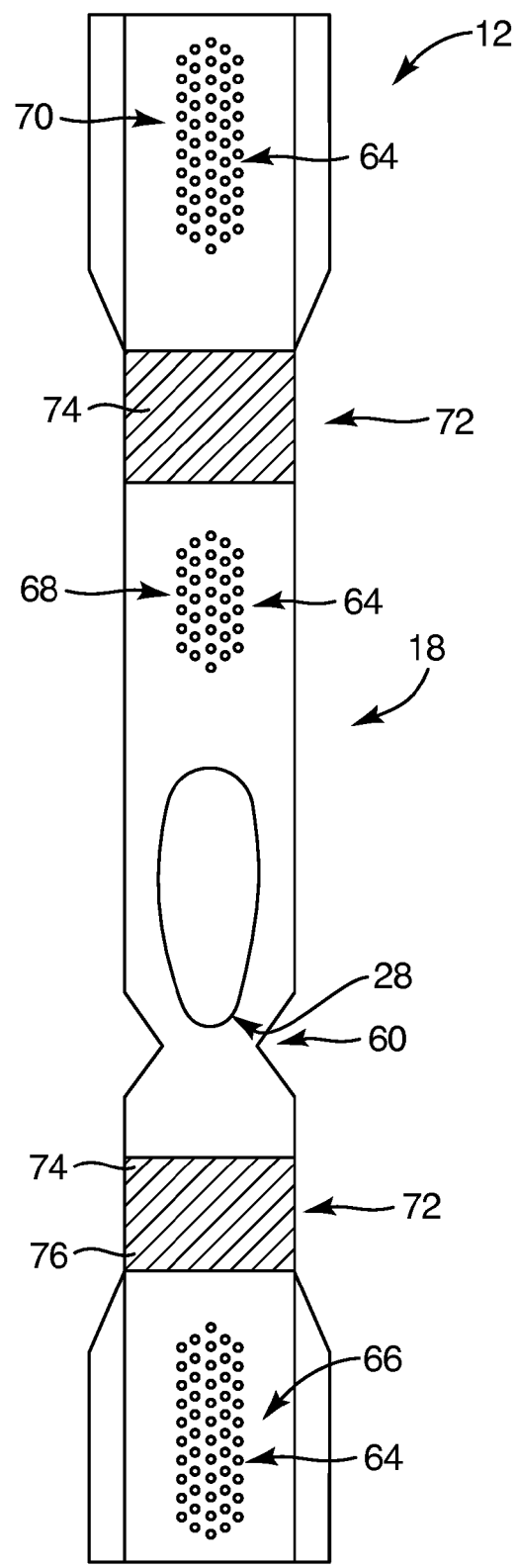
FIG. 7A illustrates a top plan view of a representative embodiment of the clam-shell cast.

In addition to the aforementioned characteristics, the clam-shell cast 12 can be modified in any suitable manner that allows it to protect and/or offload weight from a portion of a patient's body. In one example of a suitable modification, some embodiments of the elongated casting material 18 comprise one or more features that allow it to bend relatively easily (e.g., before the cast hardens) in one or more places (e.g., around a patient's heel, toes, etc.). In this regard, the cast can be configured to bend in any suitable manner, including, without limitation, by including one or more cuts, notches, perforations, scored portions, pre-creased fold lines, hinges, thinned portions, and/or other similar features (which may be referred to herein as a folding accommodation) in a location where it is intended that the elongated casting material will bend to conform to an appendage. By way of illustration, FIG. 7A shows an embodiment in which the elongated casting material 18 includes at least one notch 60 that extends into the elongated casting material at a place where the elongated casting material is configured to bend around a patient's heel 28. In another example, FIG. 4B shows an embodiment in which the cast 12 comprises one or more cuts 62 that extend towards a center of the elongated casting material 18, where the elongated casting material is configured to bend around the patient's heel and toes.

In another example of an optional modification, some embodiments of the cast 12 define one or more holes (e.g., holes to provide ventilation and/or holes for medical tubing; collectively and individually referred to as ventilation holes or holes). In this regard, the cast can define any suitable number of ventilation holes, the holes can be of any suitable size, and the holes can be disposed in any suitable location. In one example, the cast comprises between 1 and 10,000 holes, or any suitable number of holes that fall within that range (e.g., between 1 and 200).

While the ventilation holes in the cast 12 can be any suitable size that allows air and/or medical tubing (e.g., for negative pressure wound therapy or another suitable purpose) to pass through the casting material while allowing the cast to maintain a desired rigidity, in some embodiments the holes have an inner diameter or width of between about 1 mm and about 20 cm. In other embodiments, the cast defines one or more holes having an inner diameter or width between about 0.3 cm and about 3 cm. In still other embodiments, the cast defines one or more holes in any suitable sub-range of the aforementioned ranges (e.g., between about 0.4 cm and about 2 cm).

While the ventilation holes can be disposed in the cast 12 in any suitable location (e.g., in the elongated piece of casting material 18, in one or more wings 44, in one or more straps 48, and/or in any other suitable location), in some embodiments, the holes are configured to be disposed in the cast so as to provide ventilation and/or access to medical tubing to a calf, sole of a foot, dorsal portion of a foot, heel, shin, and/or other portion of an appendage. By way of illustration, FIGS. 7A and 7B show some embodiments in which the cast 12 comprises ventilation holes 64 in a calf section 66, dorsal foot section 68, and shin section 70 of the cast 12.

In another example of a suitable modification, some embodiments of the cast 12 comprise or are configured to comprise one or more reinforced portions. In such embodiments, any suitable portion of the cast can be reinforced (e.g., a toe, foot, ankle, calf, proximal portion, etc.). By way of non-limiting illustration, FIGS. 7A-7B show some embodiments in which an ankle portion 72 of the cast 12 comprises a reinforcement 74. In any case, however, reinforcement of portions of the cast can be provided in any suitable manner. Indeed, in one example, after the cast is placed on an appendage a strap, ribbon, tie, and/or belt is placed on one or more portions of the cast. In another example, after the cast is placed on an appendage, casting material is wrapped around the cast in a desired location. In still another example, one or more reinforcements are added to the cast by placing additional layers 76 of casting material (as shown in FIGS. 7B-7C) in desired locations along a length of the elongated casting material 18 (e.g., before and/or after the cast is fit to a patient).

Figure 7B:
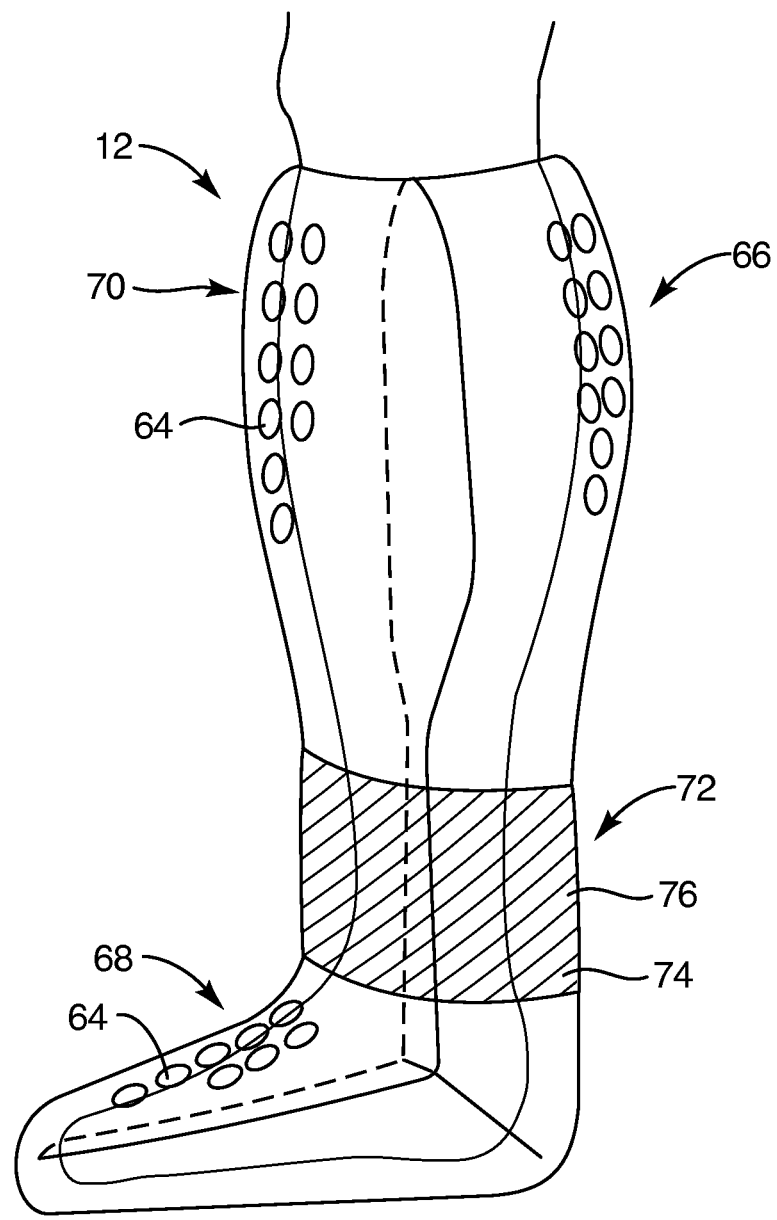
FIG. 7B illustrates a side elevation view of a representative embodiment of the clam-shell cast disposed on the patient.
Figure 7C:
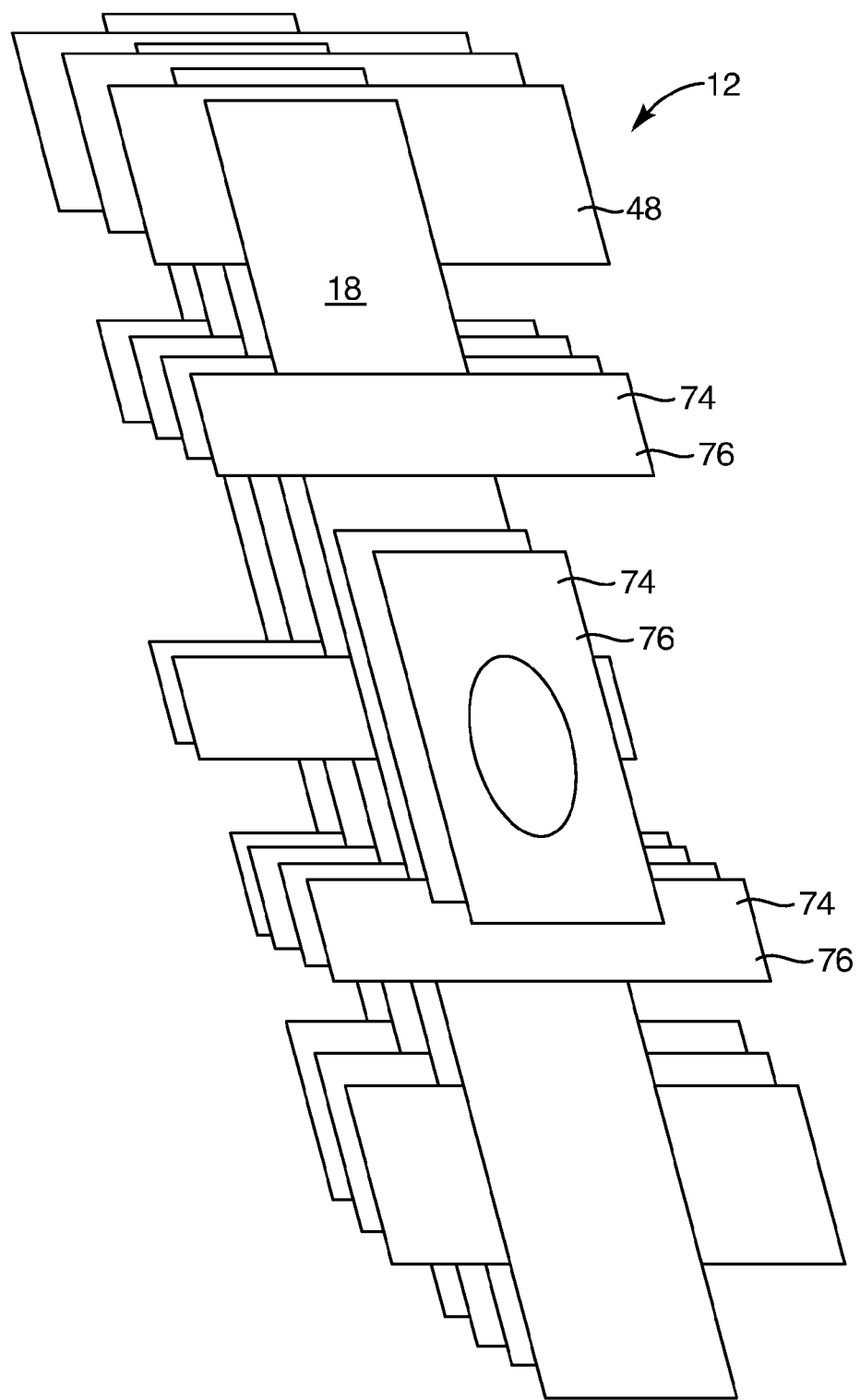
FIG. 7C illustrates a top, exploded view of a representative embodiment of the clam-shell cast.

In another example of a suitable modification (which is not shown), instead of being configured to extend directly over the shin and calf of a patient (e.g., as shown in FIG. 7B), the elongated casting material 18 is configured to run down a lateral portion of a patient's lower leg, wrap over a portion of the patient's foot (e.g., heel 28 and/or another suitable portion), and extend back up over a medial portion of the patient's lower leg (or vice versa).

In still another example of a suitable modification (which is not shown), the cast 12 is configured to extend over one or more other appendages of a patient (e.g., an arm, finger, torso, etc.). Indeed, in some embodiments, the cast is configured to extend over a posterior portion of a patient's forearm, wrap over a distal end of the patient's hand (e.g., over the distal end of the patient's fingers and/or with one or more of the patient's fingers extending through a corresponding hole or holes in the casting material), and to extend over an anterior portion of a patient's forearm.

In yet another example of a suitable modification, in some embodiments, the elongated casting material 18 is formed (at least partially) into a preformed boot before being applied to a patient's lower leg. In some such embodiments, the elongated casting material comprises a hardenable casting material (e.g., a thermoplastic casting material, a plaster casting material, a fiberglass casting material, etc.) that can be softened (e.g., via application of heat, water, a solvent, and/or other suitable element or process) to be conformed to the shape of the patient's lower leg, and that can then be hardened to form an orthopedic cast.

Figure 8:
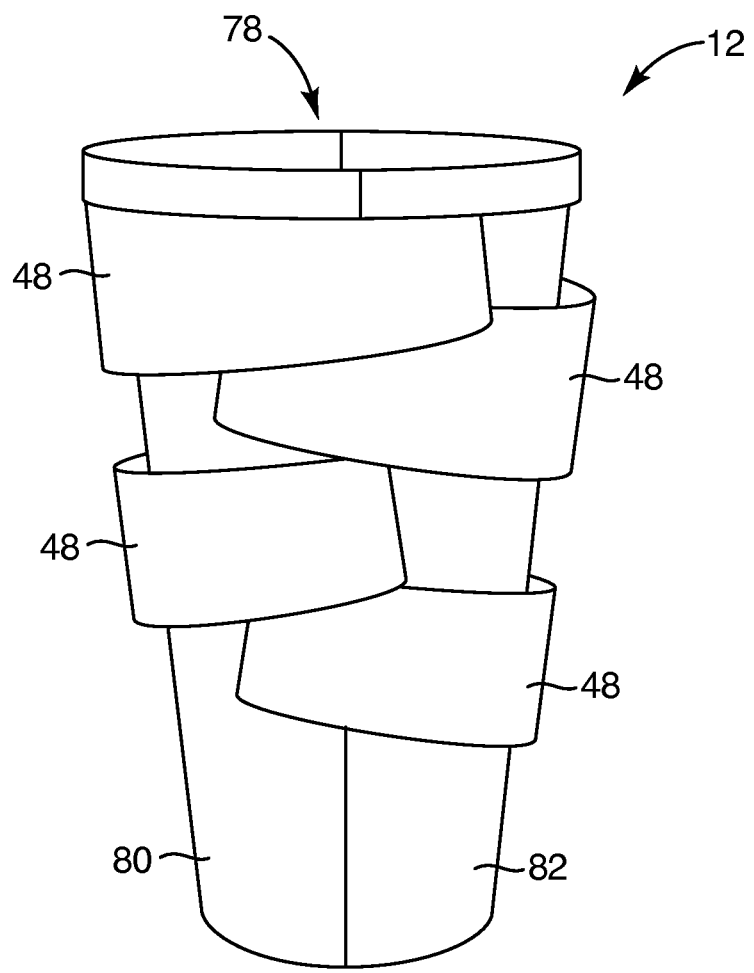
FIG. 8 illustrates a side elevation view depicting a representative embodiment of the clam-shell cast.

In even another example of a suitable modification, while some embodiments of the elongated casting material comprise a single continuous strip of material that extends from a first surface of an appendage (e.g., a calf), around an end of the appendage (e.g., a heel), and over a second surface (e.g., shin) of the appendage, which is substantially opposite to the first surface, some embodiments of the cast comprise two or more separate pieces that are configured to be molded and/or hardened over opposing surfaces of an appendage (e.g., over a calf and a shin, an anterior and posterior portion of a forearm, etc.). By way of illustration, FIG. 8 depicts an embodiment in which the cast 12 comprises a splint 78 that includes a first 80 and a second portion 82 of hardenable casting material that are joined by at least one strap 48. In this regard, while FIG. 8 shows that, in some embodiments, the first 80 and second 82 portions of the casting material abut each other, in some other embodiments (similar to the discussion above relating to FIGS. 3A and 3B), the first and/or second portions of the casting material overlap each other (or stop short of overlapping with each other) when placed on a desired appendage. Additionally, while FIG. 8 shows an embodiment in which the splint comprises a first 80 and a second 82 discrete portion, the splint can comprise any suitable number of pieces, including, without limitation, 1, 2, 3, 4, 5, 6, or more. Indeed, in some embodiments, the splint comprises a single piece of the elongated casting material, with one or more wings, straps, and/or portions of the casting material overlapping and/or configured to overlap another portion of the elongated casting material when it is applied to an appendage.

In another example, some embodiments of the described cast 12 comprise both a hardenable casting material (e.g., that can be formed around a portion of an appendage, such as a sole of a foot) and another material (e.g., one or more plastics, vulcanized rubbers, metals, polymers, wood, ceramics, and/or other materials) forming part of a preformed cast. In some such embodiments, the various materials can be connected with each other in any suitable manner, including, without limitation, through the use of one or more straps, hinges, types of stitching, mechanical fasteners, adhesives, tapes, frictional engagements, and/or any other suitable connectors. While such a cast can perform any suitable functions, in some embodiments, the preformed portions of the cast allow the cast to be placed on a patient relatively quickly, while the portions formed from a hardenable casting material allow the cast to be tailored to fit a patient and to thereby spread weight across a portion of the cast to offload weight from a wound covered by the cast.

In another example, the cast 12 can comprise (or otherwise be used with) a cast walker; a walking heal; a walking pedestal; a walking shoe; one or more reinforcements (e.g., one or more pieces of metal, plastic, ceramic, wood, rubber, and/or other suitable material) in a foot portion of the cast; an orthopedic insert; a footplate; a cast boot, slipper, shoe, sandal, slide, and/or other footwear comprising a footplate; and/or any other suitable structure that allows a patient to walk on a lower leg that is covered with the cast.

In another example, the described cast 12 is configured to be walked on and/or otherwise used without the use of a boot 18, shoe, and/or footplate (as discussed below). In such embodiments, the cast can be configured in any suitable manner that allows it to be used without a boot, shoe, or footplate, including, without limitation, by be made with a casting material and/or a sufficient amount of the casting material that prevents the cast from breaking and/or unduly bending during use. In other embodiments, as discussed above, the cast comprises one or more reinforcements in one or more portions of the cast (e.g., a foot portion, an ankle portion, etc.).

In even another example, some embodiments of the cast 12 do not include the use of casting material that is spiraled along an appendage and the cast itself. In some other embodiments, however, after the elongated piece of hardenable casting material 18 is applied to an appendage, hardenable casting material (and/or any other material) is spirally wrapped around a portion (if not all of) the cast.

In still another example, while the cast 12 is described herein for use as a total contact cast (e.g., for use in the treatment of sores, ulcers, and/or any other suitable wound on a foot), the cast can be modified to be used for any other suitable purpose. Indeed, in some embodiments, the cast is configured to extend up a patient's leg, past the patient's knee. In other embodiments, the cast is used for protecting an appendage (e.g., leg, foot, toe, arm, hand, finger, etc.). with a broken and/or fractured bone, while the bone heals. In yet other embodiments, the cast is configured to be used in trauma situations in which a cast needs to be applied to a patient quickly. In yet other embodiments, the cast is used for: post-surgical applications, post-fracture applications, protection of macerated tissue, closed reduction, covering an incision, immobilization of an appendage, negative pressure wound therapy, and/or for any other suitable purpose.

In yet another example of a suitable modification, some embodiments of the casting material of the described cast 12 (e.g., those comprising one or more antibiotics, bactericides, silver, copper, nickel, iodine, and/or any other suitable antimicrobial material) are used to make any suitable known or novel cast, splint, and/or other protective casting. Indeed, in some embodiments, the described casting material comprising one or more antimicrobial materials is used to form an orthopedic cast in which fiberglass, cotton, and/or another suitable material is wrapped around a body part and hardened to form a cast.

In addition to the characteristics previously mentioned, the described clam-shell cast 12 can have several features. Indeed, as some embodiments of the clam-shell cast are configured to fold onto a first surface of an appendage, extend around an end of the appendage, and then fold back over a second surface of the appendage, which is substantially opposite to the first surface, some such embodiments of the described cast differ from some conventional casts in that the elongated casting material 18 of the current cast 12 is not spirally wound or wrapped around an appendage or rolled or slid on to the appendage as a sock, stockinette, or sleeve.

In another example, as some embodiments of the described cast 12 are configured to substantially conform to the shape of an appendage, some such embodiments can be relatively effective at spreading pressure across the appendage and thereby offloading weight from a wounded portion of the appendage.

In another example, as some embodiments of the described cast 12 have openings (e.g., on the sides of the toes, along the sides of the cast, via ventilation holes 104, via openings knitted and/or otherwise formed in the casting material, etc.), the described cast can allow for better ventilation than some competing casts. As a result, some embodiments of the described cast can manage moisture better than can some conventional casts. Accordingly, some embodiments of the described cast can better reduce the problems associated with uncontrolled moisture (e.g., maceration, soft tissue necrosis, etc.) than can some conventional casts.

In yet another example, some embodiments of the described cast 12 allow a patient wearing the cast to heal (e.g., have a foot wound heal) while still being able to walk. In another example, by wearing some embodiments of the described cast, a patient is able to keep undue pressure off a foot wound, even if the patient is not purposefully trying to do so. In even another example, some embodiments of the described cast are configured to eliminate and/or reduce the propulsive phase a patient's gate and/or shorten the patient's stride length, thus reducing the potentially damaging forces that can be placed on a wound as the patient walks.

In still another example (mentioned briefly above), some embodiments of the described cast 12 do not require that the cast (like some conventional total contact casts) be spirally wound around an appendage, or slid or rolled over the appendage like a sleeve, sock, or stockinette. As a result, some such embodiments of the described cast may be applied more quickly than some conventional total contact casts. Moreover, as some embodiments of the described cast can be applied to an appendage while the patient is sitting up or in another comfortable position, some embodiments of the cast can be applied more conveniently than some conventional total contact casts that require a patient to be moved onto the patient's belly or into another uncomfortable position.

Foot Support

With respect to the foot support 14, the foot support comprises an orthotic that can comprise any suitable characteristic or component that allows it to offload at least some weight from a foot wound and/or provide padding to a portion of a foot 32. While the foot support can be disposed in any suitable location, in some embodiments, the foot support is configured to be disposed between a patient's foot and an interior surface of a cast (e.g., the cast 12 and/or any other suitable known or novel cast).

Figure 9A:
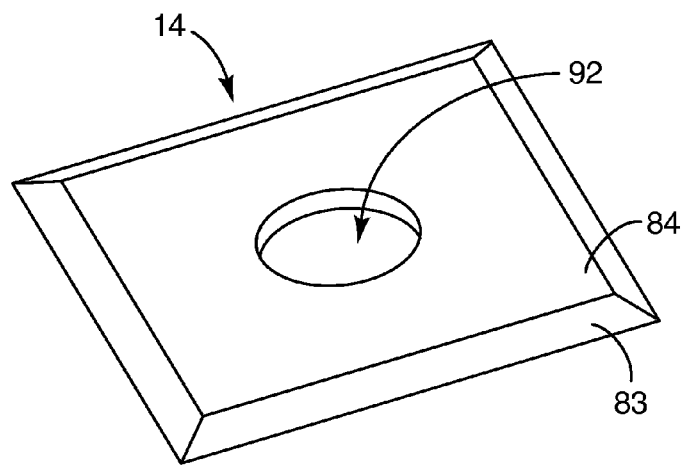
FIG. 9A illustrates a perspective view of a representative embodiment of a foot support.

The foot support 14 can be any suitable shape, including, but not limited to, being square, rectangular, polygonal, symmetrical, irregular, circular, elliptical, foot shaped, shaped to contour to a portion of a foot, the shape of a portion of a foot, and/or any other suitable shape that allows it to perform its intended function. In some embodiments, however, FIG. 9A shows the foot support 14 comprises a quadrilateral shape. In contrast, FIG. 9B shows that, in some other embodiments, the foot support 14 comprises an elongated quadrilateral shape.

Figure 9B:
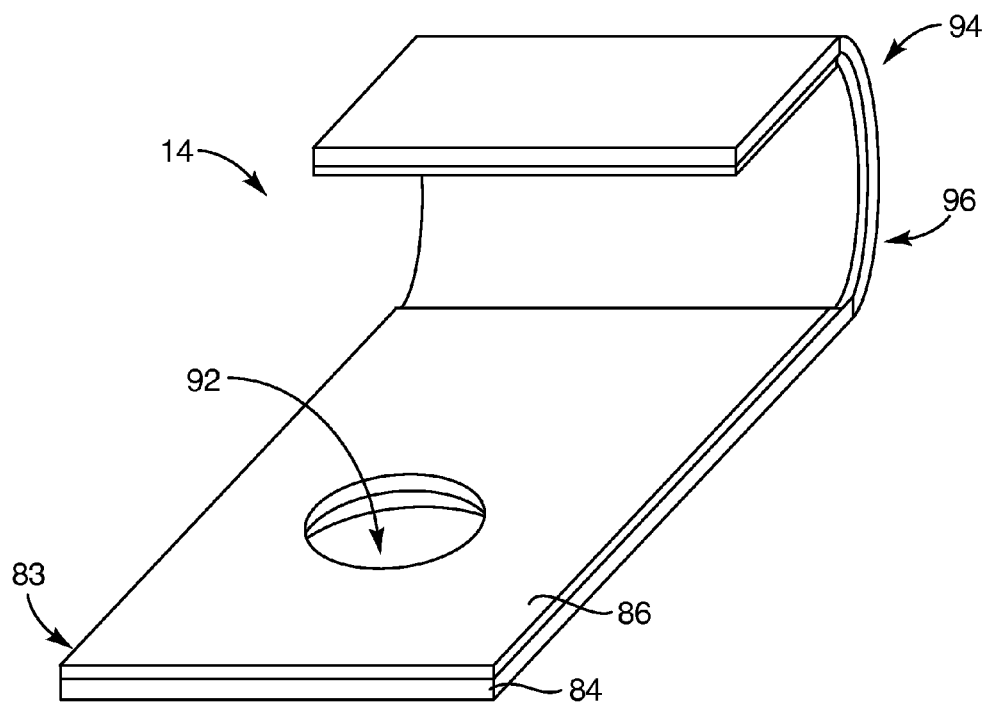
FIG. 9B illustrates a perspective view of the foot support according to a representative embodiment, wherein the foot support defines an offloading hole.
Figure 9C:
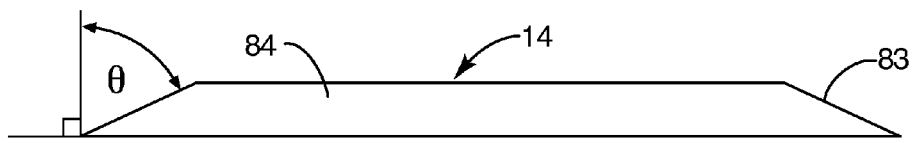
FIG. 9C illustrates a side elevation view of a representative embodiment of the foot support.

While the edges of the foot support 14 can have any suitable shape (e.g., terminating at a right angle, being rounded, being chamfered, tapering, being feathered, etc.), FIG. 9B shows an embodiment in which the at least some of the foot support's edges 83 end substantially at right angles. Additionally, FIGS. 9A and 9C show some embodiments in which the edges 83 of the foot support 14 are at least partially beveled. In such embodiments, the foot support's edges can be beveled at any suitable angle (e.g., at an angle θ, including, without limitation, at an angle between about 1° and about 89°, or within any sub-range thereof (e.g., between about 50° and about 70°, as shown in FIG. 9C).

The foot support 14 can comprise any suitable material that allows it to provide padding to and/or to otherwise support a portion of a patient's foot. In this regard, the foot support can comprise any suitable type of plastic, polymer, metal, ceramic, wood, synthetic material, natural material, padding, foam, anti-bacterial material (e.g., one or more bamboo materials, bamboo rayons, silver-coated poly(ethylene terephthalate), silver-coated rayon, silver-coated polyester, other silver-coated materials, iodine-incorporated materials, copper-coated materials, silver/copper-coated materials, silver/copper/nickel-coated materials, silver/copper/tin-coated materials, etc.), and/or other antimicrobial material (e.g., as discussed above) and other suitable material that allows it to perform its intended purpose. Where the foot support comprises padding, the foot support can comprise virtually any suitable type of padding, including, without limitation, closed cell padding, open cell padding, polymer padding (e.g., polypropylene, polyethylene, polyurethane, etc.), p-cell foam, x-static foam, felted foam, foam, polyurethane foam, silicon, gel, cotton, vinyl, polyvinyl chloride, ethylene vinyl acetate, cork, combinations thereof, and any other suitable material. Indeed, in some embodiments, the padding material comprises p-cell foam and/or crepe foam, wherein at least one of the foams is optionally covered with felt and/or another suitable material.

Figure 9D:
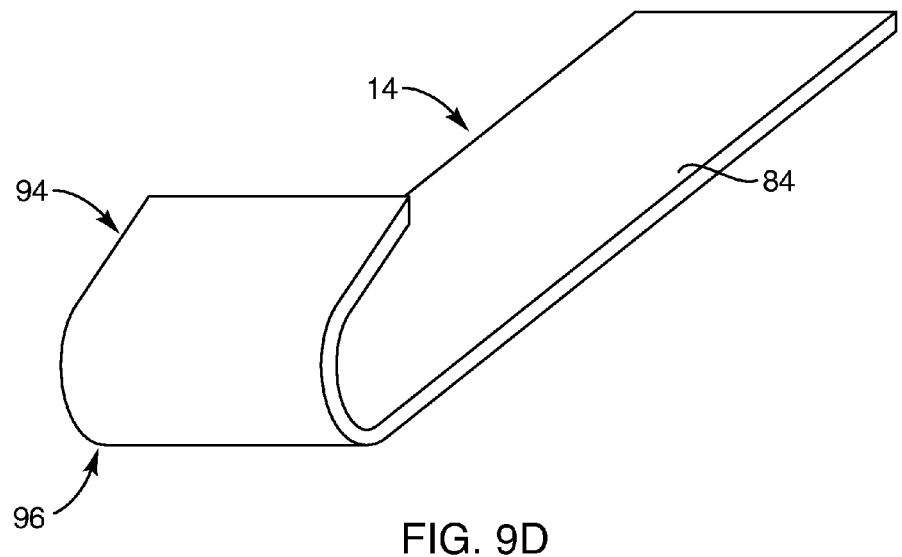
FIG. 9D illustrates a perspective view of a representative embodiment of the foot support.
Figure 9E:
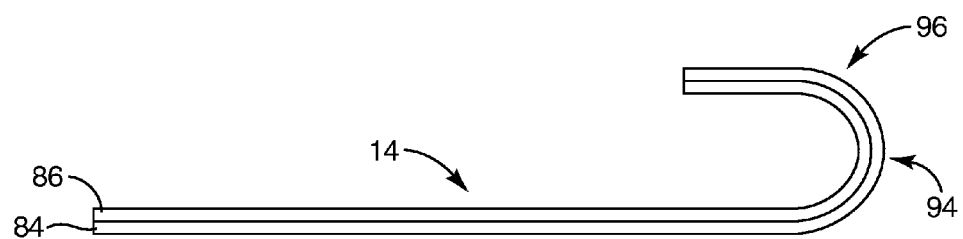
FIG. 9E illustrates a side elevation view depicting a representative embodiment of the foot support.
Figure 9F:
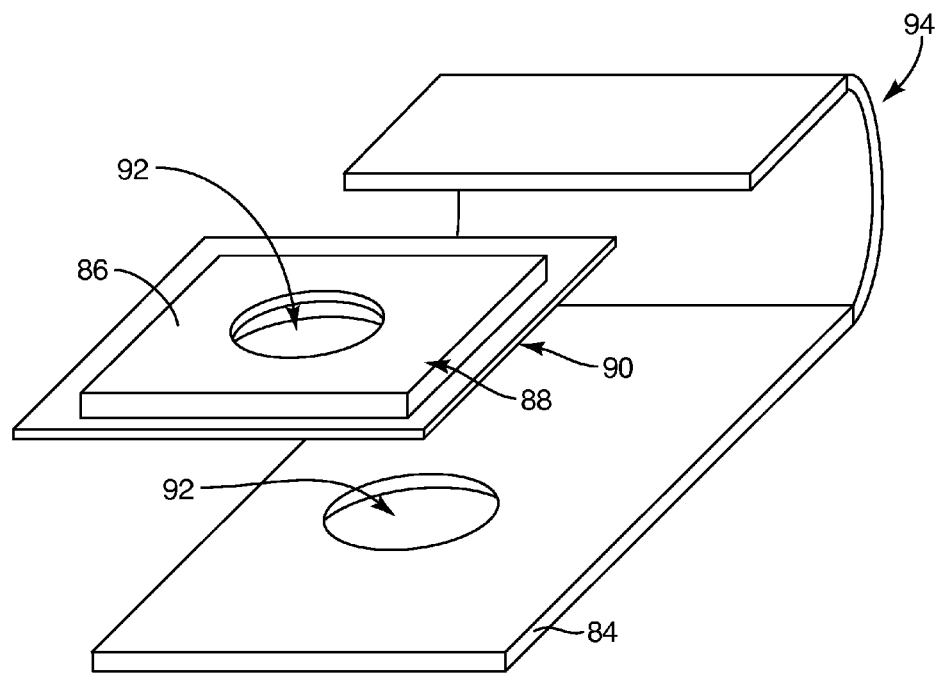
FIG. 9F illustrates a perspective view of a representative embodiment of the foot support.
Figure 9G:
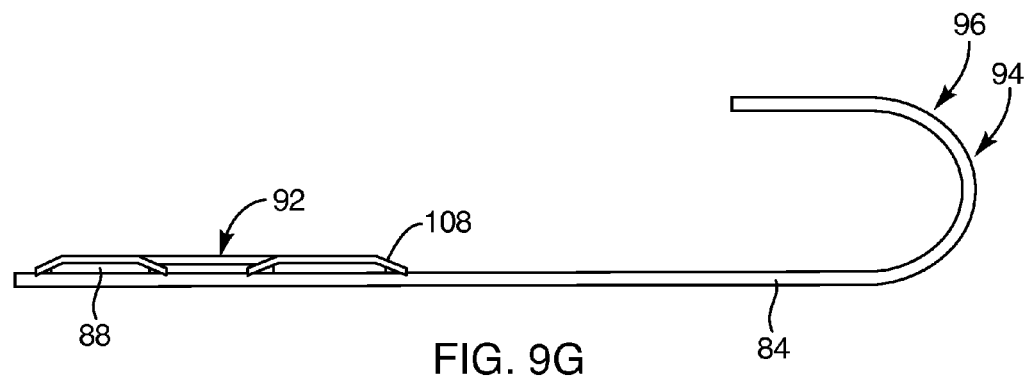
FIG. 9G illustrates a side cross-sectional view of the foot support in accordance with a representative embodiment.

Although some embodiments of the foot support 14 comprise a single type or layer of padding material, in other embodiments, the foot support comprises a plurality of padding materials (e.g., 2, 3, 4, 5, or more). In such embodiments, the padding materials can be disposed in any suitable manner (including, without limitation, by having some of the padding materials be localized to particular locations (e.g., pressure points) on a foot and/or having the various padding materials be disposed in layers). In this regard, FIGS. 9C and 9D show some embodiments in which the foot support 14 comprises a first padding layer 84. In contrast, FIGS. 9E-9G show some embodiments in which the foot support 14 comprises the first padding layer 84 and a second padding layer 86, wherein both layers extend across a significant portion, if not all, of the foot support. FIGS. 9F and 9G, however, show some embodiments in which the foot support 14 comprises the first padding layer 84 (e.g., a crepe padding) with one or more additional layers (e.g., of a p-cell foam 88 and/or another foam 90), localized around an offloading hole or recess 92 (hereinafter referred to as a hole or an offloading hole).

Where the foot support 14 comprises multiple layers of padding materials, the various padding layers can have any suitable characteristic. For instance, where the foot support 14 comprises multiple layers of padding, the various layers can be joined in any suitable manner, including, without limitation, by being integrally formed together, via an adhesive, with a tape, through a hook and loop fastener, via heat welding, through stitching, and/or any other suitable manner.

While various portions of the foot support 14 can be malleable, semi-malleable, and/or non-malleable, in some embodiments, the foot support is malleable or pliable. In such embodiments, the foot support (or portions thereof) can have any suitable durometer value. For instance, some embodiments of the foot support comprise a padding layer having a durometer value between about 5 and about 120, or a durometer value that falls within any suitable sub-range thereof (e.g., a durometer value between about 30 and about 60), depending on the particular application of the foot support.

In some optional embodiments in which the foot support 14 comprises multiple layers of padding, the various padding layers each comprise a padding that has a different durometer value. Indeed, while, in some embodiments, the first padding layer 84 is softer than the second padding layer 86, in some preferred embodiments, the second padding layer is softer than the first padding layer. In this regard, the difference between the durometer value of the first padding layer and the second padding layer can be any suitable amount, including, without limitation, a value that is less than about 60, or any suitable sub-range thereof (e.g., a durometer value that is less than about 30). For instance, some embodiments of the foot support comprise a first padding layer having a durometer value of about 55±10 and a second padding layer having a durometer value of about 30±10. In some such embodiments, the first layer can provide needed support, while the second layer provides padding (e.g., for blood flow) and a desired level of comfort. Additionally, in some embodiments in which the foot support 14 comprises an offloading foot support (or a foot support defining an offloading hole 92), the durometer value(s) of the padding layer and/or padding layers are configured to help to offload weight/pressure from a foot wound while distributing such weight/or to other portions of a patient's foot.

Figure 9H:
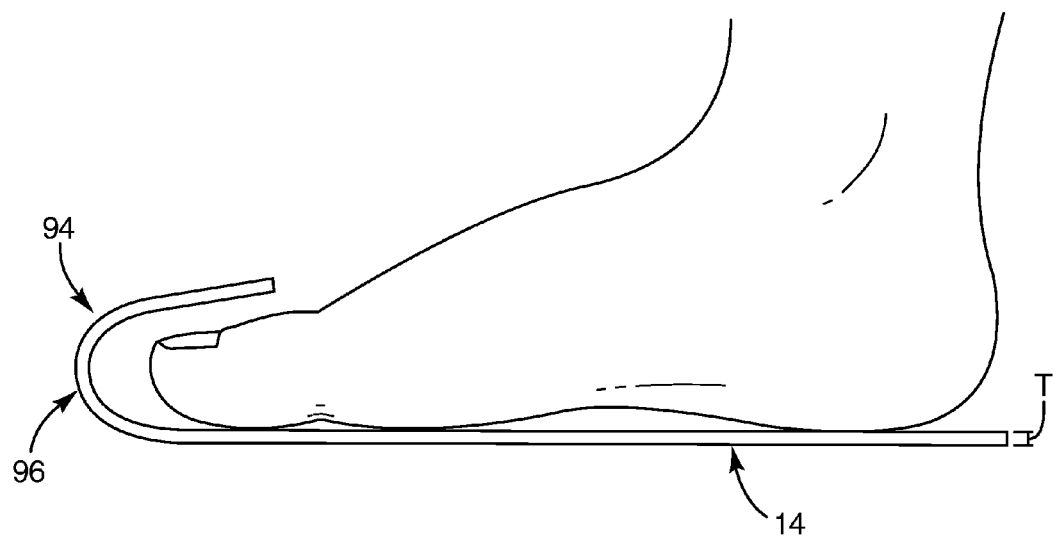
FIG. 9H illustrates a side elevation view of a foot disposed on a representative embodiment of the foot support.

In some embodiments, the foot support 14 comprises a toe guard that is configured to cover, cushion, and/or otherwise protect one or more of a patient's toes from being rubbed against a portion of the cast system 10 (e.g., the cast 12) and becoming macerated or otherwise injured. While the toe guard can comprise any suitable shape that allows it to fulfill its intended purpose, in some embodiments, it comprises a rounded end (e.g., an end having a J-shaped appearance, when viewed from its side), a box end (e.g., an end with a bottom surface, an end surface that runs substantially orthogonally to the bottom surface, and a top surface that runs substantially orthogonally to the end surface), a triangular end, a flat end (e.g., an end having a substantially flat surface that runs substantially orthogonally to (or at another suitable angle with respect to) a bottom surface of the foot support, giving the foot support an L-shaped appearance), and/or any other suitable shape that allows the toe guard to extend under one or more of a patient's toes, over (and/or in front of) a distal end of the toes, and/or over a dorsal portion of one or more of the toes. Indeed, FIGS. 9G-9H show some embodiments in which the toe guard 94 comprises a substantially J-shaped end 96.

In some embodiments, the shape of the toe guard 94 is substantially resilient, such that the toe guard's shape (e.g., a J-shaped appearance) is retained when the toe guard is at rest, or (said differently) when the shape of the toe guard is not being retained by an external force or object, such as a sock, a cast, underlayment, tape, bands, straps, ties, etc.). In other words, in some embodiments, the toe guard is manufactured to maintain its shape, even when the toe guard is separated from all other components of the described casting system 10.

While the toe guard 94 can be formed in any suitable manner that allows it to fulfill its intended purpose and to resiliently retain its shape, in some embodiments, the toe guard's shape (e.g., a resilient J shape, L-shape, etc.) is formed in the foot support via a heating process (e.g., forming the toe guard's shape with: a hot curling iron, pressing the foot support into a desired shape under the application of heat, etc.), a molding process, an extrusion process, and/or any other suitable process.

In some embodiments, the shape of the toe guard 94 is rigid or semi-rigid. In such embodiments, the toe guard can for formed with any suitable material (e.g., one or more rigid or semi-rigid plastics, polymers, metals, ceramics, rubbers, plastics, synthetic materials, woods, supports, braces, etc.) and in any suitable manner (e.g., via molding, extrusion, bending, and/or any other suitable process).

Figure 9I:
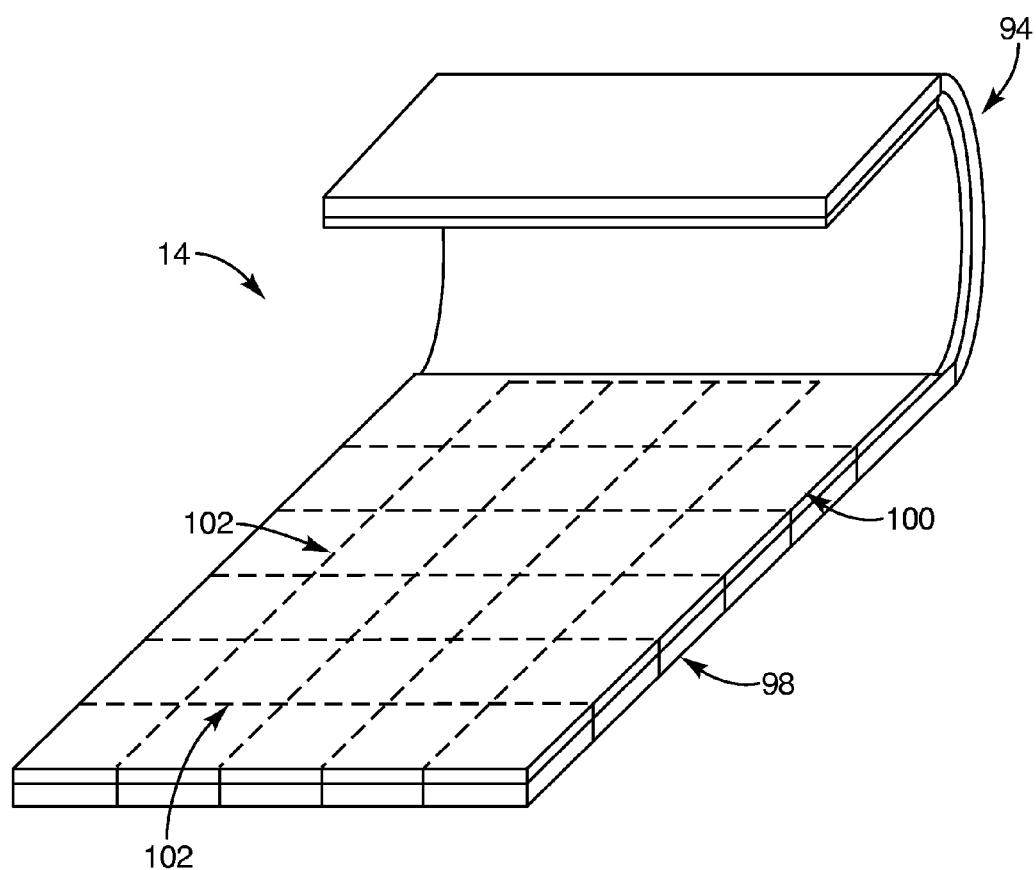
FIG. 9I illustrates a perspective view of the foot support comprising a plurality of perforations in accordance with a representative embodiment.
Figure 9J:
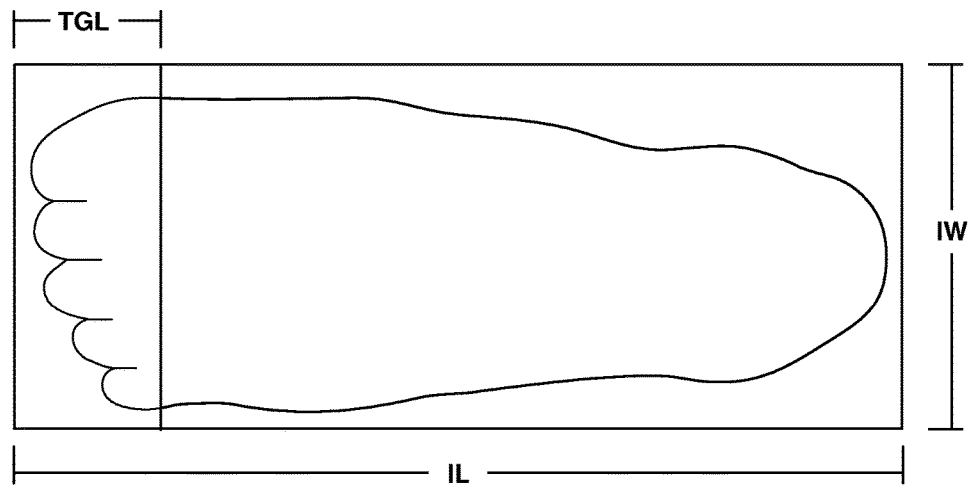
FIG. 9J illustrates a top plan view depicting a foot disposed on a representative embodiment of the foot support.
Figures 9K, 9L:
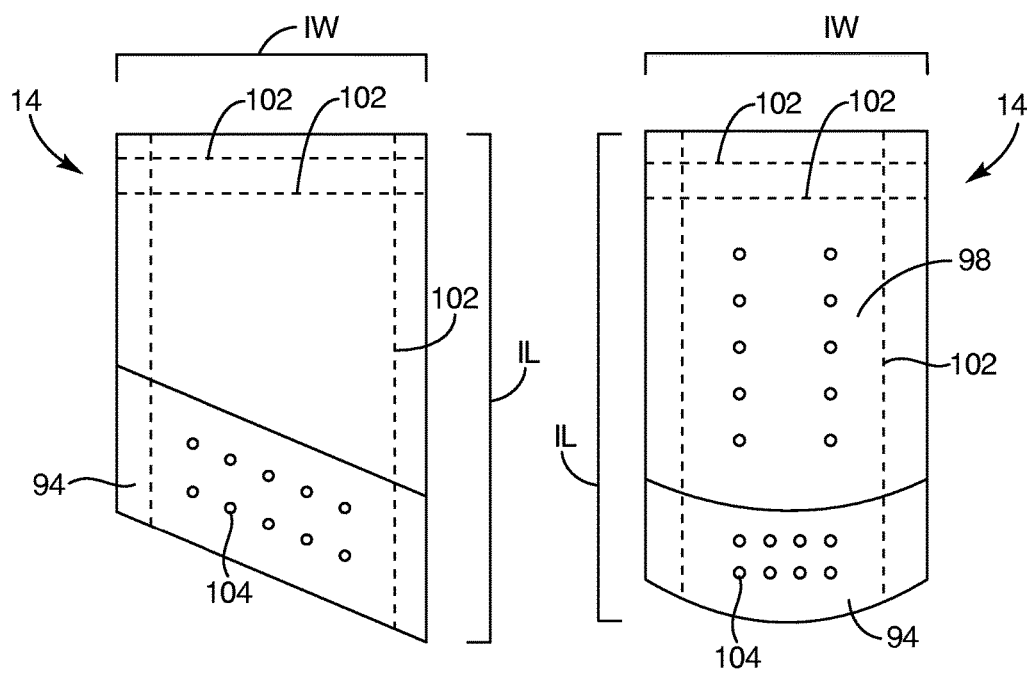
FIGS. 9K-9L each depicts a top plan view depicting representative embodiments of the foot support.
Figure 9M:
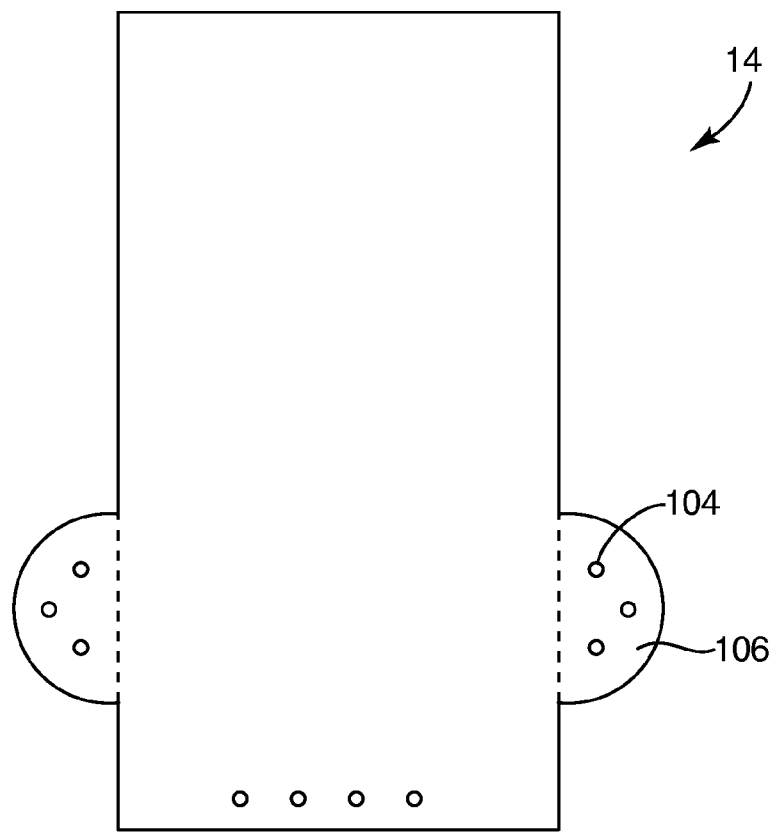
FIG. 9M illustrates a top plan view of a representative embodiment of the foot support.
Figure 9N:
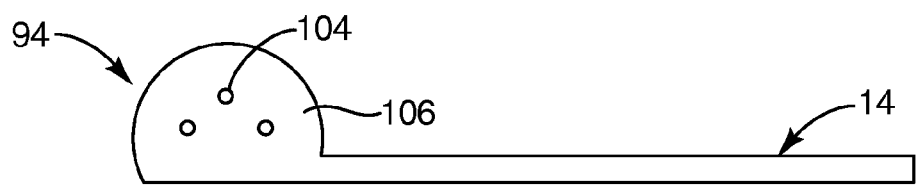
FIG. 9N illustrates a side elevation view of a representative embodiment of the foot support.
Figure 9O:
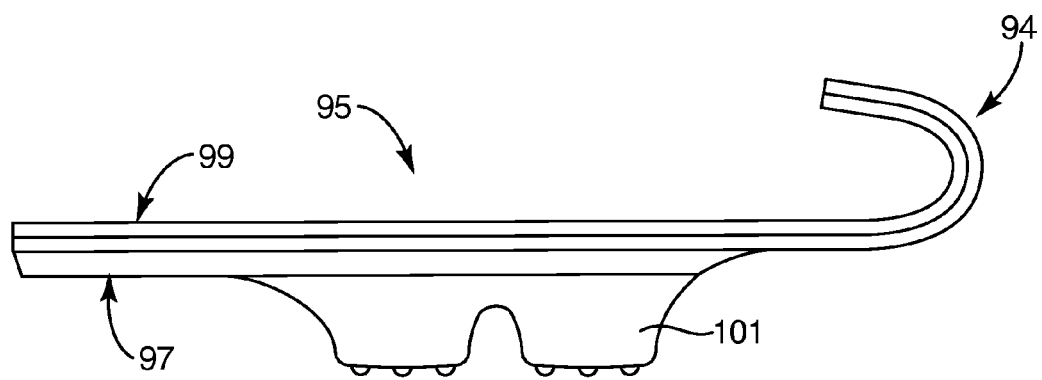
FIG. 9O illustrates a side elevation view of a representative embodiment of the foot support, wherein the foot support is configured for use as a representative embodiment of a cast walker.
Figure 9P:
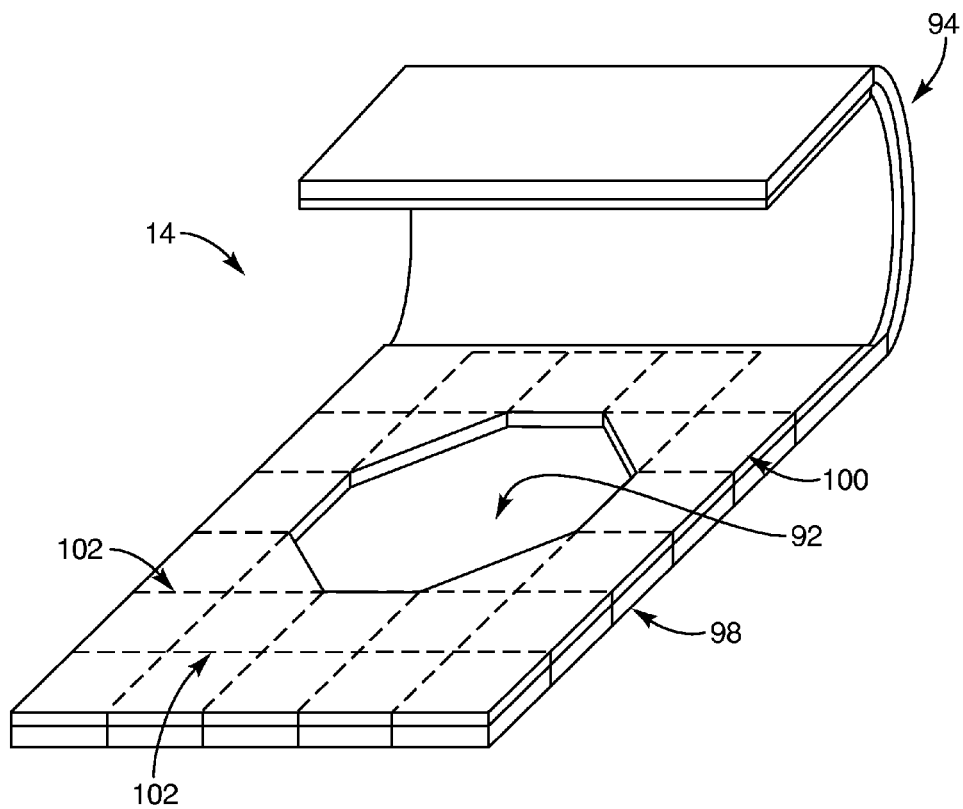
FIG. 9P illustrates a perspective view of the foot support defining an offloading hole.

In some embodiments, the foot support 14 comprises an offloading hole 92 (e.g., as shown in FIG. 9F) and/or is otherwise configured to be easily customizable. Indeed, in some embodiments, the foot support is formed with one or more offloading holes. In other embodiments, however, the foot support is configured such that a portion of the foot support can be removed to form an offloading hole or depression in a location corresponding to a wound on the sole 30 of a patient's foot. In this manner, the foot support can reduce the amount of pressure that is applied to a foot wound.

Where the foot support 14 is easily customizable, portions of the foot support can be removed in any suitable manner, including, without limitation, by removing portions of the foot support with scissors, a knife, a punch, and/or another cutting instrument. In some embodiments, however, the foot support comprises one or more perforated portions that are easily torn, cut, and/or otherwise separated to release one or more portions of the foot support. While such perforations can be disposed in any suitable location and in any suitable pattern, FIG. 9I shows an embodiment in which a sole portion 98 of the foot support 14 comprises a perforated pattern or grid 100 that allows select portions of the foot support to be removed to offset weight from (and to reduce pressure on) a foot wound. While FIG. 9I shows that some embodiments of the perforated grid 100 comprise a pattern of perforations in which at least two perforations run substantially perpendicular to each other, in other embodiments, the perforations run in any other suitable manner (e.g., in one or more circular or elliptical patterns, in one or more polygonal patterns, at any angle with respect to each other, and/or otherwise). By way of non-limiting illustration, FIG. 9P shows an embodiment in which the foot support 14 defines an octagonal offloading hole 92.

The foot support 14 can be any suitable size that allows it support a portion of a patient's foot 32 and/or to fit in a cast (e.g., cast 12 and/or any other suitable known or novel cast), shoe, and/or boot. For instance, while the foot support can be sold at any suitable length, in some embodiments, the foot support has an initial length (IL, as shown in FIG. 9J) between about 8 cm and about 40 cm, or that falls within any sub-range thereof (e.g., between about 25 cm and about 35 cm). Additionally, while the foot support can be produced to have any suitable initial width (IW), in some embodiments, the foot support has an initial width between about 2.5 cm and about 25 cm, or within any sub-range thereof (e.g., between about 10 cm and about 15 cm). Furthermore, while the toe guard 94 can extend posteriorly any suitable amount from an anterior end of the foot support, in some embodiments, the toe guard has a length (TGL) between about 0 cm and about 25 cm, or within any sub-range thereof (e.g., between about 2.5 cm and about 8 cm). Indeed, as shown in FIG. 9H, in some embodiments, the foot support 14 is of a sufficient length to allow a patient's toe to be spaced somewhat away from (e.g., posterior to) the toe guard 94. In this manner, the toe guard can further reduce and/or prevent maceration of a patient's toes, as tends to occur in some conventional total contact casts. Moreover, the foot support can be any suitable thickness (T, as shown in FIG. 9H). Indeed, in some embodiments, the foot support has a thickness between about 0.1 cm and about 2.5 cm, or that falls within any sub-range thereof (e.g., between 0.3 cm and 1.5 cm).

In some embodiments, the foot support 14 is further configured such that its size (e.g., length and/or width) is easily customizable for use with patients having varying foot sizes. While the foot support can be configured to be resized (and thereby become a custom offloading orthotic) in any suitable manner (e.g., by comprising a material that is cut relatively easily by a cutting instrument), in some embodiments, the foot support comprises perforations along one or more of its edges (e.g., its lateral edges and posterior edge). By way of illustration, FIGS. 9K-9L show some embodiments in which the foot support 14 comprises a plurality of perforations 102 along its edges to allow the length (e.g., IL) and/or width (e.g., IW) of the foot support to be reduced by cutting or tearing the foot support at such perforations. In this regard, while FIGS. 9K-9L shows some embodiments in which the perforations 102 comprise relatively straight lines, in some other embodiments, the perforations have any other suitable shape, including a shape that allows the foot support 14 to be easily modified to substantially track at least a portion of a patient's foot print.

In addition to the aforementioned characteristics, the foot support 14 can be modified in any suitable manner that allows it to offload weight from a foot wound and/or provide padding to a portion of a foot 32. In one example of a suitable modification, the shape of the toe guard 94 is modified to help the toe guard conform to one or more of a patient's toes. While the toe guard can be modified any suitable manner, FIG. 9K shows an embodiment in which, from a top plan view, the toe guard 94 is configured to slope from a patient's big toe (not shown in FIG. 9K) towards the patient's smallest toe (not shown in FIG. 9K). Similarly, FIG. 9L shows an embodiment in which, from a top plan view, the toe guard 94 is configured to curve from right to left, and vice versa.

In another example of a suitable modification, in some embodiments, the foot support 14 defines one or more ventilation holes. While these holes can be defined in any suitable portion of the foot support, FIGS. 9K-9L show some embodiments in which the foot support 14 defines ventilation holes 104 in the support's toe guard 94 and/or sole portion 98.

In another example, although some embodiments of the foot support 14 are completely open around the support's lateral, medial, and/or posterior edges, in some other embodiments, the foot support includes one or more sidewalls. In this regard, such sidewalls can be disposed in any suitable location on the foot support (e.g., so as to extend around any suitable length of a lateral edge, a medial edge, and/or a posterior edge of the foot support as well as to extend up to any suitable height on a patient's foot and/or leg. While such sidewalls can perform any suitable function, in some embodiments, one or more sidewalls are used to provide additional protection and/or wound-pressure offloading to a patient's foot and/or leg. Additionally, in some embodiments, the sidewalls and/or toe guard 94 optionally define one or more offloading holes 92 that are placed (e.g., via cutting, tearing, separating perforated lines, etc.) in the foot support at a position corresponding to one or more wounds on a patient's foot or leg—thus allowing weight/pressure to be offloaded from such wounds and distributed to other portions of the patient's lower leg. In any case, while the optional sidewalls can be formed in any suitable manner, FIGS. 9M-9N show some embodiments in which the sidewalls 106 are formed with (or are otherwise attached to) the foot support 14, such that the sidewalls are resiliently (and/or rigidly or semi-rigidly) maintained in position at one or both sides of the toe guard 94.

In another example, the foot support 14 comprise or is otherwise used with a die, carbon paper, and/or other pressure sensitive material that allows a user (e.g., a medical practitioner) to readily identify the position of a wound when a foot 32 is placed on the foot support. In this manner, the position of an offloading hole 92 in the foot support can readily be determined.

In another example, the foot support 14 and/or toe guard 94 are optionally modified to comprise one or more pads, walls, and/or other separators that are configured to extend (e.g., vertically or otherwise) between two or more of a patient's toes. In this example, such separators can perform any suitable function, including, without limitation, helping with ventilation, cushioning the toes, preventing one toe from rubbing against another, and/or otherwise protecting the patient's toes. Indeed, in some embodiments, such separators further comprise and/or are configured to be modified to comprise one or more offloading holes 92 that can be positioned to offload weight from a wound between a patient's toes.

In another example, one or more portions of the foot support 14 comprise an adhesive, mechanical fastener, frictional fastener, and/or other fastening mechanism that is configured to attach the foot support to any suitable object (e.g., a footplate, an internal surface of a cast (e.g., the described cast 12 and/or any other suitable cast), an underlayment 16 component (e.g., an internal and/or external surface of a constriction sock 110, a padding sock 112, a piece of localized padding 114, etc.), and/or any other suitable component. Indeed, in some embodiments, an external surface of the foot support comprises an adhesive that is configured to attach the foot support to a cast. In some other embodiments, an internal surface of the foot support comprises an adhesive that is configured to attach the foot support to a portion of the underlayment 16 (e.g., a sock).

In yet another example (previously discussed), some embodiments of the foot support 14 comprise an antimicrobial material (e.g., bamboo fabric, copper-coated fabric, silver-coated fabric, an antibiotic impregnated material, etc.). While this antimicrobial material can be disposed in any suitable location, in some embodiments, it is used as a covering on all or a portion of the foot support. By way of non-limiting illustration, FIG. 9G shows an embodiment in which the foot support 14 comprises an antimicrobial material 108, adjacent to the offloading hole 92.

Figure 11A:
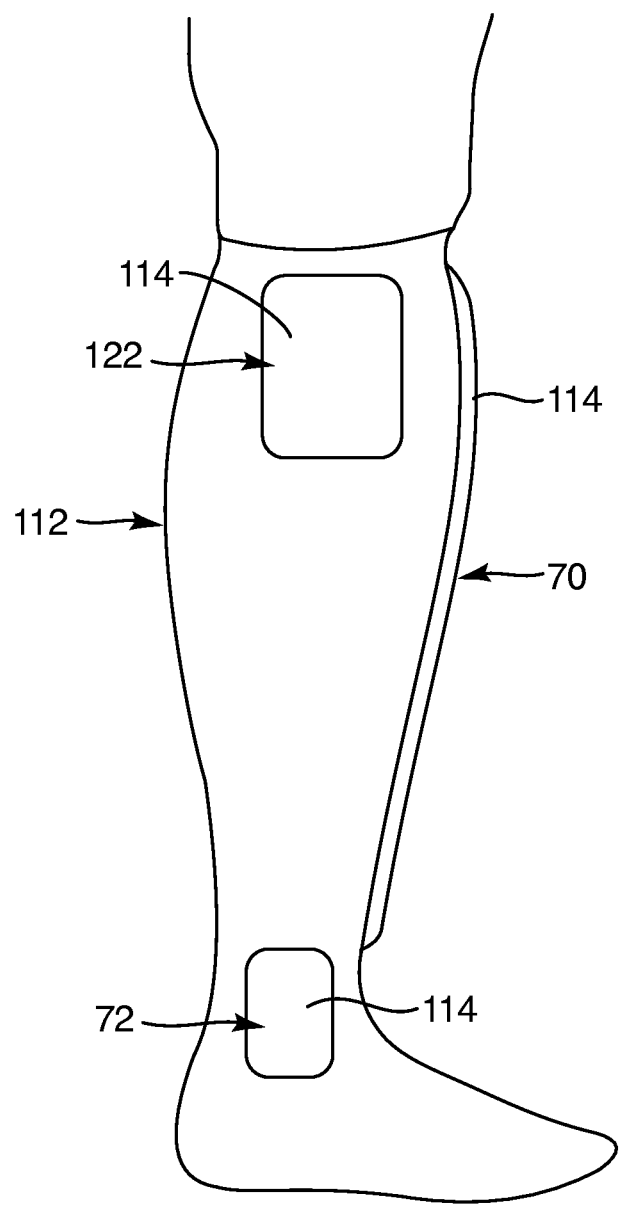
FIGS. 11A-11C each illustrates various side elevation views of representative embodiments of a cast underlayment comprising additional padding.
Figure 11B:
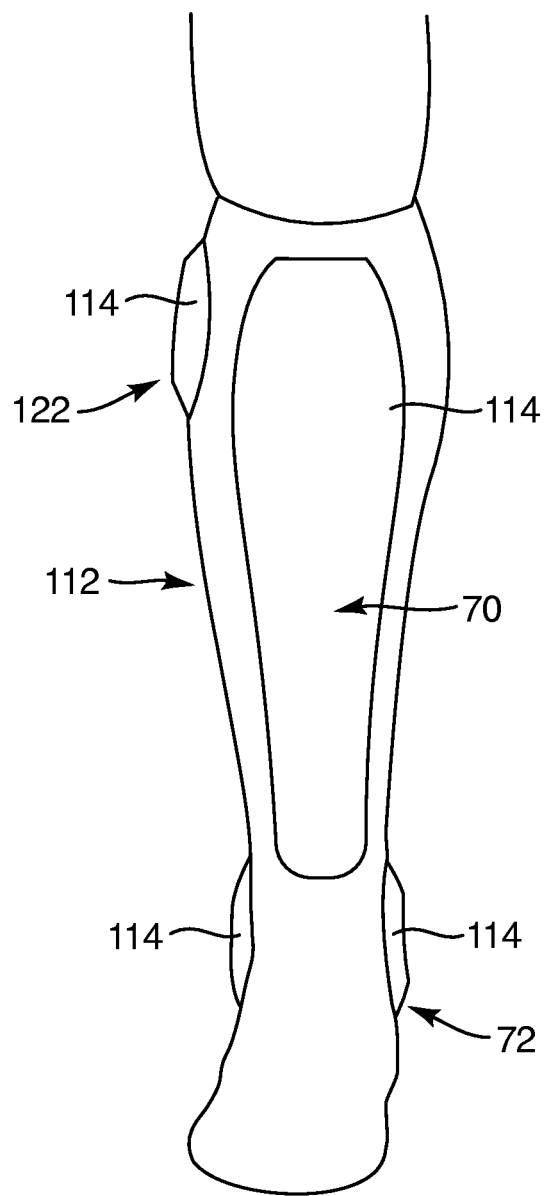
Figure 11C:
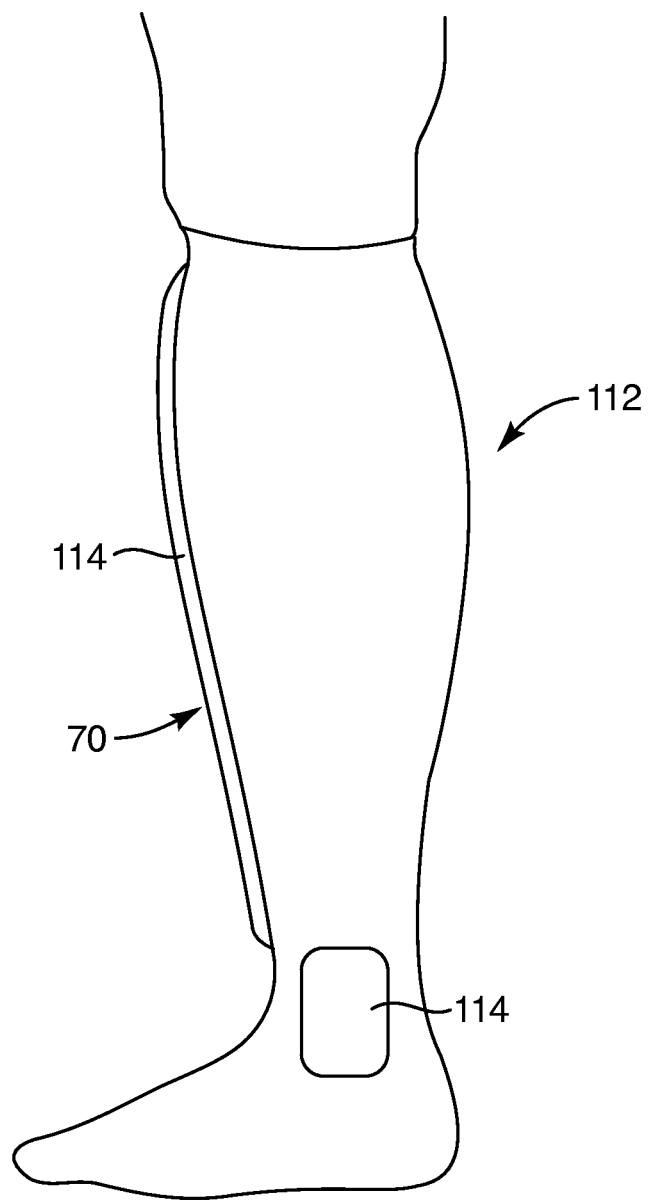
Figure 11D:
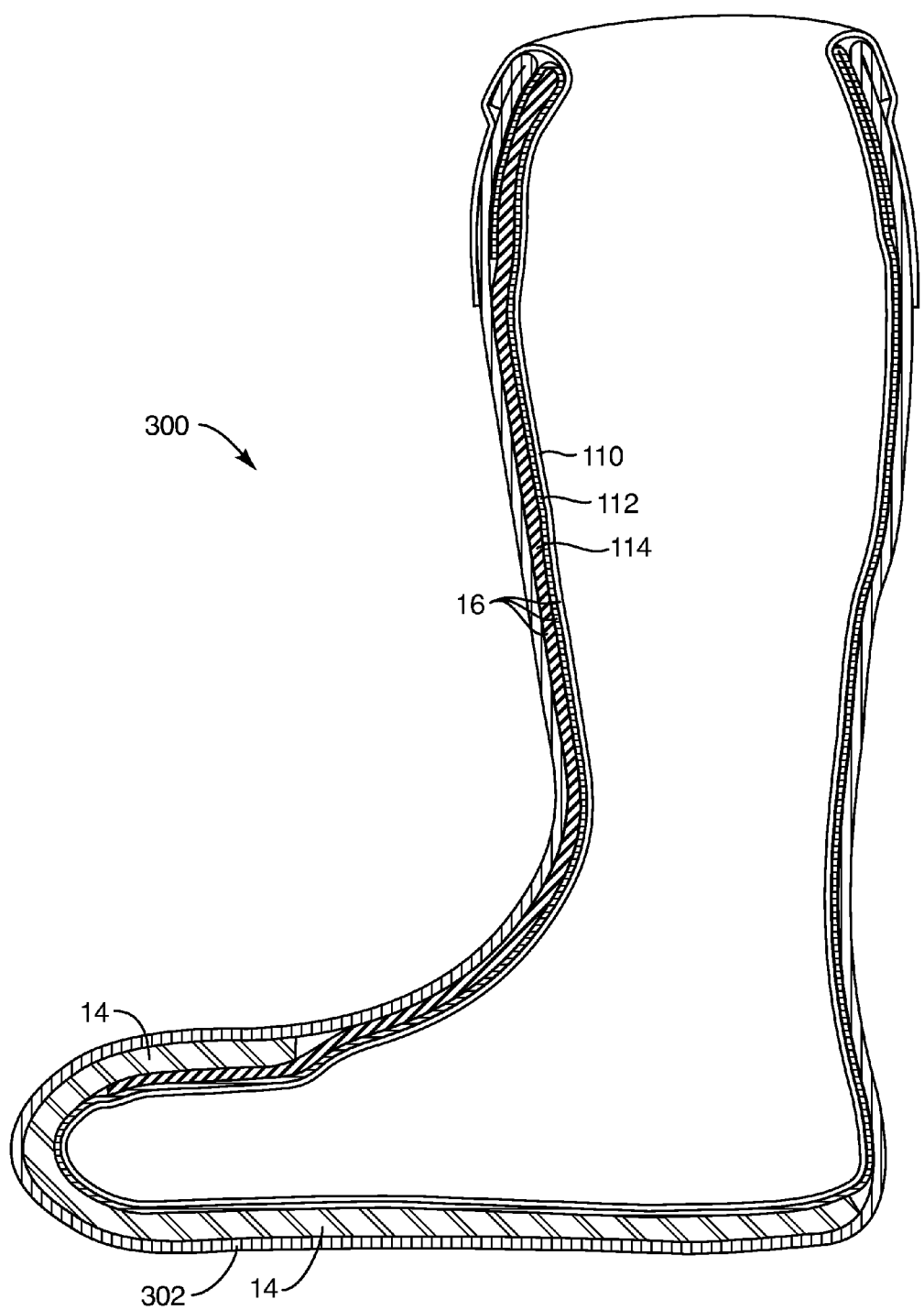
FIG. 11D illustrates a cross-sectional view depicting a representative embodiment of the cast underlayment.

In still another example, while the described foot support 14 is described herein for use with a total contact cast (e.g., cast 12), the foot support can be modified to be used with any suitable cast, including, without limitation, a known or novel cast for a broken leg, ankle, foot, or toe, a hand cast, an arm cast, etc. By way of non-limiting illustration (and skipping a little ahead in the figures), FIG. 11D shows that, in some embodiments, the foot support 14 is useable in virtually any known or novel casting system 300, including, without limitation, in a conventional cast 302 that is spirally wrapped around a body part.

In even another example, while some embodiments of the foot support 14 comprise a substantially flat portion on a which a patient's foot is to be placed, in some other embodiments, the at least a portion of the foot support is formed to contour or substantially contour to a portion (e.g., a sole) of a patient's foot. In this regard, the foot support can be made in different generic sizes that allow it to be used for a variety of patients and/or the foot support can be custom fit for individual patients. In this regard, the contour of the foot support can be formed in any suitable manner, including, without limitation, through the use of heat, a press, a mold, and/or any other suitable method.

As yet another example of a suitable modification, in some embodiments, the foot support 14 comprises a rigid orthotic which optionally has one or more layers of padding disposed thereon. While such a foot support can perform any suitable function, including (without limitation) providing support to a foot in a cast (e.g., cast 12), protecting a portion of a patient's foot (e.g., toes) from impacts, etc., in some embodiments, the foot support comprises a cast walker that allows a patient to walk on the cast, without the use of a separate boot and/or footplate.

Where the foot support 14 comprises a cast walker, the foot support can comprise any suitable characteristic. By way of non-limiting illustration (and jumping back in the figures to FIG. 9O), FIG. 9O shows a representative embodiment in which the foot support 14 comprises a cast walker 95 having a rigid support 97; a rigid, semi-rigid, and/or resilient toe guard 94; and one or more optional layers of padding 99 (e.g., which, in some embodiments, optionally define an offloading hole 92). Additionally, while an undersurface of the cast walker can have any suitable characteristic (e.g., be substantially flat, have one or more pedestals, contact surfaces, and/or other treads located proximally, anteriorly, in a middle of the foot support, and/or across any other suitable portion of the undersurface), FIG. 9O shows that, in some embodiments, the cast walker 95 comprises one or more contact surfaces 101 or treads that are somewhat centrally located on the walker.

Where the foot support 14 comprises a cast walker 95, the cast walker can comprise any suitable material. In this regard, some examples of suitable materials include, but are not limited to, one or more rubbers, polymers, plastics, woods, metals, ceramics, synthetic materials, natural material, and/or any other suitable material. In some embodiments, however, the cast walker comprises rubber.

In even another example of a suitable modification, in some embodiments, the foot support 14 is attached to, is disposed within, is connected to, and/or otherwise comprises a portion of any suitable type of sock and/or any other suitable object. Accordingly, in some such embodiments, the sock and foot support can be slid onto a foot and/or another suitable body part (e.g., a hand, arm, leg, etc.) to provide the body part with padding and/or wound offloading.

Figure 9Q:
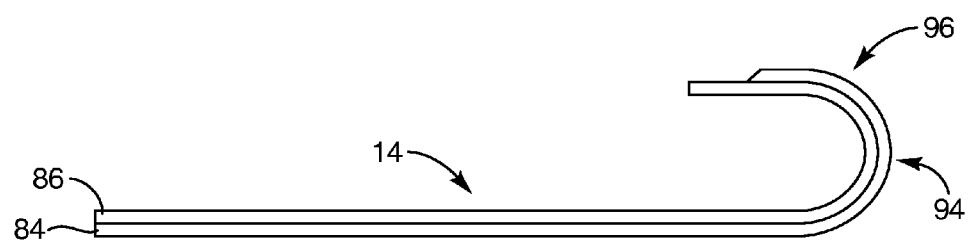
FIG. 9Q illustrates a side elevation view depicting a representative embodiment of the foot support.

In still another example of a suitable modification, an edge of the toe guard 94 that is configured to terminate over a dorsal portion of a patient's toe or foot) can have any suitable shape, including, without limitation, be substantially squared (e.g., as shown in FIG. 9O, rounded, tapered, and/or otherwise shaped. In some embodiments, however, such an edge is tapered. While this edge can be tapered in any suitable manner, FIG. 9Q shows that, in some embodiments, a portion of the toe guard 94 is thinned, beveled, tapered, and/or otherwise reduced in thickness to help reduce any pressure that can be applied to dorsal side of a patient's toes and/or foot by such embodiments of the foot support 14.

In addition to the characteristics previously mentioned, the described foot support 14 can have one or more other features. Indeed, in some embodiments, the foot support is configured to provide a patient with an offloading hole 92 that is specifically placed to offload weight from a wound on the patient's foot 32. As a result, some such embodiments can provide a patient with an individualized foot support that allows a wound on the patient's foot to heal faster that it may with some conventional casts.

As another example, the described toe guard 94 can protect a patient's toes better from friction with a cast (e.g., the cast 12 and/or any other suitable cast) or other damage and with less taping, or other external forces, than may some conventional casts. As a result, some embodiments of the described foot support can help reduce healing time, while limiting the amount of additional damage that is caused to a patient's toes while the patient's foot is in a cast.

In still another example, while the foot support 14 is described herein for use with a cast (e.g., the described cast 12 and/or any other suitable cast), the foot support can be used in any other suitable manner, including, without limitation, by being used alone and/or with a cast boot, a shoe, a bandage, and/or any other suitable element.

Cast Underlayment

Figure 10A:
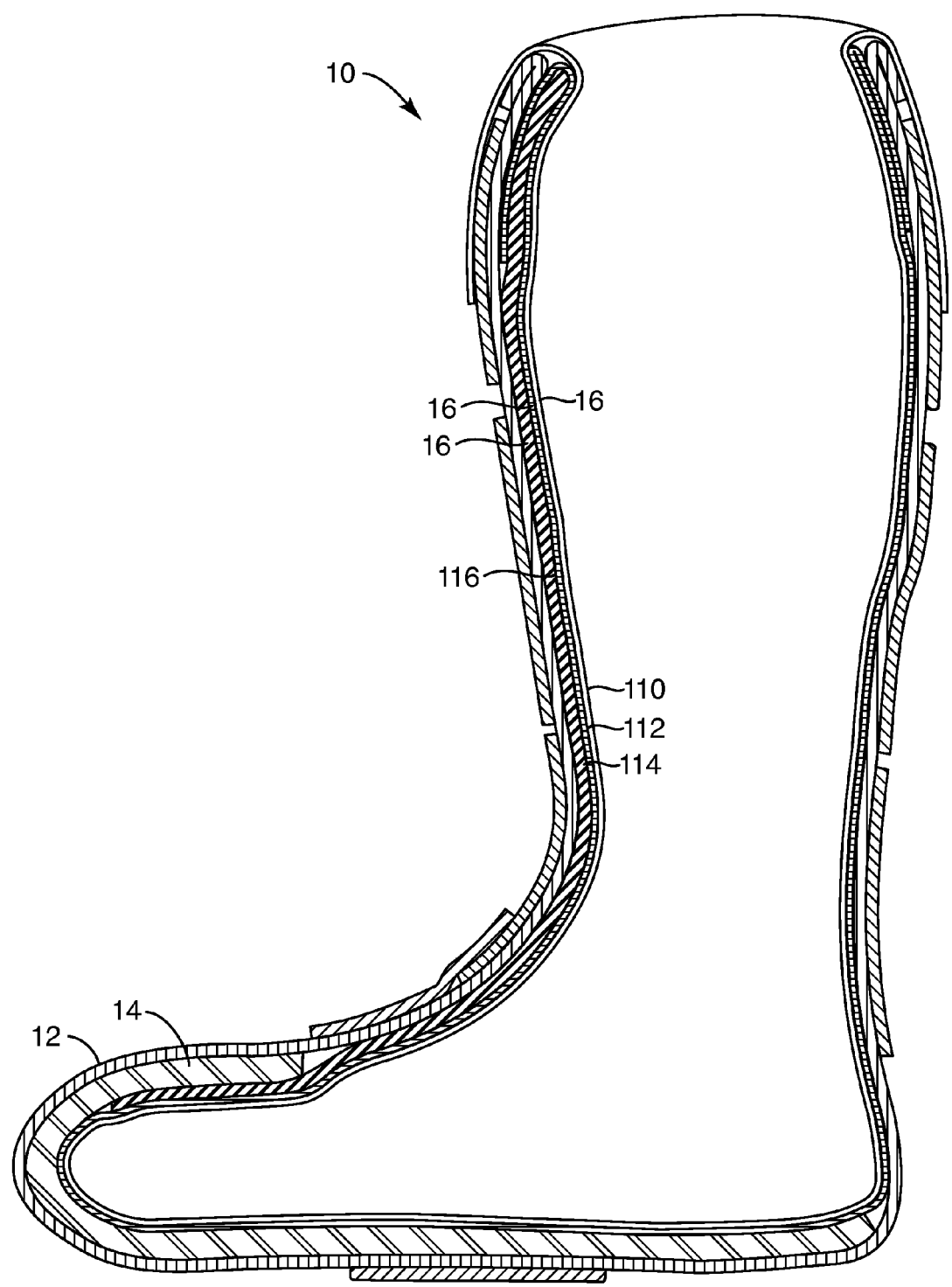
FIG. 10A illustrates a cross-sectional view of a representative embodiment of the orthopedic cast system.

With respect to the cast underlayment 16, the underlayment can comprise any suitable material or object that is configured to be disposed between an internal surface of a cast (e.g., the cast 12 and/or any other known or novel cast and/or splint) and the skin of an appendage within the cast. Indeed, in some embodiments, the underlayment comprises one or more articles configured to provide compression to an appendage within the cast, pieces of padding, negative pressure apparatus (e.g., negative pressure socks, tubing, etc.), and/or other items that can be disposed between the cast and a patient's skin. By way of non-limiting illustration, FIG. 10A illustrates an embodiment in which the cast underlayment 16 comprises a compression sock 110 (or other suitable compression layer), a padding sock 112 (or other suitable padding layer), and localized padding 114. In this regard, in some embodiments in which the underlayment comprises two or more components (or layers) the various components are configured to transfer shearing forces or movements from between a cast (e.g., the described cast 12 and/or any other suitable cast or splint) and the skin covered by the cast to between the two or more components of the underlayment. In such embodiments, the described underlayment can reduce the maceration and other damage that can be caused by some conventional cast systems that chafe against the skin they cover.

The various components (or layers) of the underlayment 16 (e.g., the compression sock 110, padding sock 112, localized padding 114, etc.) can be made of any suitable materials that allow the components to function as intended. Some non-limiting examples of such materials include cotton, cellulosic fibers, gauze, polyurethane foam, neoprene, polyester, rayon, and/or one or more antimicrobial materials.

Where one or more components (or layers) of the underlayment 16 comprise an antimicrobial material (e.g., an anti-fungal, an anti-bacterial material, a bactericide, and/or any other suitable antimicrobial material), the underlayment can comprise any suitable antimicrobial material. Some examples of such materials include, but are not limited to, one or more bamboo fabrics and bamboo materials (e.g., bamboo cloth, bamboo rayon, polyester made from bamboo, and/or any other suitable fabric and/or material comprising bamboo), silver-coated materials (e.g., silver-coated poly (ethylene terephthalate), silver-coated rayon, silver-coated polyester, etc.), copper-coated materials, silver/copper-coated materials, silver/copper/nickel-coated materials, silver/copper/tin-coated materials, iodine incorporated materials, bactericide, and/or any other suitable antimicrobial material (e.g., as discussed above), including, without limitation, those antimicrobial materials having one or more anti-odor characteristics. In some implementations, however, the underlayment comprises a bamboo-containing fabric. In this regard, each underlayment component can comprise any suitable amount of bamboo (e.g., between about 0.1% and about 100%, or any sub-range thereof, including, without, limitation, between about 75% and about 99%).

Figure 10B:
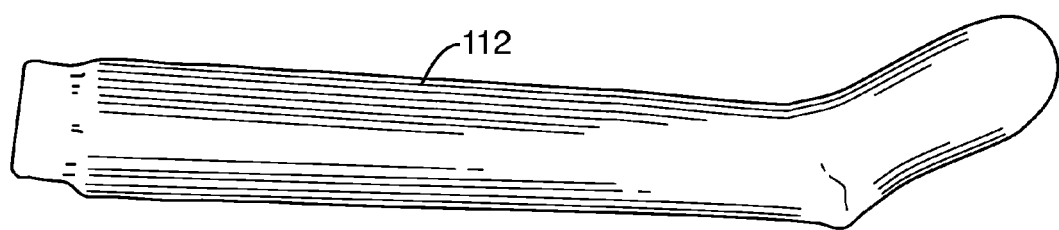
FIG. 10B illustrates a plan view of a representative embodiment of a compression sock.

In some embodiments (as mentioned above), the underlayment 16 comprises one or more articles or layers that are configured to provide compression to an appendage within a cast (e.g., the described cast 12). In such embodiments, the underlayment can comprise any suitable article that is configured to provide pressure to an appendage within the cast. In some instances, however, this compression article comprises a compression sock, stockinette, tube, and/or sleeve (collectively and individually a compression sock 110; a representative embodiment of which is shown in FIG. 10B).

While the compression sock 110 can provide any suitable amount of pressure to an appendage (e.g., lower leg 24), in some embodiments, the compression sock is configured to provide compression to an appendage at any suitable pressure level. In this regard, in some embodiments, the compression sock is configured to provide an appendage with between about 5 mmHG and about 30 mmHG of pressure, or any sub-range thereof (e.g., between about 10 mmHG and about 20 mmHg, or even between about 10 and 15 mmHG). Moreover, although in some embodiments, the compression sock comprises a static compression sock that is configured to provide a substantially constant compression across the appendage to which it is applied, in other embodiments, the compression sock comprises a sequential compression sock that is configured to provide greater compression at a distal end of the sock (e.g., by a patient's toes).

Figure 10C:
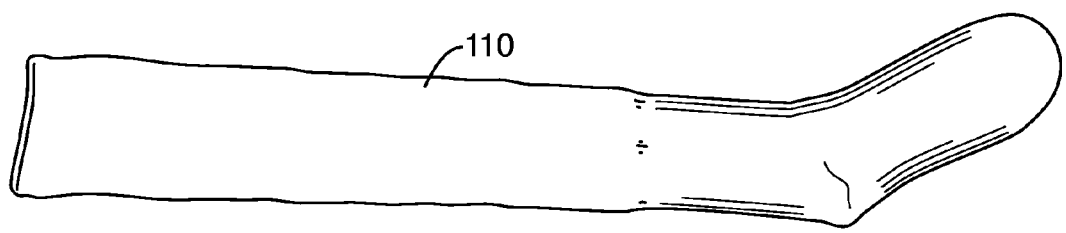
FIG. 10C illustrates a plan view of a representative embodiment of a padding sock.

In some embodiments (as mentioned above), the underlayment 16 comprises one or padding layers or socks 112 (see e.g., FIG. 10C) that are configured to provide padding to an appendage within the cast (e.g., cast 12). In such embodiments, the padding sock can comprise any suitable article (e.g., sock, stockinette, sleeve, tube, sheet, etc.) that is configured to provide padding around a portion of an appendage within the cast (e.g., cast 12). Moreover, while the padding sock can provide any suitable amount of padding, in some embodiments, the sock is configured to be between about 1 mm and about 3 cm thick (e.g., before being applied to an appendage), or to have a thickness that falls in any sub-range thereof (e.g., between about 1.5 cm and about 2 cm). Additionally, although in some embodiments, the cast (e.g., cast 12 and/or another suitable cast) is configured such that the padding sock is not bound to an internal surface of the cast, in other embodiments, a portion (if not all) of the padding sock becomes bound to the cast, either before or after the cast hardens.

While various components of the underlayment 16 can be made in any suitable manner (e.g., via spinning, knitting, crocheting, weaving, sewing, extruding, etc.), in some embodiments, one or more components (e.g., the compression sock 110 and/or padding sock 112) are knitted and/or woven. Although this knitting and/or weaving process can be accomplished in any suitable known or novel manner, in some embodiments, this process is done such that the various components of the underlayment (e.g., the compression sock and padding sock) comprise a weave that is configured to be non-fraying (or to not significantly fray or unravel when such components are punctured or cut (e.g., at least when such components are not cut completely around their perimeter). As a result, in some such embodiments, the various components can be cut or punctured (e.g., to allow medical tubing, such as a vacuum tube, a drain tube, etc., to pass through one or more components) without causing significant damage to such components.

Figure 10D:
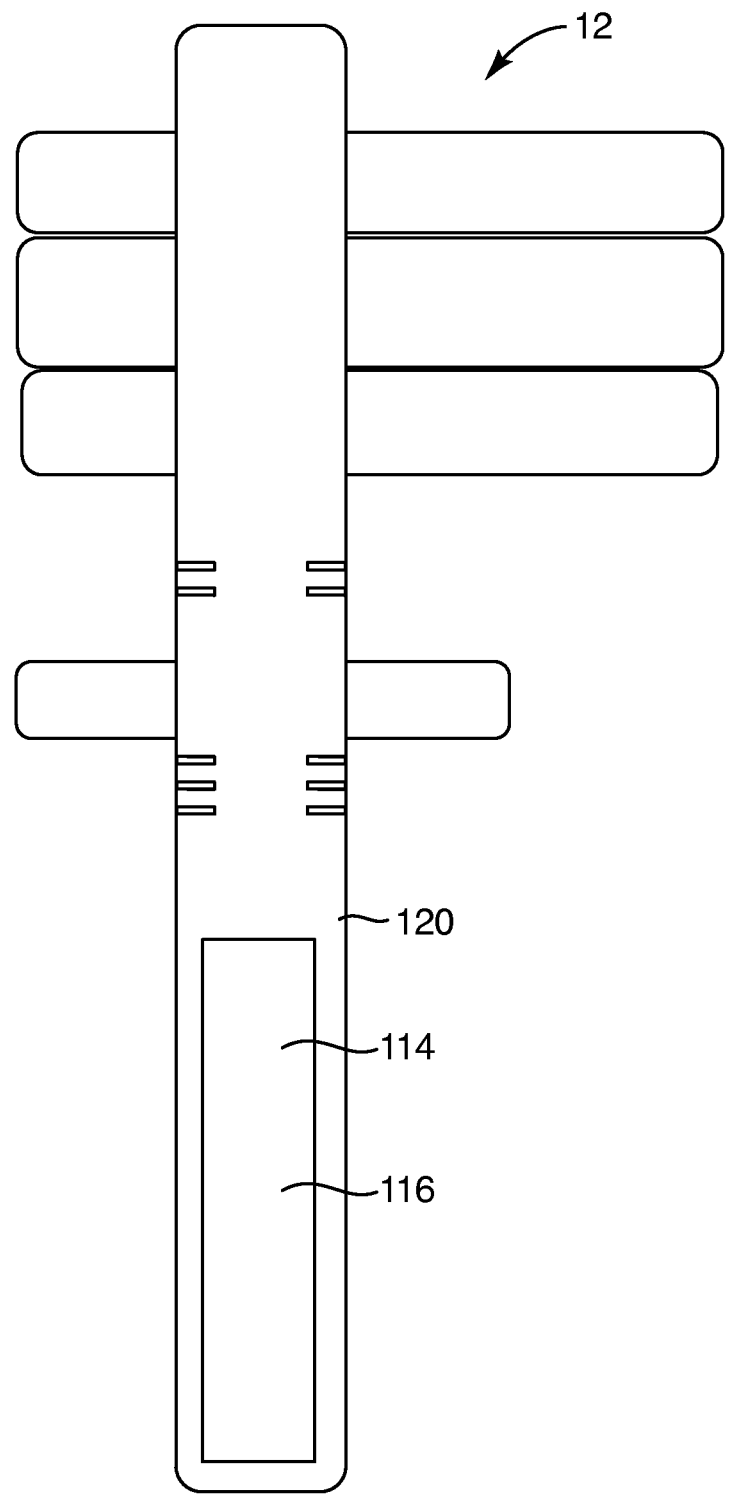
FIGS. 10D-10F each illustrates a plan view of representative embodiments of the clam-shell cast.
Figure 10E:
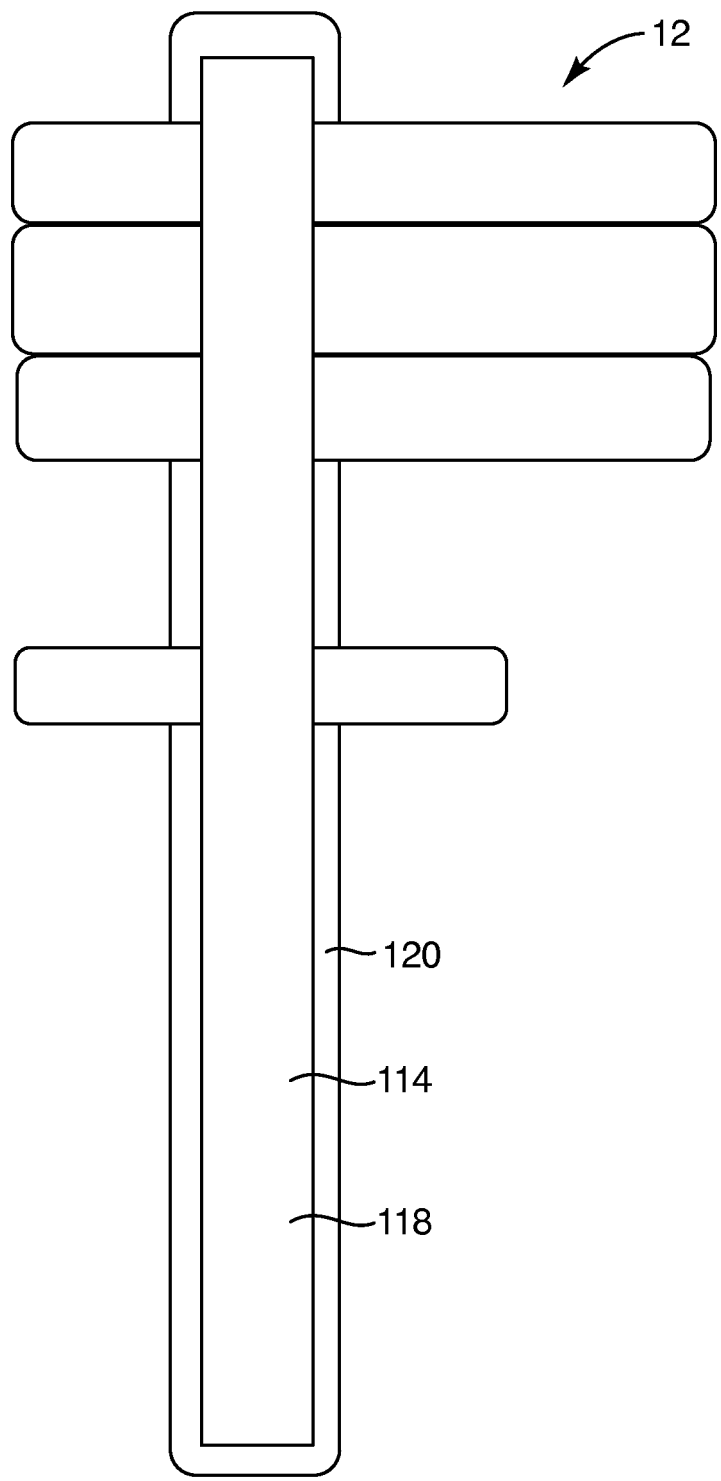
Figures 10F, 10G:
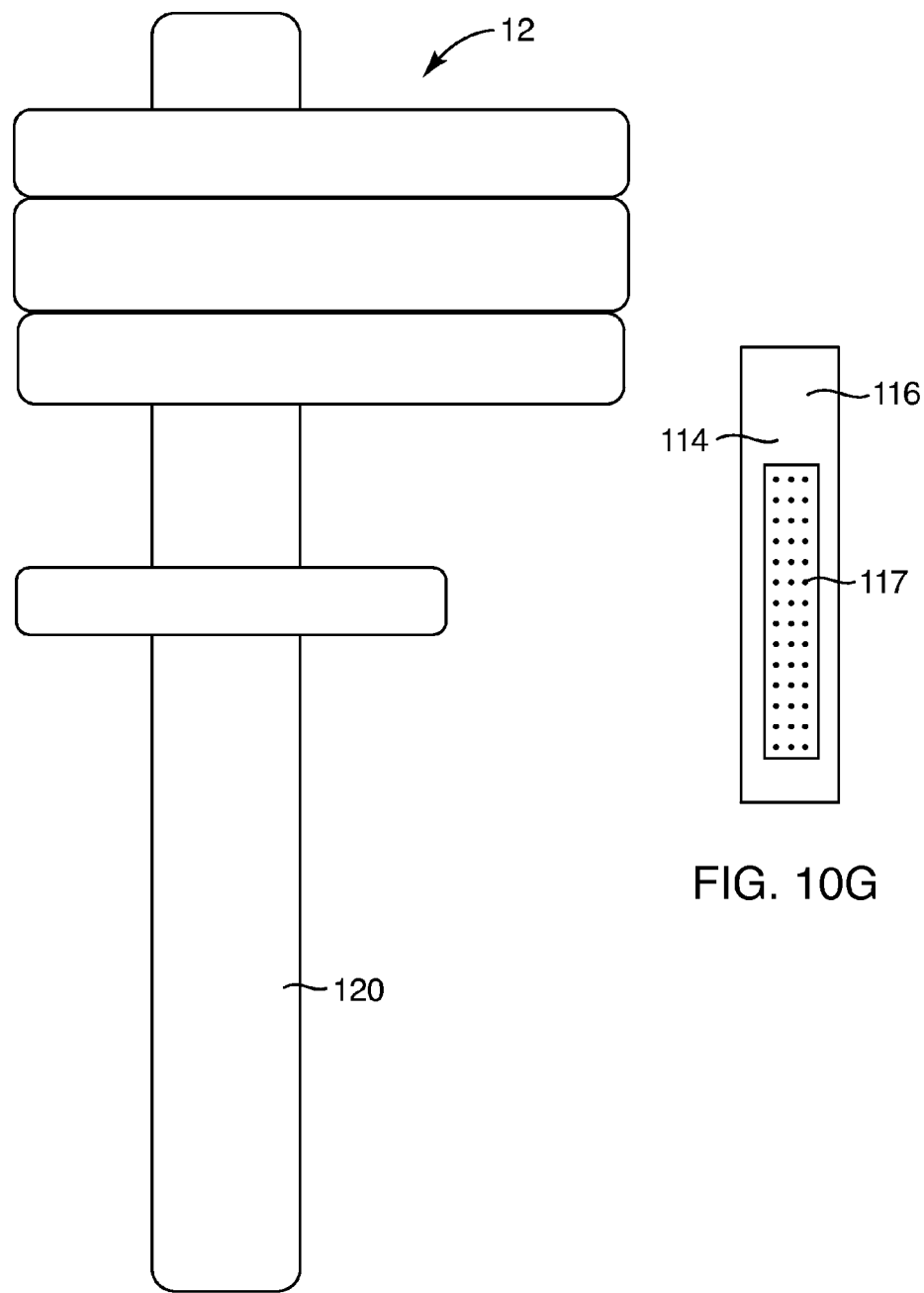
FIG. 10G illustrates a plan view of a representative embodiment of a piece of additional padding.

With respect to the localized padding 114, the underlayment 16 can optionally comprise any suitable amount of additional padding in any suitable location (e.g., over a patient's toes, dorsal portion of the patient's foot, shin, calf, ankle, a lateral side of a proximal portion of a patient's fibula, an anterior portion of a proximal portion of a patient's tibia, and/or any other body part in the cast (e.g., cast 12)) that could benefit from additional padding. While the additional padding can have any suitable relation with respect to the cast and one or more components of the underlayment, in some embodiments, the localized padding is fixed to an internal surface of the cast (e.g., via stitching, an adhesive, tape, and/or any other suitable mechanism). In this regard, FIGS. 10D and 10E respectively illustrate embodiments in which an optional shin pad 116 and a full length pad 118 are attached to an internal surface 120 of the cast 12. In contrast, FIGS. 10F and 10G shows an embodiment in which an optional shin pad 116 is configured to be added to the cast 12, as desired. Moreover, FIGS. 11A-11C show that, in some embodiments, the localized padding 114 is attached to another portion of the underlayment (e.g., the compression sock 110 and/or the padding sock 112). While such padding can be disposed in any suitable location, FIGS. 11A-11C shows that, in some embodiments, the additional padding 114 as configured to be placed over an ankle portion 72, a shin portion 70, and lateral leg portion 124 (e.g., over a proximal, lateral portion of a fibula and/or a tibia of a patient).

In addition to the aforementioned characteristics, the cast underlayment 16 can be modified in any suitable manner that allows it to pad, provide shear reduction to, ventilate, and/or otherwise protect an appendage within a cast (e.g., cast 12). In one example of a suitable modification, the various components of the underlayment 16 (e.g., the compression sock 110, padding sock 112, and/or localized padding 114) can be used alone (e.g., with any combination of each other), with any suitable combination of the elements of the described cast system 10, and/or with any other suitable cast, splint, and/or bandage system. Indeed, in some embodiments, one or more portions of the underlayment (e.g., a compression sock, padding sock, and/or localized padding comprising an antimicrobial material) is used as underlayment in a known or novel: upper extremity cast (e.g., a short arm cast, a long arm cast, a finger spica, a thumb spica, etc.), lower extremity cast (e.g., a long leg cast, short leg cast, etc.), cylinder cast, body cast, spica, splint, and combinations thereof. In one non-limiting example, a compression sock and a padding sock comprising a bamboo material (and/or another antimicrobial material) are used as underlayment in an arm cast. Similarly, in one non-limiting illustration, FIG. 11D shows an embodiment in which one or more components of the underlayment 16 (e.g., the compression sock 110, the padding sock 112, and the localized padding 114) are useable in virtually any known or novel casting system 300, including, without limitation, in a conventional cast 302 that is spirally wrapped around a body part.

In another example, in some embodiments, the first underlayment component (e.g., the compression sock 110) has a higher compression than the second underlayment (e.g., the padding sock 112). In some such embodiments, such a configuration allows for an increased probability that shear forces will be transferred to the interaction between the first underlayment component and the second underlayment component (and/or another underlayment component) instead of at an interface between the skin and the first underlayment component.

In another example of a modification, any suitable portion of the underlayment 16 (e.g., the compression sock 110, padding sock 112, and/or localized padding 114) can be removed from the cast system 10 and/or any other component can be added to the system. Indeed, while the underlayment can comprise two layers of material (e.g., a compression and padding sock), in some embodiments, the underlayment comprises 3, 4, 5, 6, 7, 8, or more layers. In some such embodiments, the additional layers (e.g., one or more socks, stockinettes, sleeves, sheets, etc.) can perform any suitable purpose, including allowing shearing forces to take place between the various layers, as opposed to taking place against a patient's skin as the cast moves with respect to such skin.

In still another example, in some embodiments, one or more components of the underlayment 16 comprise one or more holes that are preformed (e.g., woven into, knitted into, cut into and then stitched to prevent unraveling, and/or otherwise formed) in the various underlayment components. Accordingly, in some such embodiments, the various components can be used for ventilation and/or with medical tubing, without requiring that such components be punctured, cut, or torn to accommodate such ventilation and/or tubing.

In yet another example of a suitable modification, the various components of the underlayment 16 can be placed on an appendage (e.g., lower leg 24) in any suitable order. For instance, while FIG. 10A depicts an embodiment in which the compression sock 110 is disposed closest to the patient's lower leg 24 (not shown in FIG. 10A), with the padding sock 112 disposed outside the compression sock 110, and with shin padding 116 and the foot support 14 disposed outside of the padding sock, the order of such components can be reorganized in any suitable manner. Indeed, in some instances, the foot support is disposed within the compression sock.

In another example, while, in some embodiments, each element of the underlayment 16 (e.g., the compression sock 110, padding sock 112, and localized padding 114) is used together (e.g., in a cast, splint, shoe, prosthetic, ski boot, rollerblade/roller-skate boot, in a post-operation setting, and/or other suitable environment), in some other embodiments, the various components of the underlayment are used individually and/or in any other suitable combination (e.g., to reduce shear damage that can be caused to a person's skin when such skin is in close proximity to another object, such as an interior of a prosthetic, a hiking boot, a ski boot, etc.). By way of non-limiting illustration (and returning back to FIG. 1C, that figure shows an embodiment in which the optional localized padding 114 is omitted and the compression sock 110 and the padding sock 112 are used in the described cast 12 (e.g., to provide for shear reduction between a patient's skin (not shown in FIG. 1C) and an internal surface of the cast 12).

In still another example, while some embodiments of the underlayment 16 can move completely independently of the cast 12 (or another suitable cast, splint, and/or bandage), in some other embodiments, one or more components of the underlayment are at least partially attached to the cast when the cast and underlayment are disposed on an appendage. In these latter embodiments, any suitable portion of the underlayment (e.g., the compression sock 110, the padding sock 112, and/or the localized padding 114) can be attached to the cast, in any suitable manner (e.g., via one or more adhesives, pieces of tape, tackifiers/hardening materials in the casting material, mechanical attachments, frictional attachments, etc.). As a result, in some embodiments, the described underlayment is able to reduce shearing forces between the cast and the patient's skin.

In yet another example of a suitable modification, some embodiments of the compression sock 110, the padding sock 112, and/or the localized padding 114 comprise and/or are configured to comprise (e.g., via cutting, tearing, separating perforated lined, and/or otherwise configured to define) an offloading hole that is configured to correspond in position to a wound on an appendage using such component(s). In this manner, one or more components of the underlayment 16 can help offload at least some weight/pressure from a wound, and distribute such weight/pressure to another portion of the appendage using such component(s).

Each of the various components of the underlayment 16 can optionally be modified in any suitable manner that allows them to define an offloading hole 92 that can correspond in position to a wound on an appendage (and/or any other suitable body part). In one example, one or more components of the underlayment are manufactured to include one or more offloading holes. In another example, however, some embodiments of one or more of the underlayment components are easily customizable, such that one or more portions of the various underlayment components can be removed to provide an offloading hole. In such embodiments, the various portions of the underlayment can be removed in any suitable manner, including, without limitation, by removing portions of the compression sock 110, the padding sock 112, and/or the localized padding 114 with scissors, a knife, a punch, and/or another cutting instrument. In some embodiments, however, one or more of the underlayment components comprise one or more perforated portions that are easily torn, cut, and/or otherwise separated to release one or more portions of such component(s). By way of non-limiting illustration, FIG. 10G shows an embodiment in which the optional localized padding 114 comprises a plurality of perforated lines 117 that allow one or more portions of the padding to be removed to create an offloading hole (not shown) that can correspond in position to a wound.

In addition to the characteristics previously mentioned, the described cast underlayment 16 can have several features. Indeed, in one example, where one or more portions of the underlayment (e.g., the compression sock 110, the padding sock 112, and/or the localized padding 114) comprise an antimicrobial material (e.g., a bamboo fabric), the underlayment may help combat infection, odor, bacteria, fungus, excess moisture, and/or otherwise help wounds on the bandaged appendage to heal. Additionally, in some embodiments in which one or more components of the underlayment comprise bamboo or another breathable fabric (including, without limitation, a fabric that is formed with ventilation holes in it), the cast system 10 can provide better ventilation than may some conventional casts that simply comprise a cotton underlayment. As a result, of the foregoing, some embodiments of the described underlayment can improve healing time and/or reduce the costs associated with certain healing procedures.

In yet another example of a beneficial characteristic of the underlayment 16, in some implementations in which the underlayment comprises 2, 3, 4, 5, or more layers of one or more materials (e.g., one or more compression sock 110, padding socks 112, localized padding 114 layer, etc.), the underlayment functions as a multi-layer shear reduction system, allowing shearing movement between the skin of a casted appendage and the cast itself to take place between the multiple layers of the underlayment (e.g., the padding sock 110 and the compression sock 112). As a result, some embodiments of the described underlayment can dramatically reduce the skin damage that is often caused by some conventional casts.

Footplate/Boot

Figure 12A:
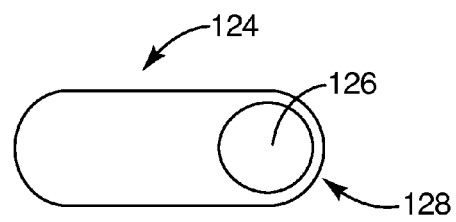
FIG. 12A illustrates a top plan view of a representative embodiment of a footplate.

With respect to the footplate and boot 18, the footplate and/or boot can comprise any suitable component that allows a patient to wear the footplate and/or boot on a wounded foot/leg. With respect to the footplate, the footplate can include any suitable component or characteristic that allows it to support a patient's foot. Indeed, in some embodiments, the footplate comprises a top plantar surface and an undersurface. In this regard, the top surface can include any suitable characteristic that allows the footplate to support a patient's foot. By way of non-limiting illustration, FIG. 12A shows that, in some embodiments, the footplate 124 defines an indentation (or a heel cup 126) towards the plate's posterior end 128. While this indentation can perform any suitable function, in some embodiments, it is configured to cradle a patient's heel and/or to help ensure that the patient's heel is correctly positioned on the orthopedic footplate 124 (i.e., when the foot is first placed on the footplate and as the patient walks).

Figure 12B:
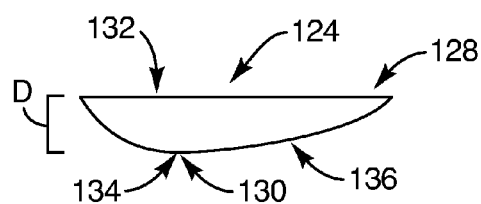
FIGS. 12B-12D each illustrates a side elevation view of representative embodiments of the footplate.
Figure 12C:
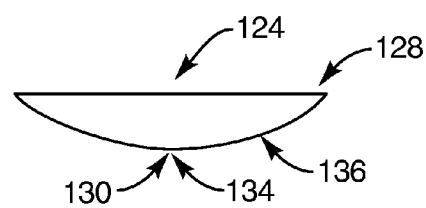
Figure 12D:
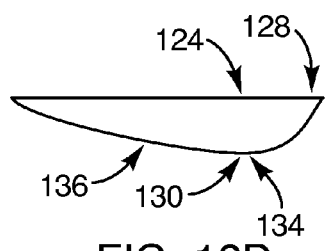

While the undersurface of the footplate 124 can comprise any suitable characteristic that allows a patient to walk on the footplate, in some embodiments, the footplate comprises a cam-shaped undersurface. In this regard, an eccentric portion of the cam-shaped undersurface can be disposed in any suitable location (e.g., posteriorly, medially, laterally, anteriorly, in the middle of the footplate, etc.) that allows the patient to walk and/or slide the patient's foot across a surface. By way of non-limiting illustration, FIGS. 12B, 12C, and 12D respectively show embodiments in which the eccentric portion 130 of the footplate 124 is disposed anteriorly, in the middle, and posteriorly on the footplate 124.

As another example of a suitable characteristic of the footplate 124, the footplate can have any suitable thickness that allows a patient to walk on it. Indeed, in some embodiments, the distance (as shown by D in FIG. 12B) between a highest point on the top surface 132 of the footplate upon which a patient places the patient's foot and a lowest point 134 on the undersurface 136 of the footplate is between about 1 mm and about 5 cm. Moreover, the distance D between the highest point on the top surface and the lowest point on the undersurface of the footplate can fall in any sub-range of the aforementioned range (e.g., between about 0.3 and about 1.5 cm). Indeed, in some embodiments, the described footplate is relatively thin (e.g., between about 0.4 and about 0.8 cm), thus, reducing any limb length discrepancy between a patient's leg that is using the footplate and (where the patient only wears the footplate on one foot) the patient's leg that is not wearing the footplate.

Figure 12E:
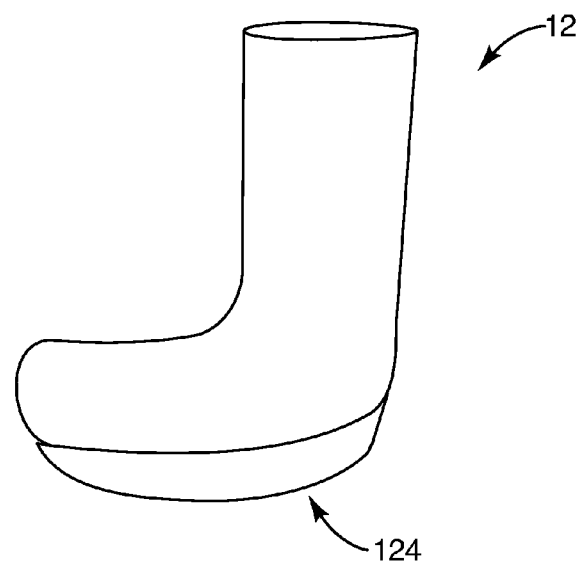
FIG. 12E illustrates a side elevation view of the footplate attached to the cast in accordance with a representative embodiment.
Figure 12F:
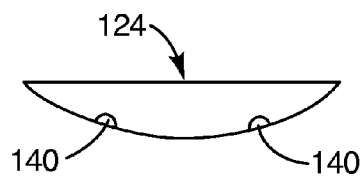
FIG. 12F illustrates a side elevation view of a representative embodiment of the footplate.
Figure 12G:
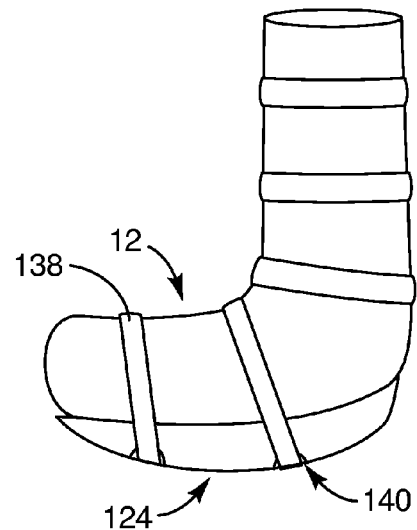
FIG. 12G illustrates a side elevation view of the footplate attached to the cast in accordance with a representative embodiment.
Figure 12H:
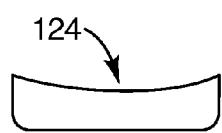
FIG. 12H illustrates a front elevation view of the footplate in accordance with some embodiments of the invention.
Figure 12I:
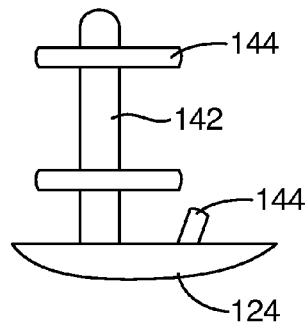
FIG. 12I illustrates a side elevation view of a representative embodiment of a boot.

As yet another example of a suitable characteristic of the footplate 124, the footplate can attach to a cast (e.g., the described cast 12 and/or any other suitable cast), a splint, a leg, a foot, and/or any other suitable object in any suitable manner that allows it to be used as intended. Indeed, although in some embodiments, the footplate and cast (e.g., cast 12) are integrally connected (e.g., via one or more adhesives, pieces of tape, types of welding, types of stitching, mechanical fasteners, and/or any other suitable mechanism), in other embodiments, the two components are selectively attachable (e.g., via one or more straps, hook and loop fasteners, cords, etc.). In one example, FIG. 12E shows the cast 12 and footplate are attached via an adhesive (not shown), a hook and loop fastener (not shown), a piece of tape (not shown), a portion of the footplate being wrapped within a portion of the cast (not shown), and/or in any other suitable manner. In another example, FIGS. 12F and 12G show that (in some embodiments) the footplate 124 is configured to receive one or more straps, cords, and/or other binding 138 (e.g., in the binding indentations 140 or otherwise) that are wrapped around a portion of the footplate and cast to secure the footplate to the cast.

As another example of a suitable method for connecting the footplate 124 to a cast, leg, and/or another suitable component, in some embodiments, the footplate comprises one or more upright supports that allow the footplate to be anchored to a patient's leg. In this manner, the footplate can be used as a boot 18.

Figure 12J:
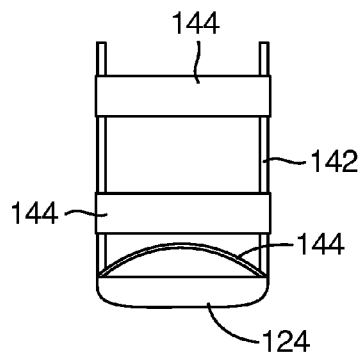
FIG. 12J illustrates a front elevation view of a representative embodiment of the boot.
Figure 12K:
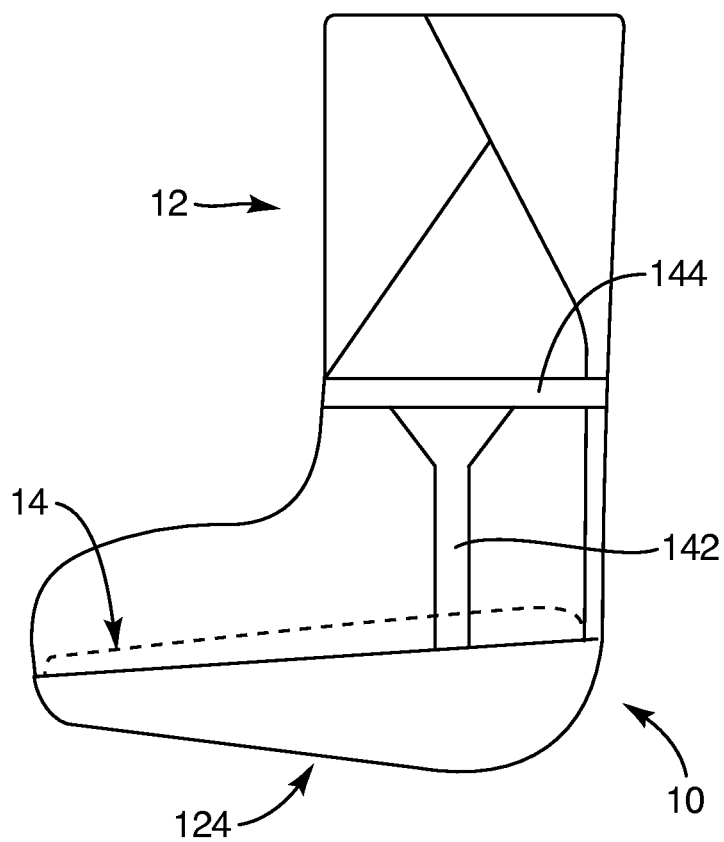
FIG. 12K illustrates a side elevation view of a representative embodiment of the boot.

While the upright supports can comprise any suitable component, FIGS. 12J through 12L show that some embodiments of the upright supports 142 are configured to be attached to one or more attachment mechanisms 144, which may include, but are not limited to, 1, 2, 3, 4, 5, 6, 7, 8, or more straps, cords, and/or other devices that are capable of securing the upright supports to a patient's leg/cast. Additionally, FIG. 12L shows that some embodiments of the upright supports 142 include and/or are attached to one or more flaps 146 (e.g., lateral/medial flaps 148, posterior flaps 150, and/or anterior flaps 152, as respectively shown in FIGS. 12M, 12N, and 12O) that help distribute pressure on the upright supports across a portion of the patient's leg to further offload weight from a wound on the patient's foot. In some such embodiments, the flaps can have any suitable characteristic. Indeed, in some embodiments, one or more of the internal surfaces of the flaps (e.g., the surfaces that are configured to interface with the cast) comprises a material, texturing, and/or other feature that allows it to maintain its position with respect to the cast (e.g., as the patient walks in the boot).

Figure 12Q:
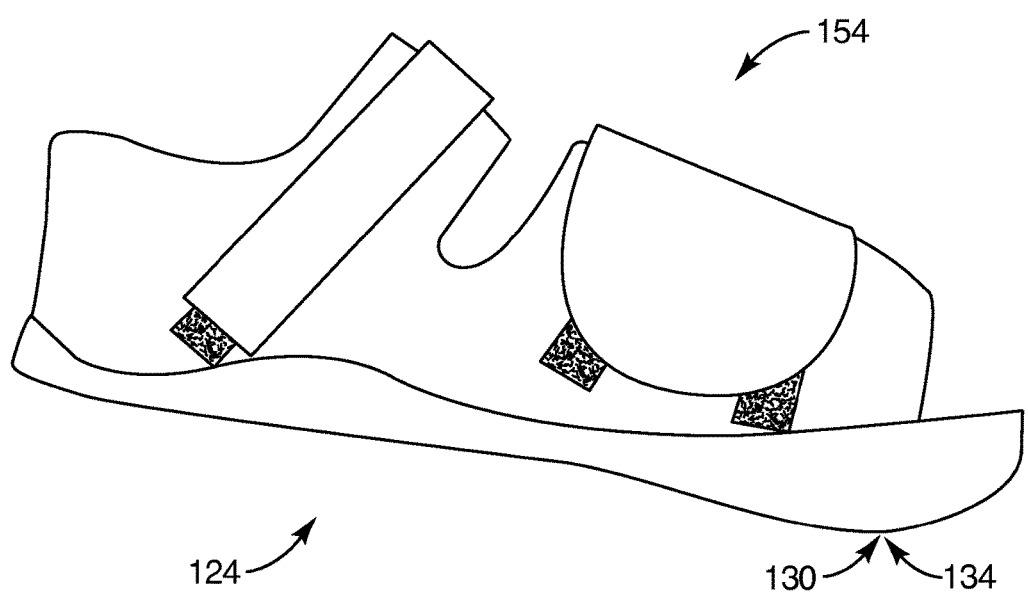
FIG. 12Q illustrates a side elevation view in which the footplate is attached to a shoe in accordance with some embodiments of the invention.

The described footplate 124/boot 18 can be modified in any suitable manner that allows it to fulfill its intended purpose. In one example, the footplate/boot can be modified to include any and/or all components of the described cast system 10. For instance, in some embodiments (e.g., as shown in FIG. 12K), the foot support 14 is attached to the footplate 12. In another example, the footplate is attachable to any suitable and known or novel slipper, sandal, shoe, overshoe (e.g., galoshes), slide, and/or other footwear/cast wear. By way of non-limiting illustration, FIG. 12Q shows a representative embodiment in which the footplate 124 is attached to a shoe 154.

Associated Methods

The various components of the described cast system 10 can be used in any suitable manner that allows the components (individually or in combination) to help protect a wounded portion of a patient's body. In this regard, the various components of the described cast system can be used in any suitable combination, meaning that virtually any portion of the cast system can be omitted, any portion of the cast system can be replaced with one or more other known or novel components, and that any suitable component (including, without limitation, any suitable wound dressing, primary contact wound dressing, cast, underlayment, boot, footplate, sock, shoe, ointment, negative pressure mechanism, positive pressure mechanism, and/or any other suitable mechanism, medicine, and/or treatment) can be added to (or used with) one or more components of the described cast system.

Figure 13:
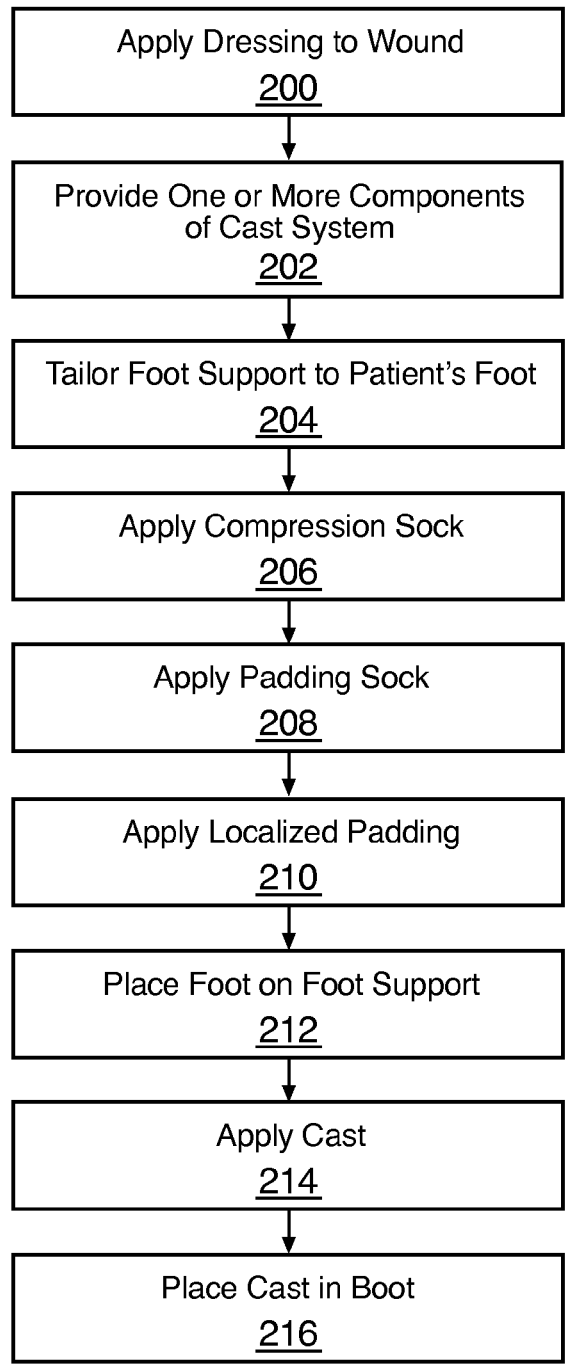
FIG. 13 depicts a representative embodiment of a method for applying the cast system.

While the described components of the cast system 10 can be applied a patient in any suitable manner, FIG. 13 illustrates some embodiments of a method 198 for placing the cast system on a patient. This method, however, can be modified in any suitable manner (including by rearranging, adding to, removing, substituting, and/or otherwise modifying one or more portions of the method).

As shown at step 202 in FIG. 13, in at least some embodiments, the method 198 optionally begins at step 200 by applying any suitable and known or novel wound dressing (e.g., a primary contact wound dressing) to the wound. Step 202 shows that, in some embodiments, the method 198 continues by providing one or more elements of the described cast system 10 (e.g., the cast 12, foot support 14, compression sock 110, padding sock 112, localized padding 114, boot 18, and/or footplate 124).

Step 204 shows that in some embodiments in which the cast system 10 comprises a foot support 14, the method 198 continues as the foot support is optionally tailored for the patient's foot. While the foot support can be tailored for the patient's foot in any suitable manner, in some embodiments, a patient's foot is placed on the foot support (e.g., somewhat posterior to an anterior end of the foot support to avoid to impingement), an outline of the patient's foot is made on the foot support, and portions of the foot support that fall outside of the outline are removed (e.g., via tearing perforations 102, cutting the support with scissors, etc.). In some embodiments in which the patient's foot comprises a wound, the location of the wound is determined, and a corresponding portion of the foot support is removed to create an offloading hole 92. Additionally, in some embodiments, once the foot support has been cut to match an outline of the patient's foot and an offloading hole has been created, the foot support is placed up against the patient's foot to ensure that the foot support has been properly tailored.

Continuing with the method 198, step 206 shows that in some embodiments in which the method includes applying a compression sock 110, the sock can be applied (e.g., to a bandaged or un-bandaged lower leg 24). While this sock can be applied in any suitable manner, in some embodiments, the compression sock is rolled, slid, and/or otherwise placed on the patient such that the patient's toes can receive proper ventilation.

At step 208, FIG. 13 shows that in some embodiments in which the cast system 10 comprises a padded sock 112, the padded sock is applied to the patient's leg (e.g., over the compression sock 110). While the padded sock can be applied in any suitable manner, in some embodiments, a proximal portion of the sock (e.g., a portion that is adjacent to the patient's knee) is folded back on itself, distal to the patient's knee (e.g., one to three fingers width below the patient's fibula head).

At step 210, FIG. 13 shows that, in some embodiments in which the cast system 10 comprises a piece of localized padding 114 (e.g., a shin pad 116), the localized padding is optionally applied to the patient's lower leg 24. While the localized padding can be applied in any suitable manner, in some embodiments, the localized padding comprises an adhesive that allows it to adhere to a surface (e.g., to a surface of the padding sock 112). Additionally, in some embodiments, a portion of the localized padding is tucked under the folded back portion of the padding sock.

At step 212, FIG. 13 shows that in some embodiments in which the cast system 10 comprises the foot support 14, the patient's foot (e.g., a foot that is covered with the compression sock 110 and the padding sock 112) is placed on the foot support 14.

Figure 14A:
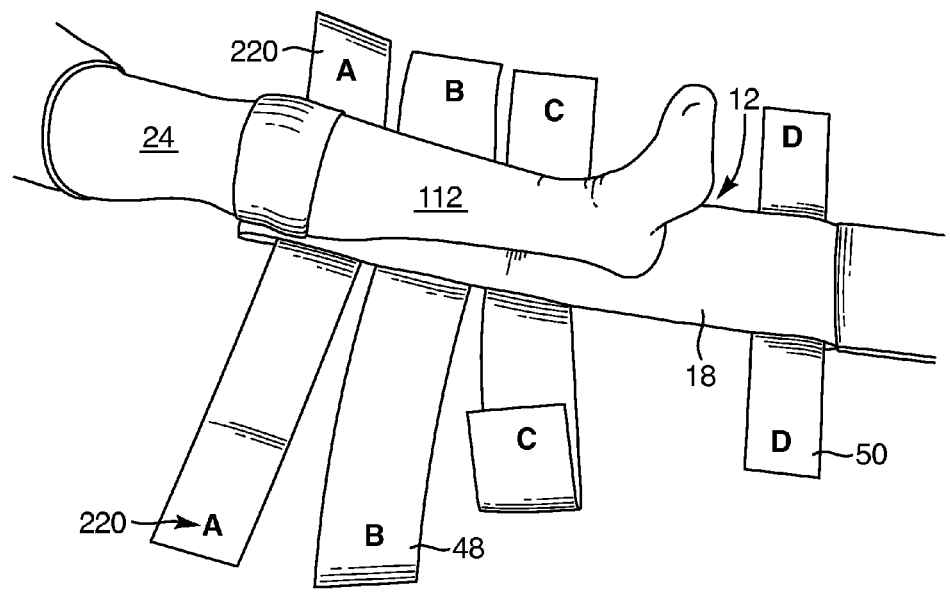
FIGS. 14A-14F each illustrates various views of the representative cast system at different points in an application process according to some embodiments of the present invention.
Figure 14B:
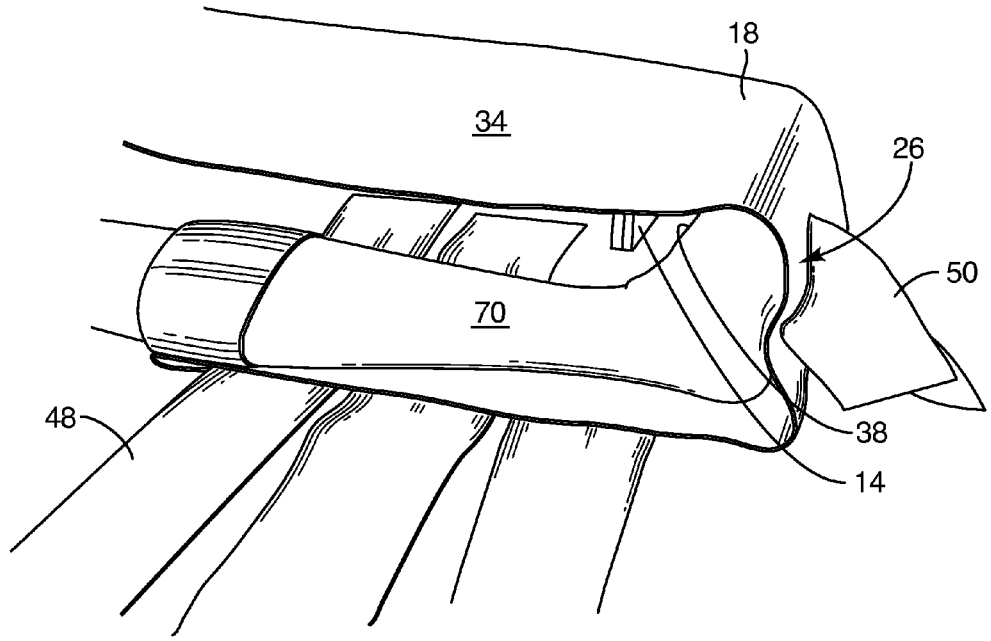

Continuing with the method 198, step 214 shows that, in some embodiments in which the cast system 10 comprises the clam-shell cast 12, the cast is applied to the patient's lower leg 24. While the cast can be applied to a patient in any suitable manner, FIGS. 14A-14F show that, in some embodiments, once the casting material 18 is ready (e.g., wetted; removed from an air-tight package, a foil package, and/or other suitable package; and/or otherwise prepared), the patient's leg 24 is placed on the unfolded cast 12 (e.g., as shown in FIG. 14A), and the second 26 and third 34 portions of the elongated casting material 18 are folded over the dorsal portion 38 and shin portion 70 (e.g., as shown in FIG. 14B).

While the straps 48 and 50 can be wrapped around the cast 12 in any suitable manner, in some embodiments, the straps are configured to be matched and wrapped around or with each other. In this regard, the various portions of each strap can be matched, wrapped, and/or otherwise connected with any other portion of itself and/or any other strap. In some embodiments, however, one or more straps are optionally marked to indicate which straps should be matched and/or connected with each other. In this regard, the various straps can be marked in any suitable manner that allows them to be readily matched. Indeed, in some embodiments, the straps matching straps comprise one or more matching markings (e.g., symbols, letters, words, and/or other markings), matching colors (e.g., colors of material and/or thread), and/or any other suitable matching mechanism that allows a user (e.g., a medical practitioner) to quickly identify which straps match and/or should be connected with each other. By way of non-limiting illustration, FIG. 14A shows some embodiments in which the straps 48 and 50 comprise a strap matching mechanism 220 in which straps (e.g., straps 48 and 50) that should be connected together are marked with the same letter (e.g., A, B, C, or D).

Figure 14C:
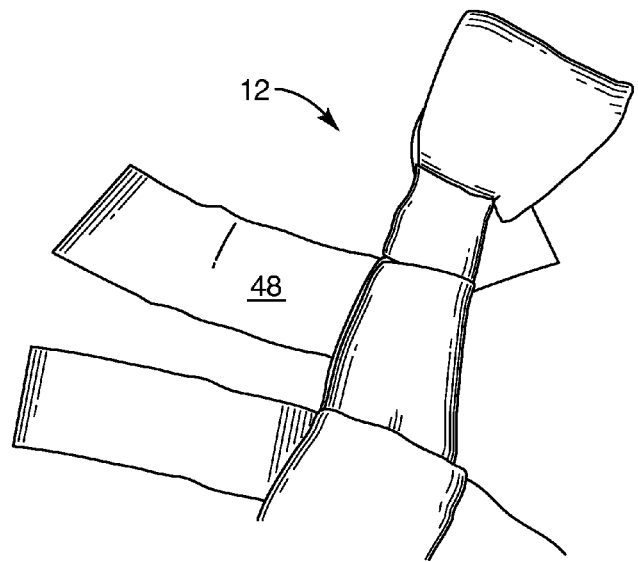
Figure 14D:
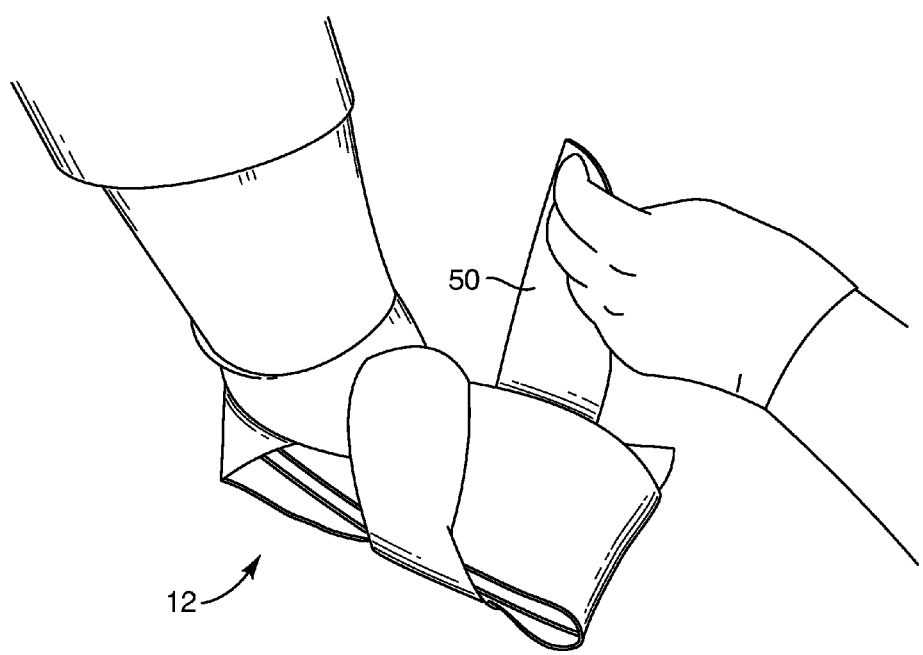
Figure 14E:
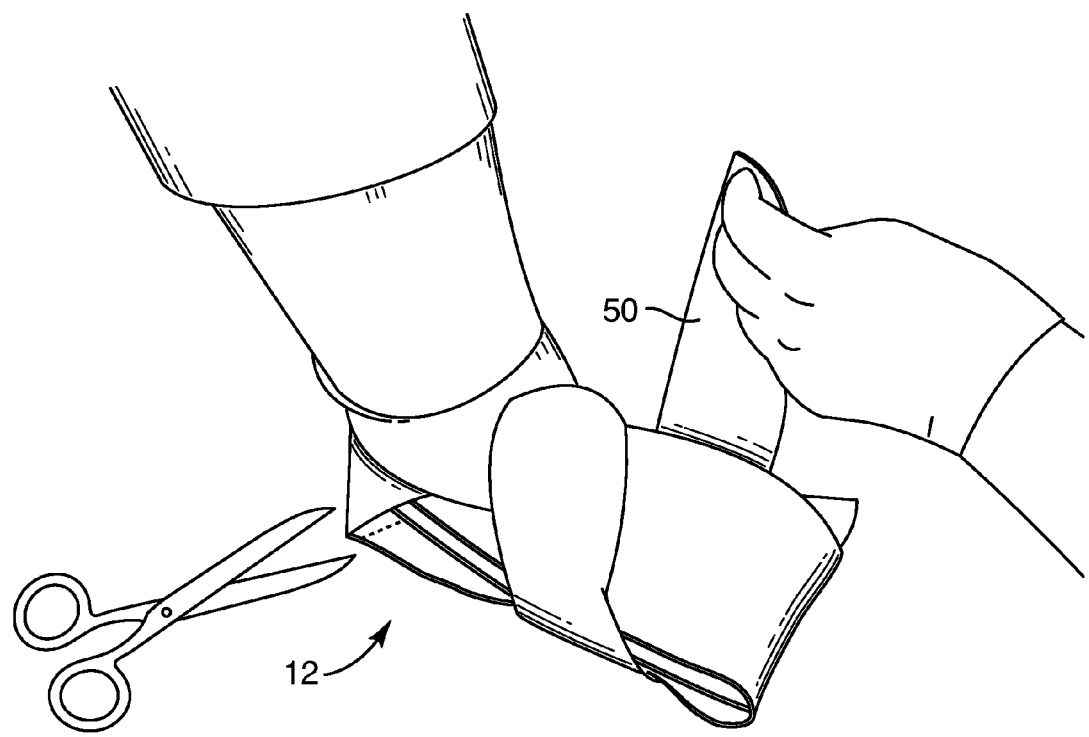
Figure 14F:
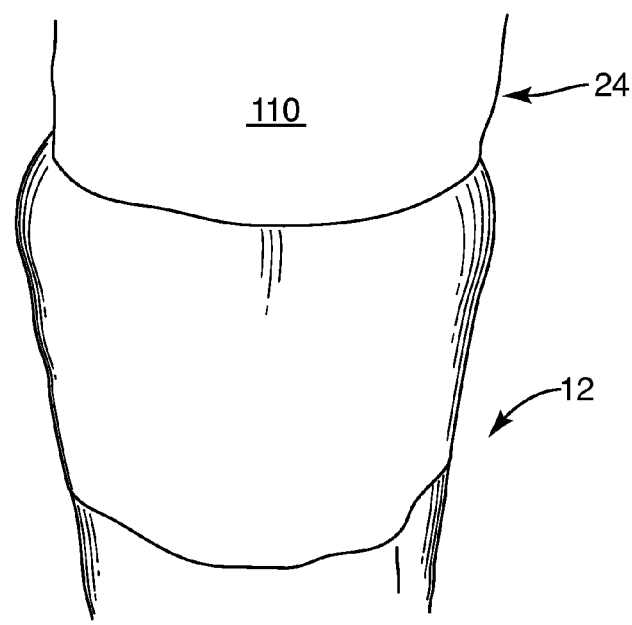

In any case, FIGS. 14C-14D show that, in some embodiments, the straps 48 and 50 are wrapped into position while the foot is kept at a suitable angle (e.g., about 90±10 degrees) with respect to the leg, cuts 62 or notches 60 are formed at the heel or other bend points (e.g., FIG. 14E), additional casting material (not shown) is optionally removed from one or more portions of the cast, additional casting material is rolled or otherwise placed on one or more portions of the cast (e.g., in some embodiments, strengthening the cast and/or covering one or more holes 64 or openings in the cast), and/or a proximal end of the compression sock 110 is folded over a proximal end of the cast 12 (e.g., FIG. 14F). In some embodiments, water is also applied to the cast to smooth the cast out before it hardens.

Returning to FIG. 13, step 216 shows that, in some embodiments, the method 198 continues as the cast 12 is placed in a boot 18 and/or footplate 124 (e.g., as shown in FIG. 1A). In this regard (and as discussed above), the cast be placed in any known or novel boot that is suitable for use with the cast. Additionally, in some embodiments, the method 198 is repeated one or more times to help a wound to heal.

The various components of the described cast system 10 can be formed in any suitable manner, including, without limitation, through weaving, knitting, extrusion, molding, heating, pressing, wrapping, cutting, folding, sewing, scoring, adhering, perforating, attaching with fasteners, bending, and/or any other suitable technique. Additionally, although, in some embodiments, one or more components of the described cast system are sterilized before being brought to market, in some other embodiments, one or more components of the cast system are left unsterilized.

Thus, the present invention relates to orthopedic casts. In particular, some implementations of the present invention relate to one or more components of a total contact cast system that can be used in the treatment of an appendage, such as a leg or foot. More particularly, in some implementations of the described casting system are configured to support a patient's foot and leg, while offloading weight from a sore, ulcer, and/or wound on the patient's foot.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples, implementations, and embodiments, in all respects, are meant to be illustrative only and should not be construed to be limiting in any manner. In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., on top of, below, above, top, bottom, side, up, down, under, over, upper, lower, lateral, medial, vertical, horizontal, distal, proximal, etc.), if provided, are relative and provided solely by way of example and for ease of illustration and discussion and not by way of limitation. Furthermore, where reference is made herein to a list of elements (e.g., elements a, b, c), such reference is intended to include any one of the listed elements by itself, any combination of less than all of the listed elements, and/or a combination of all of the listed elements. Also, as used herein, the terms a, an, and one may each be interchangeable with the terms at least one and one or more. It should also be noted, that while the term step is used herein, that term may be used to simply draw attention to different portions of the described methods and is not meant to delineate a starting point or a stopping point for any portion of the methods, or to be limiting in any other way.

What is claimed is:

1. A method for applying an orthopedic cast to a patient, the method comprising:
    obtaining an orthopedic cast comprising an elongated piece of a hardenable casting material;
    placing a first length of the elongated piece of the casting material over a first surface of an appendage;
    placing a second length of the elongated piece of the casting material over an end of the appendage, said second length covering at least a portion of a toe of said appendage;
    placing a third length of the elongated piece of the casting material over a second surface of the appendage, wherein the second surface is substantially opposite to the first surface; and
    securing the first length to the third length; and
    securing the second length to the third length via at least one of a strap and a wing.

2. The method of claim 1, wherein the orthopedic cast is configured to be placed on the patient while the patient is in at least one of a sitting, a prone, and a supine position.

3. The method of claim 1, wherein the elongated casting material defines a ventilation hole.

4. The method of claim 1, further comprising placing a cast underlayment comprising an antimicrobial material on the appendage.

5. The method of claim 1, further comprising placing a compression sock on the appendage.

6. The method of claim 5, further comprising placing a padding sock on the appendage.

7. The method of claim 6, further comprising attaching at least a portion of the padding sock to the orthopedic cast.

8. A method for applying an orthopedic cast to a patient the method comprising:
    obtaining an orthopedic cast, comprising an elongated piece of a hardenable casting material; placing a first length of the elongated piece of the casting material over a posterior surface of the patient's lower leg;
    placing a second length of the elongated piece of the casting material over a portion of a heel, a sole, and a toe of the patient's lower leg;
    placing a third length of the elongated piece of the casting material over an anterior surface of the patient's lower leg, wherein the first length, the second length, and the third length of the elongated piece of the casting material are integrally connected together; and
    securing the first length to the third length via at least one of a first strap and a first wing.

9. The method of claim 8, further comprising placing a first underlayment component and a second underlayment component over a portion of the patient's lower leg.

10. The method of claim 9, wherein the first underlayment component and the second underlayment component are independently moveable within the orthopedic cast with respect to each other.

11. The method of claim 9, wherein the first underlayment component comprises a compression sock and wherein the second underlayment comprises a padding sock.

12. The method of claim 9, wherein the first underlayment component comprises an antimicrobial material.

13. The method of claim 8, further comprising obtaining a foot support comprising a built-in toe guard, and placing a foot of the patient's lower leg in the foot support.

14. The method of claim 13, further comprising removing a portion of the foot support corresponding in position to a wound on the foot to form an offloading hole.

15. A method for applying a total contact cast to a patient, the method comprising:
obtaining a total contact cast, comprising:
an elongated piece of a hardenable casting material having a first length, a second length, and a third length; and
a first strap portion of the hardenable casting material that extends laterally from at least one of a lateral edge and a medial edge of the elongated piece of the casting material;
placing the first length of the elongated piece of the casting material over a posterior surface of the patient's lower leg;
placing the second length of the elongated piece of the casting material over a portion of a heel, a sole, and a toe of the patient's lower leg;
placing the third length of the elongated piece of the casting material over an anterior surface of the patient's lower leg; and
securing the first length to the third length by wrapping the first strap portion between the first and third length.

16. The method of claim 15, further comprising placing a compression sock and a padding sock on a portion of the patient's lower leg.

17. The method of claim 16, wherein the compression sock comprises an antimicrobial material.

18. The method of claim 16, wherein the antimicrobial material comprises a bamboo material.

19. The method of claim 16, further comprising coupling a portion of the padding sock to an internal surface of the total contact cast.

20. The method of claim 16, wherein the first strap portion comprises a matching mechanism identifying a second strap portion to which the first strap portion should be connected.

21. A method for applying an orthopedic cast to a patient, the method comprising:
obtaining an orthopedic cast comprising an elongated piece of a hardenable casting material;
placing a first length of the elongated piece of the casting material over a first surface of an appendage;
placing a second length of the elongated piece of the casting material over an end of the appendage;
placing a third length of the elongated piece of the casting material over a second surface of the appendage, wherein the second surface is substantially opposite to the first surface;
securing the first length to the third length;
placing a compression sock on the appendage;
placing a padding sock on the appendage;
attaching at least a portion of the padding sock to the orthopedic cast.

* * * * *